US011236315B2

United States Patent
Donovan et al.

(10) Patent No.: US 11,236,315 B2
(45) Date of Patent: Feb. 1, 2022

(54) THERMOPHILE PEPTIDOGLYCAN HYDROLASE FUSION PROTEINS AND USES THEREOF

(71) Applicants: The United States of America, as Represented by the Secretary of Agriculture, Washington, DC (US); University of Maryland, College Park, MD (US)

(72) Inventors: David M. Donovan, Essex, MD (US); Steven M. Swift, Bethesda, MD (US)

(73) Assignees: The United States of America, as represented by the Secretary of Agriculture, Washington, DC (US); University of Maryland, College Park, MD (US)

( * ) Notice: Subject to any disclaimer, the term of this patent is extended or adjusted under 35 U.S.C. 154(b) by 375 days.

(21) Appl. No.: 16/375,287

(22) Filed: Apr. 4, 2019

(65) Prior Publication Data

US 2020/0318090 A1    Oct. 8, 2020

(51) Int. Cl.
| | |
|---|---|
| *C12N 9/36* | (2006.01) |
| *A23K 20/147* | (2016.01) |
| *A61P 31/04* | (2006.01) |
| *A61K 38/00* | (2006.01) |
| *A23K 50/75* | (2016.01) |
| *C12N 15/62* | (2006.01) |

(52) U.S. Cl.
CPC .......... *C12N 9/2462* (2013.01); *A23K 20/147* (2016.05); *A61P 31/04* (2018.01); *C12Y 302/01017* (2013.01); *A61K 38/00* (2013.01)

(58) Field of Classification Search
None
See application file for complete search history.

(56) References Cited

PUBLICATIONS

Abaev I. et al., 2013, "Staphylococcal phage 2638A endolysin is lytic for *Staphylococcus aureus* and harbors an inter-lytic-domain secondary translational start site," Appl. Microbiol. Biotechnol. 97(8): 3449-3456.
Ajuebor J. et al., 2016, "Bacteriophage endolysins and their applications," Sci. Progress—UK 99(2): 183-199.
Becker S.C. et al., 2009, "LysK CHAP endopeptidase domain is required for lysis of live staphylococcal cells," FEMS Microbiol. Lett. 294:52-60.
Castanon J.I.R., 2007, "History of the use of antibiotic as growth promoters in European poultry feeds," Poult. Sci. 86(11): 2466-2471.
Diaz E. et al., 1990, Chimeric phage-bacterial enzymes: a clue to the modular evolution of genes, Proc. Natl. Acad. Sci. U.S.A. 87(20):8125-8129.
Dibner J.J. and Richards J.D., 2005, "Antibiotic growth promoters in agriculture: history and mode of action," Poult. Sci. 84(4): 634-643.
Donovan D.M. et al., 2006, "Lysis of staphylococcal mastitis pathogens by bacteriophage phi11 endolysin," FEMS Microbiol. Lett. 265:133-139.
Donovan D.M. et al., 2006, "The cell lysis activity of the *Streptococcus agalactiae* bacteriophage B30 endolysin relies on the cysteine, histidine-dependent amidohydrolase/peptidase domain," Appl. Environ. Microbiol. 72:5108-5112.
Donovan D.M. and Foster-Frey J., 2008, "Lambda Sa2 prophage endolysin requiresCpl-7-binding domains and amidase-5 domain for antimicrobial lysis of streptococci," FEBS Microbiol. Lett. 287:22-33.
Donovan D.M. et al., 2006, "Peptidoglycan hydrolase fusions maintain their parental specificities," Appl. Environ. Microbiol. 72(4):2988-2996.
Garcia P. et al., 1990, "Modular organization of the lytic enzymes of *Streptococcus pneumoniae* and its bacteriophages," Gene 86:81-88.
Mao J., et al., 2013, "Chimeric Ply187 endolysin kills *Staphylococcus aureus* more effectively than the parental enzyme," FEMS microbiol. Lett. 342: 30-36.
Millet S. and Maertens L., 2011, "The European ban on antibiotic growth promoters in animal feed: from challenges to opportunities," Vet. J. 187:143-144.
Nelson D.C. et al., 2012, "Endolysins as Antimicrobials," Adv. Virus Res. 83: 299-365.
Rodriguez-Rubio L. et al., 2013, "The Peptidoglycan Hydrolase of *Staphylococcus aureus* Bacteriophage φ11 Plays a Structural Role in the Viral Particle," Appl. Env. Microbiol. 79(19): 6187-6190.
Schmelcher D. M. et al., 2012, "Bacteriophage endolysins as novel antimicrobials," Future Microbiol. 7(10): 1147-1171.
Schmitz J.E. et al., 2011, "Lytic enzyme discovery through multigenomic sequence analysis in Clostridium perfringens," Appl. Microbiol. Biotechnol. 89(6):1783-1795.
Seal B.S. et al., 2013, "Alternatives to antibiotics: a symposium on the challenges and solutions for animal production," Anim. Health Res. Rev. 14(1): 78-87.
Swift S.M. et al., 2018, "Characterization of Two Glycosyl Hydrolases, Putative Prophage Endolysins, That Target Clostridium perfringens," FEMS Microbiology Letters 365(16), Aug. 1, 2018, fny179.
Swift S.M. et al., 2015, "A Thermophilic Phage Endolysin Fusion to a Clostridium perfringens-Specific Cell Wall Binding Domain Creates an Anti-Clostridium Antimicrobial with Improved Thermostability," Viruses 7(6): 3019-3034.

*Primary Examiner* — Suzanne M Noakes
*Assistant Examiner* — Jae W Lee
(74) *Attorney, Agent, or Firm* — John D. Fado; Maria Restrepo-Hartwig

(57) ABSTRACT

The disclosure relates to chimeric recombinant lysins comprising at least one thermophile endolysin catalytic domain and at least one cell wall binding domain. Also disclosed are polynucleotides encoding the chimeric recombinant lysins, host cells expressing the chimeric recombinant lysins, and use of such chimeric recombinant lysins.

Figure 1:
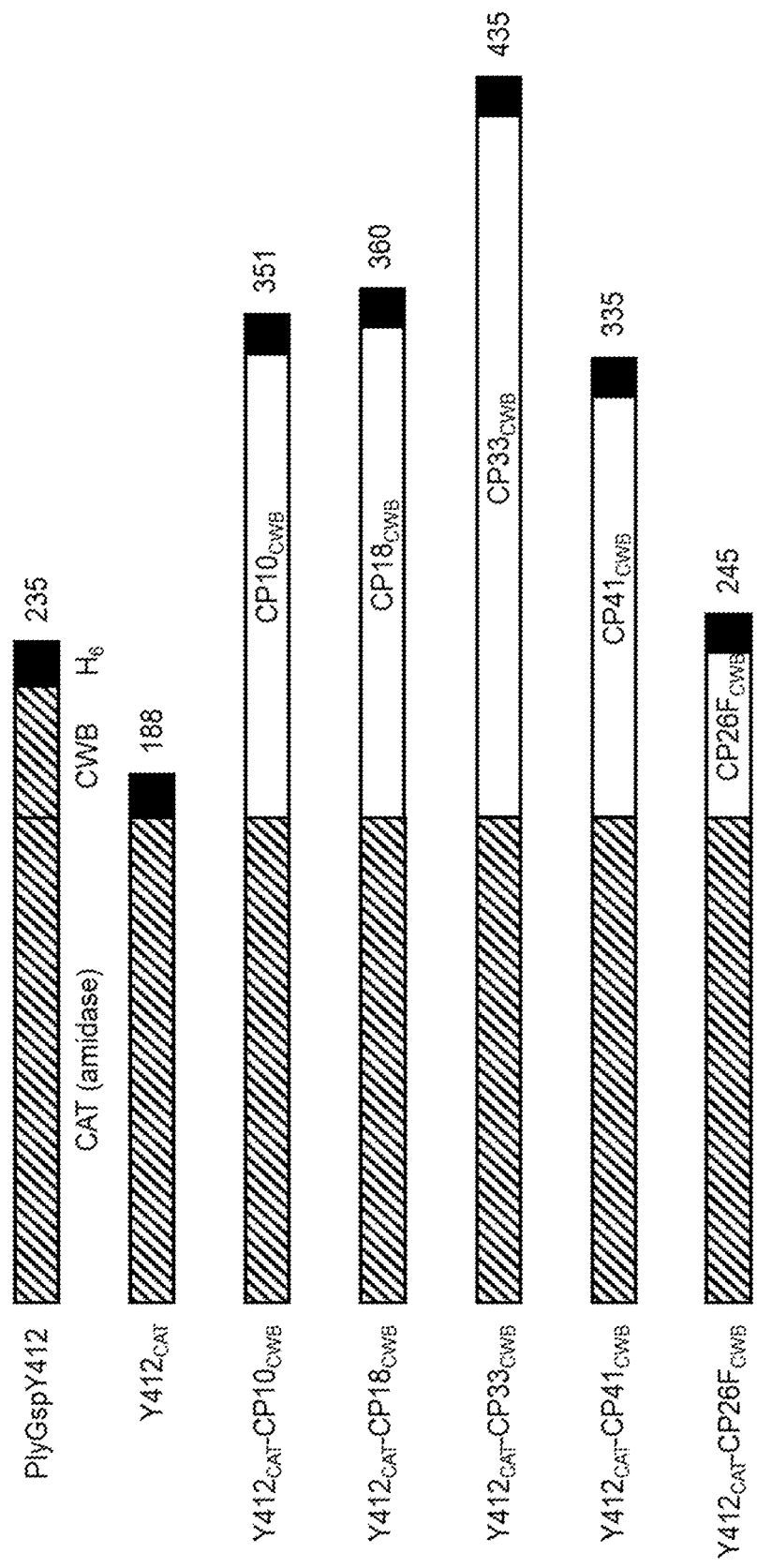
Figure 2:
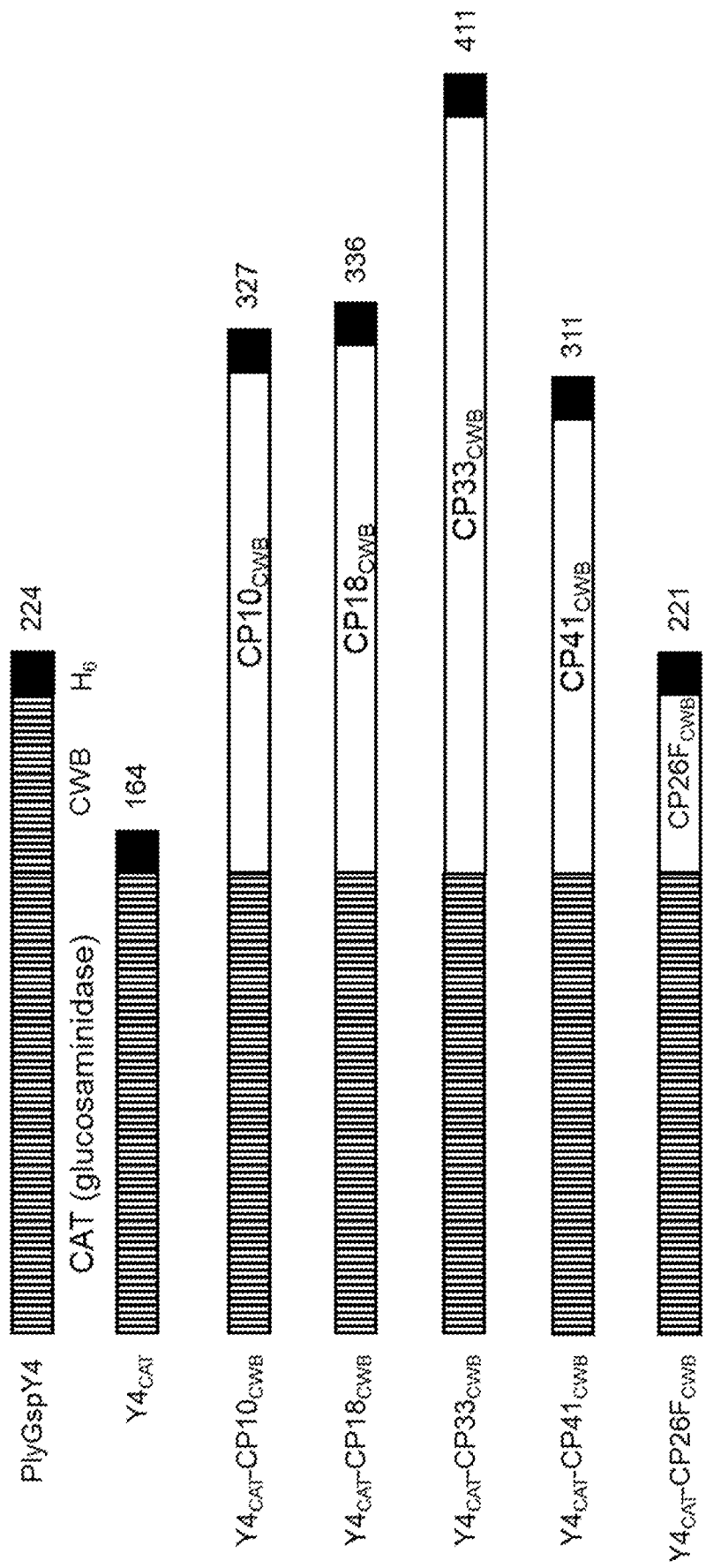
Figure 3:
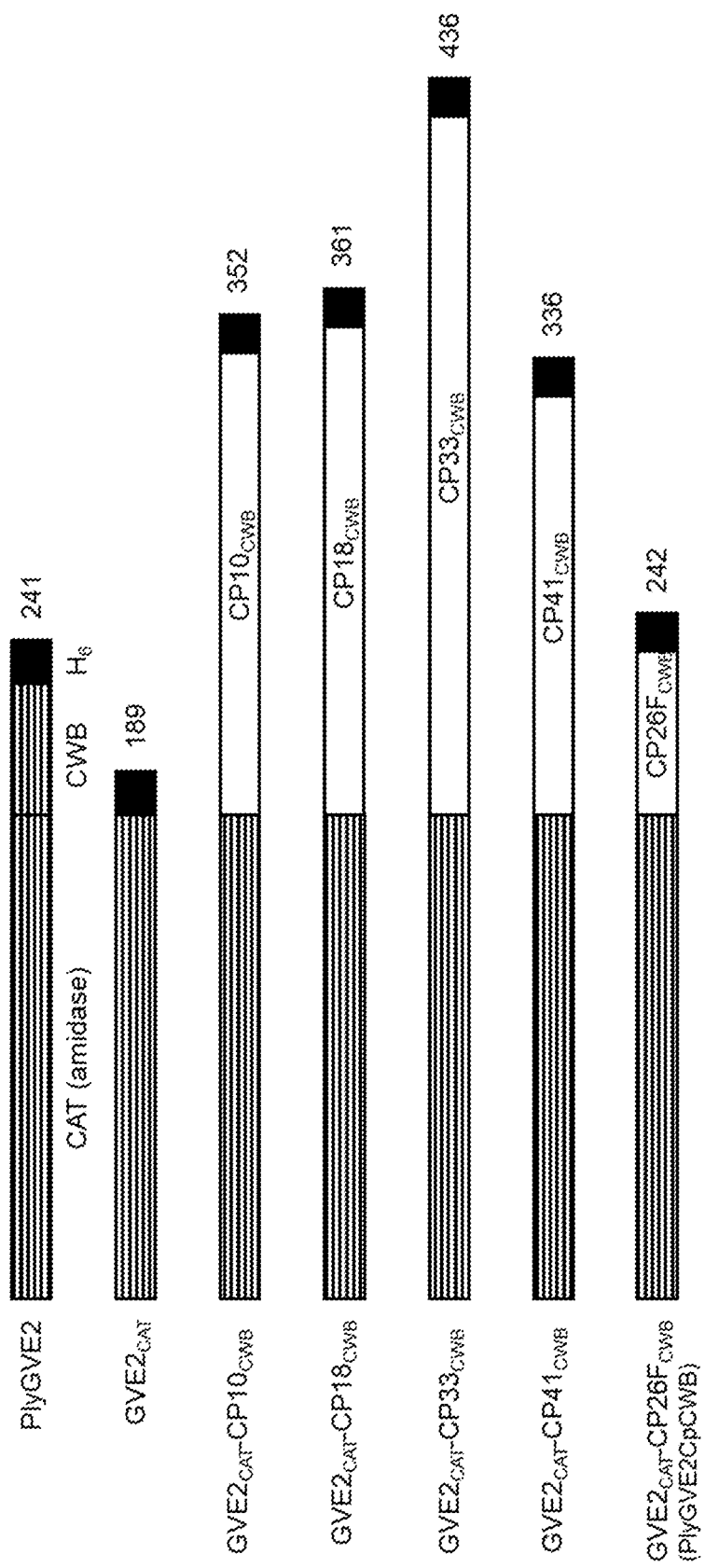
Figure 4:
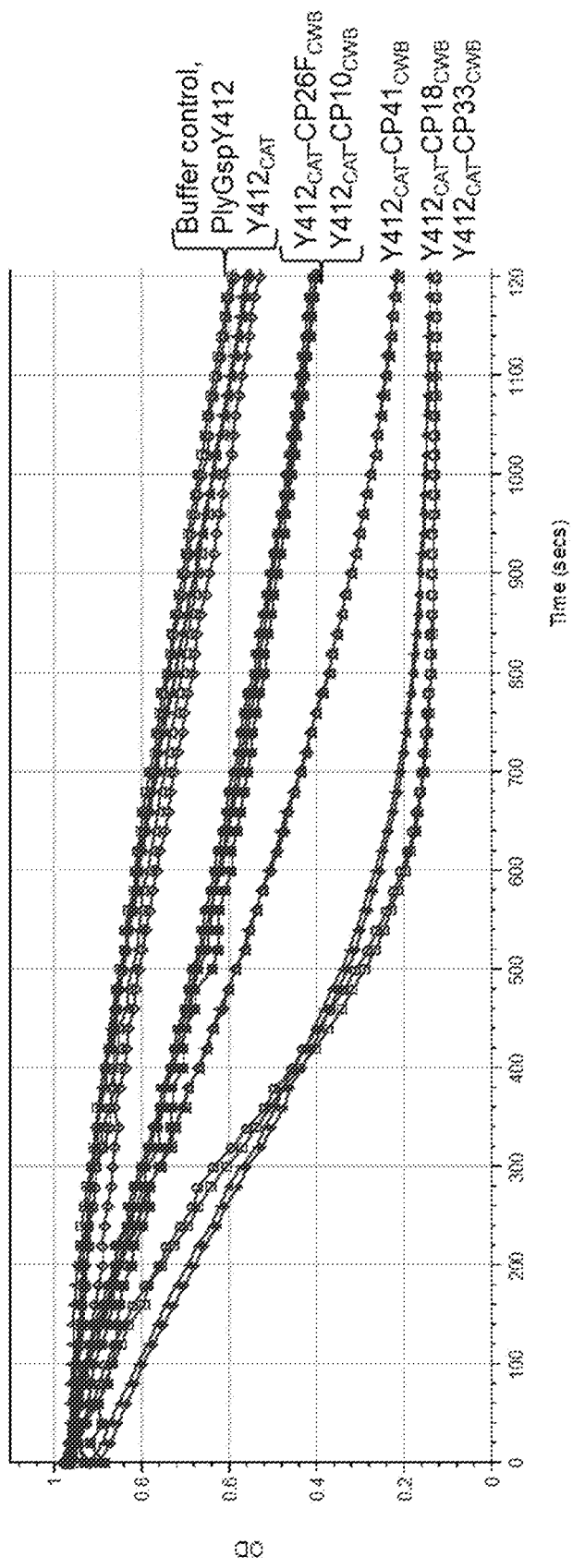
Figure 5:
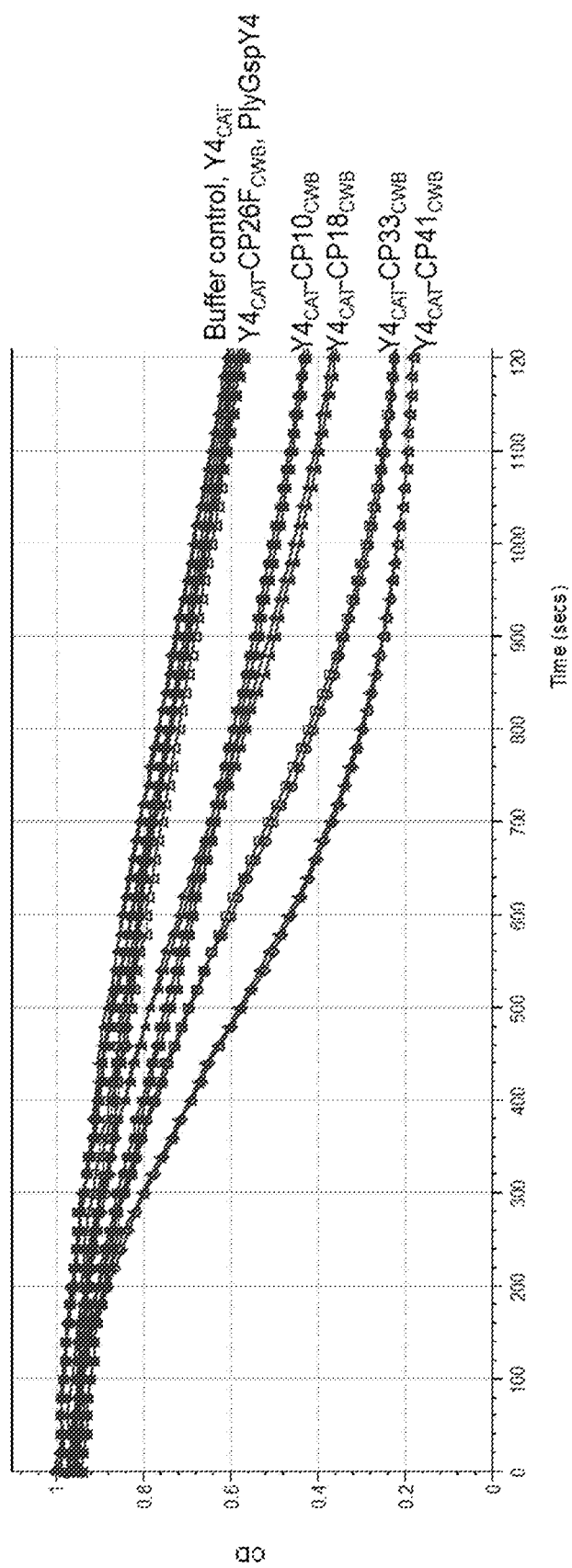
Figure 6:
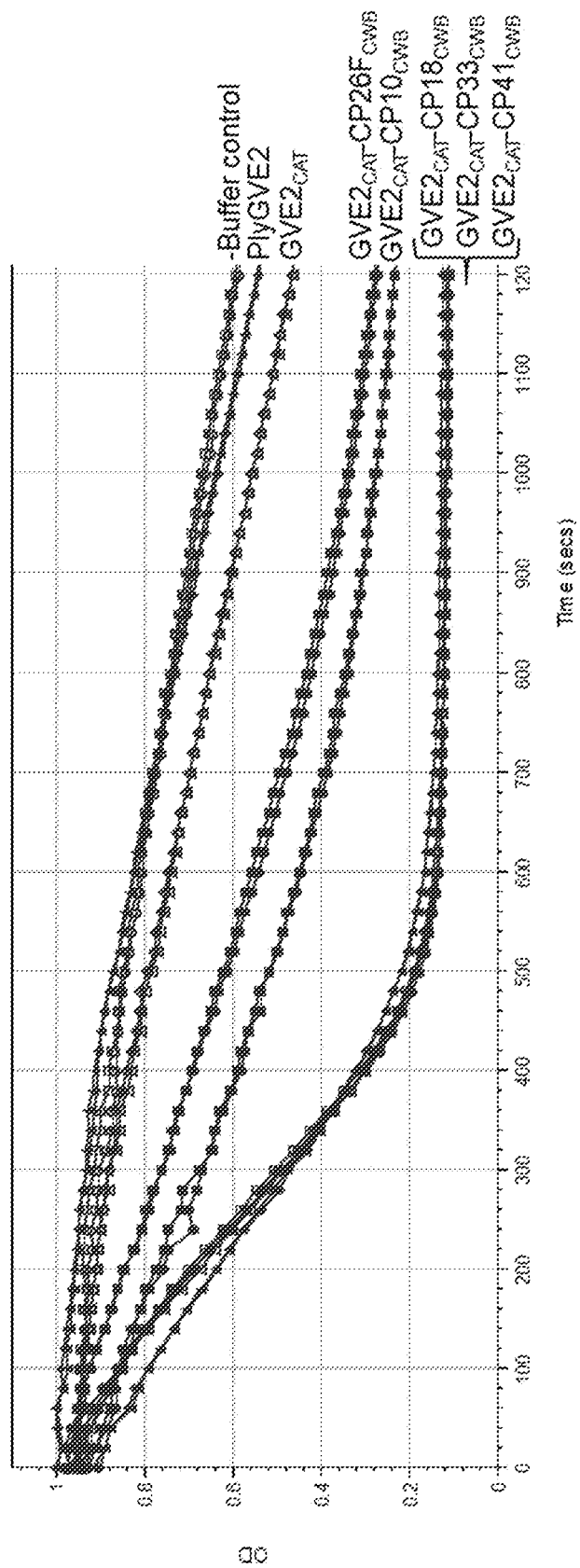
Figure 7A:
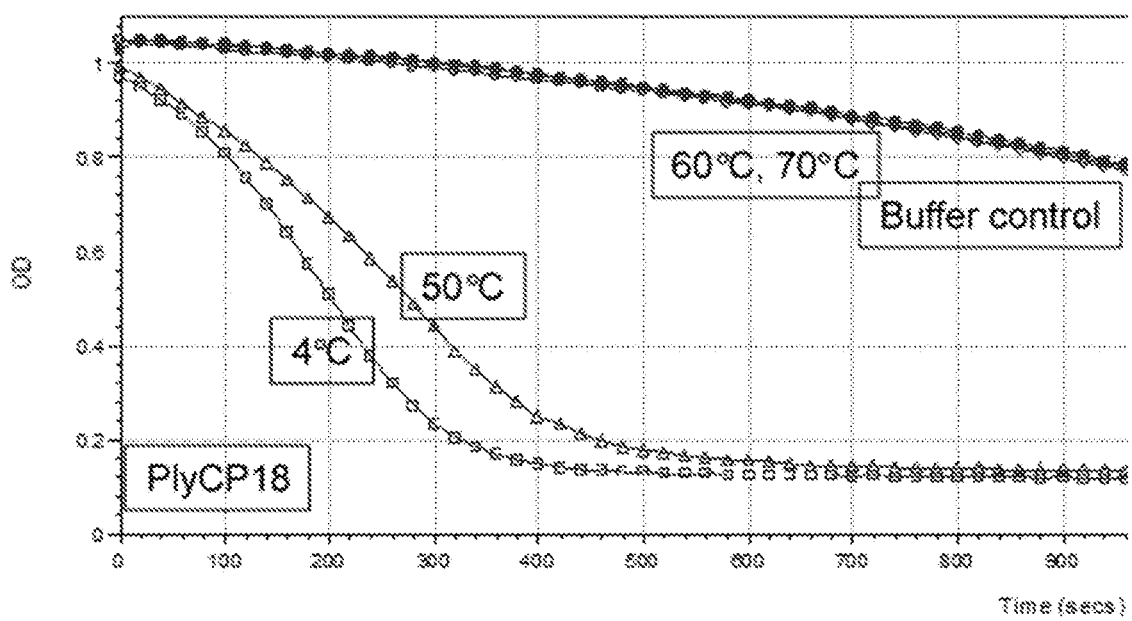
Figure 7B:
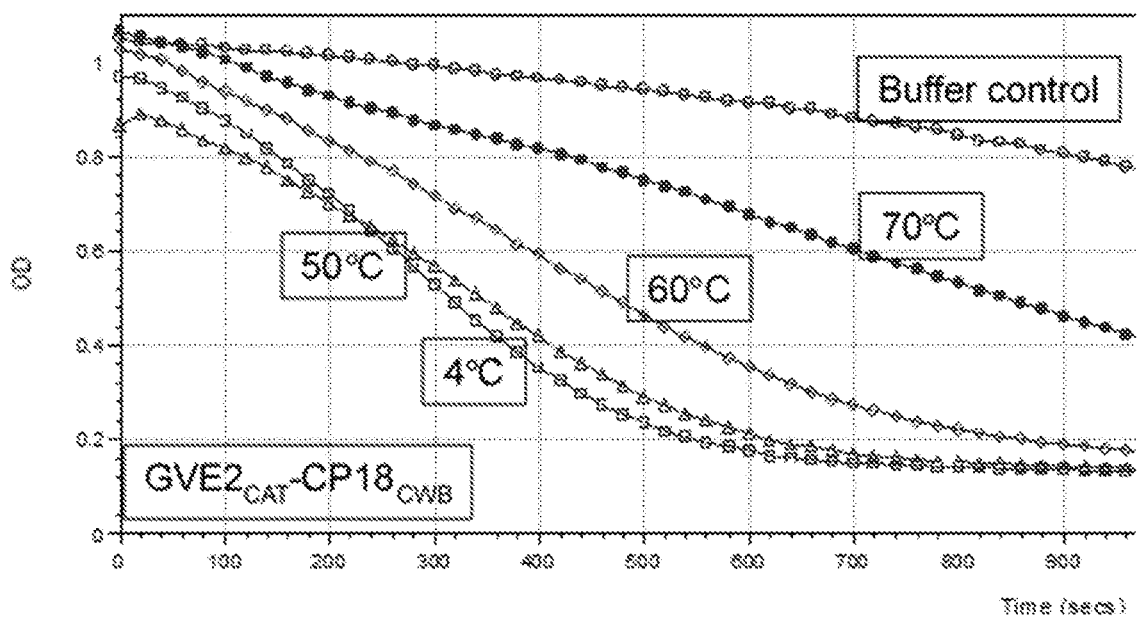

30 Claims, 10 Drawing Sheets
Specification includes a Sequence Listing.

SEQUENCE LISTING

```
<160> NUMBER OF SEQ ID NOS: 28

<210> SEQ ID NO 1
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 1

Leu Glu His His His His His His
1               5

<210> SEQ ID NO 2
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 2

Val Glu His His His His His His
1               5

<210> SEQ ID NO 3
<211> LENGTH: 235
<212> TYPE: PRT
<213> ORGANISM: Artificial Sequence
<220> FEATURE:
<223> OTHER INFORMATION: Chemically Synthesized

<400> SEQUENCE: 3
```

```
Met Met Val Arg Ile Val Leu Asp Ala Gly His Gly His Asp Pro
1               5                   10                  15

Gly Ala Val Ala Asn Gly Leu Arg Glu Lys Asp Leu Thr Leu Ala Ile
            20                  25                  30

Val Lys His Ile Gly Lys Met Leu Gly Glu Tyr Glu Gly Ala Glu Val
        35                  40                  45

His Tyr Thr Arg Thr Asp Asp Arg Phe Leu Glu Leu Ser Glu Arg Ala
    50                  55                  60

Ala Ile Ala Asn Lys Leu Lys Ala Asp Leu Leu Ile Ser Val His Ile
65                  70                  75                  80

Asn Ala Gly Gly Gly Thr Gly Phe Glu Ser Tyr Ile Tyr Asn Gly Asn
                85                  90                  95

Val Ser Pro Ala Thr Ile Ala Tyr Gln Asn Val Ile His Gln Glu Leu
            100                 105                 110

Met Lys Ala Ile Gly Asn Val Thr Asp Arg Gly Lys Lys Arg Ala Asn
        115                 120                 125

Tyr Ala Val Leu Arg Glu Thr Asn Met Pro Ala Ile Leu Thr Glu Asn
    130                 135                 140

Leu Phe Ile Asp Asn Ala Asn Asp Ala Ala Lys Leu Lys Ser Glu Gln
145                 150                 155                 160

Phe Leu Gln Gln Val Ala Tyr Gly His Val Gln Gly Ile Val Lys Ala
            165                 170                 175

Phe Gly Leu Lys Lys Lys Ala Lys Pro Gln Thr Lys Gln Lys Val Ser
        180                 185                 190

Asp Gly Lys Leu Tyr Arg Val Gln Val Gly Ala Phe Ala Asp Pro Glu
    195                 200                 205

Asn Ala Lys Arg Leu Ala Asp Glu Leu Lys Lys Gly Tyr Pro Ala
210                 215                 220

Thr Ile Val Leu Glu His His His His His
225                 230                 235

<210> SEQ ID NO 4
<211> LENGTH: 188
<212> TYPE: PRT
<213> ORGANISM: Artificial Sequence
<220> FEATURE:
<223> OTHER INFORMATION: Chemically Synthesized

<400> SEQUENCE: 4

Met Met Val Arg Ile Val Leu Asp Ala Gly His Gly His Asp Pro
1               5                   10                  15

Gly Ala Val Ala Asn Gly Leu Arg Glu Lys Asp Leu Thr Leu Ala Ile
            20                  25                  30

Val Lys His Ile Gly Lys Met Leu Gly Glu Tyr Glu Gly Ala Glu Val
        35                  40                  45

His Tyr Thr Arg Thr Asp Asp Arg Phe Leu Glu Leu Ser Glu Arg Ala
    50                  55                  60

Ala Ile Ala Asn Lys Leu Lys Ala Asp Leu Leu Ile Ser Val His Ile
65                  70                  75                  80

Asn Ala Gly Gly Gly Thr Gly Phe Glu Ser Tyr Ile Tyr Asn Gly Asn
                85                  90                  95

Val Ser Pro Ala Thr Ile Ala Tyr Gln Asn Val Ile His Gln Glu Leu
            100                 105                 110

Met Lys Ala Ile Gly Asn Val Thr Asp Arg Gly Lys Lys Arg Ala Asn
        115                 120                 125
```

```
Tyr Ala Val Leu Arg Glu Thr Asn Met Pro Ala Ile Leu Thr Glu Asn
            130                 135                 140

Leu Phe Ile Asp Asn Ala Asn Asp Ala Ala Lys Leu Lys Ser Glu Gln
145                 150                 155                 160

Phe Leu Gln Gln Val Ala Tyr Gly His Val Gln Gly Ile Val Lys Ala
                165                 170                 175

Phe Gly Ser Ser Leu Glu His His His His His His
            180                 185

<210> SEQ ID NO 5
<211> LENGTH: 159
<212> TYPE: PRT
<213> ORGANISM: Artificial Sequence
<220> FEATURE:
<223> OTHER INFORMATION: Chemically Synthesized

<400> SEQUENCE: 5

Thr Gln Glu Ile Phe Ile Asn Gly Ala Ser Gln Lys Ala Thr Glu Asn
1               5                   10                  15

Lys Ser Phe Phe Thr Asn Ala Arg Ala Lys Val Ala Leu Asp Pro Arg
                20                  25                  30

Ser Asn Pro Ser Asp Asn Tyr Lys Asp Leu Gly Glu Ile Tyr Ala Glu
            35                  40                  45

Glu Arg Ile Gln Val Leu Ala Glu Ile Cys Arg Glu Asp Tyr Leu
50                  55                  60

Pro Val Lys Tyr Trp Lys Asp Ala Ser Gly Cys Glu Ser Ser Lys Val
65                  70                  75                  80

Trp Val Asn Ala Asn Lys Asp Tyr Leu Glu Ile Asp Thr Asn Ala Arg
                85                  90                  95

Ser Phe Asn Ile Val Thr Glu Leu Asp Ala Arg Tyr Glu Pro Ser Val
            100                 105                 110

Asn Ser Lys Arg Met Gly Tyr Val Lys Asn Asn Glu Arg Leu Tyr Val
        115                 120                 125

His Arg Val Glu Gly Asp Tyr Val Leu Ala Thr Tyr Tyr Ala Gly Asn
    130                 135                 140

Gly Tyr Lys Thr Ala Trp Phe Thr Lys Glu Tyr Ile Ile Lys Asp
145                 150                 155

<210> SEQ ID NO 6
<211> LENGTH: 170
<212> TYPE: PRT
<213> ORGANISM: Artificial Sequence
<220> FEATURE:
<223> OTHER INFORMATION: Chemically Synthesized

<400> SEQUENCE: 6

Arg Met Leu Lys Ser Ile Asp Glu Asn Ile Val Asn Asp Thr Asp Thr
1               5                   10                  15

Thr Asp Val Pro Ser Ser Asp Asp Ser Asn Lys Lys Asp Phe Ser Thr
                20                  25                  30

Asn Ala Arg Ala Leu Val Ala Leu Asp Pro Arg Asp Asn Pro Ser Asp
            35                  40                  45

Asn Tyr Ser Asp Leu Gly Glu Ile Tyr Lys Asp Glu Arg Phe Arg Val
        50                  55                  60

Leu Ala Glu Val Cys Asp Lys Gly Asp Phe Leu Pro Ile Val Tyr Trp
65                  70                  75                  80

Lys Asp Ser Glu Gly Arg Glu Ser Gly Lys Val Trp Val Arg Ser Lys
```

```
                      85                  90                  95

Gln Asp Tyr Met Met Ile Asp Thr Tyr His Lys Val Phe Asn Val Ile
                100                 105                 110

Thr Glu Leu Asp Ala Arg Tyr Glu Pro Ser Pro Asn Ser Ser Arg Met
            115                 120                 125

Gly Tyr Val Thr Asn Gly Glu Arg Leu Tyr Val His Arg Ile Glu Gly
        130                 135                 140

Asn Tyr Ala Leu Ala Thr Tyr Phe Ala Gly Asn Gly Tyr Lys Thr Ala
145                 150                 155                 160

Trp Phe Thr Lys Lys Tyr Ile Glu Lys Ile
                165                 170

<210> SEQ ID NO 7
<211> LENGTH: 243
<212> TYPE: PRT
<213> ORGANISM: Artificial Sequence
<220> FEATURE:
<223> OTHER INFORMATION: Chemically Synthesized

<400> SEQUENCE: 7

Leu Ser Glu Phe Lys Asn Asn Ser Tyr Arg Pro Thr Gly Gly Ser Ser
1               5                   10                  15

Glu Thr Val Val Ser Glu Asn Gly Phe Tyr Thr Ser Asn Glu Glu Arg
            20                  25                  30

Thr Asn Ala Thr Ile Val Gly Lys Gly Asp Ile Glu Val Leu Asp Glu
        35                  40                  45

Lys Gly Lys Val Ile Gln Gly Arg His Ile Ser Ser Leu Asp Arg Val
    50                  55                  60

Phe Val Leu Gly Ile Tyr Pro Ser Arg Asn His Ile Glu Leu Ile Tyr
65                  70                  75                  80

Pro Gly Lys Asp Glu Lys Tyr His Ala Tyr Ile Ser Ile Glu Asn Tyr
                85                  90                  95

Ser Arg Leu Ser Phe Asp Tyr His Met Gln Tyr Lys Asn Asp Asp Gly
                100                 105                 110

Val Thr Tyr Val Trp Trp Asp Ser Lys Asn Val Asn Val Lys Asn His
            115                 120                 125

Asp Glu Glu Leu Gln Pro His Gln Lys Ala Ser Pro Met Tyr Arg Thr
        130                 135                 140

Asn Gly Trp Leu Arg Val Thr Phe Tyr Arg Ala Asp Gly Asn Pro Ser
145                 150                 155                 160

Asp Gly Tyr Val Arg Tyr Glu Gly Glu Gln Lys Glu Arg Phe Tyr Arg
                165                 170                 175

Lys Gly Lys Val Val Asn Val Arg Thr Ser Leu Thr Val Arg Ala Gly
                180                 185                 190

Ala Gly Thr Asn Tyr Ser Ala Ile Gly Ser Leu Asp Pro Asn Glu Asn
            195                 200                 205

Val Glu Ile Leu Glu Lys Thr Glu Gly Trp Tyr Ile Glu Tyr Asn
        210                 215                 220

Ala Arg Asn Glu Arg Lys Arg Gly Tyr Val Ser Lys Lys Tyr Ile Glu
225                 230                 235                 240

Ile Ile Gln

<210> SEQ ID NO 8
<211> LENGTH: 143
<212> TYPE: PRT
<213> ORGANISM: Artificial Sequence
```

```
<220> FEATURE:
<223> OTHER INFORMATION: Chemically Synthesized

<400> SEQUENCE: 8

Glu Asp Phe Leu Lys Lys Asp Phe Thr Leu Glu Asn Ala Thr Thr Cys
1               5                   10                  15

Asn Val Asp Thr Glu Leu Asn Ile Arg Ala Lys Gly Thr Thr Gly Ala
            20                  25                  30

Thr Ile Val Gly Ser Ile Pro Ala Gly Asp Arg Phe Arg Ile Lys Trp
        35                  40                  45

Val Asp Ser Asp Tyr Leu Gly Trp Tyr Tyr Ile Glu Tyr Gln Gly Ile
    50                  55                  60

Thr Gly Tyr Val Ser Gln Asp Tyr Val Glu Lys Leu Gln Met Ala Thr
65                  70                  75                  80

Thr Cys Asn Val Asp Ser Val Leu Asn Val Arg Ala Glu Gly Asn Thr
                85                  90                  95

Ser Ser Asn Ile Val Ala Thr Ile Asn Pro Gly Glu Val Phe Arg Ile
            100                 105                 110

Asp Trp Val Asp Ser Asp Phe Ile Gly Trp Tyr Arg Ile Thr Thr Ala
        115                 120                 125

Asn Gly Ala Asn Gly Phe Val Lys Ser Asp Phe Val Lys Lys Leu
    130                 135                 140

<210> SEQ ID NO 9
<211> LENGTH: 143
<212> TYPE: PRT
<213> ORGANISM: Artificial Sequence
<220> FEATURE:
<223> OTHER INFORMATION: Chemically Synthesized

<400> SEQUENCE: 9

Glu Asp Phe Leu Lys Lys Asp Phe Thr Leu Glu Asn Ala Thr Thr Cys
1               5                   10                  15

Asn Val Asp Thr Glu Leu Asn Ile Arg Ala Lys Gly Thr Thr Gly Ala
            20                  25                  30

Thr Ile Val Gly Ser Ile Pro Ala Gly Asp Arg Phe Arg Ile Lys Trp
        35                  40                  45

Val Asp Ser Asp Tyr Leu Gly Trp Tyr Tyr Ile Glu Tyr Gln Gly Ile
    50                  55                  60

Thr Gly Tyr Val Ser Gln Asp Tyr Val Glu Lys Leu Gln Met Ala Thr
65                  70                  75                  80

Thr Cys Asn Val Asp Ser Val Leu Asn Val Arg Ala Glu Gly Asn Thr
                85                  90                  95

Ser Ser Asn Ile Val Ala Thr Ile Asn Pro Gly Glu Val Phe Arg Ile
            100                 105                 110

Asp Trp Val Asp Ser Asp Phe Ile Gly Trp Tyr Arg Ile Thr Thr Ala
        115                 120                 125

Asn Gly Ala Asn Gly Phe Val Lys Ser Asp Phe Val Lys Lys Leu
    130                 135                 140

<210> SEQ ID NO 10
<211> LENGTH: 351
<212> TYPE: PRT
<213> ORGANISM: Artificial Sequence
<220> FEATURE:
<223> OTHER INFORMATION: Chemically Synthesized

<400> SEQUENCE: 10
```

```
Met Met Val Arg Ile Val Leu Asp Ala Gly His Gly His Asp Pro
1               5                   10                  15

Gly Ala Val Ala Asn Gly Leu Arg Glu Lys Asp Leu Thr Leu Ala Ile
                20                  25                  30

Val Lys His Ile Gly Lys Met Leu Gly Glu Tyr Glu Gly Ala Glu Val
            35                  40                  45

His Tyr Thr Arg Thr Asp Asp Arg Phe Leu Glu Leu Ser Glu Arg Ala
        50                  55                  60

Ala Ile Ala Asn Lys Leu Lys Ala Asp Leu Leu Ile Ser Val His Ile
65                  70                  75                  80

Asn Ala Gly Gly Gly Thr Gly Phe Glu Ser Tyr Ile Tyr Asn Gly Asn
                85                  90                  95

Val Ser Pro Ala Thr Ile Ala Tyr Gln Asn Val Ile His Gln Glu Leu
            100                 105                 110

Met Lys Ala Ile Gly Asn Val Thr Asp Arg Gly Lys Lys Arg Ala Asn
        115                 120                 125

Tyr Ala Val Leu Arg Glu Thr Asn Met Pro Ala Ile Leu Thr Glu Asn
    130                 135                 140

Leu Phe Ile Asp Asn Ala Asn Asp Ala Ala Lys Leu Lys Ser Glu Gln
145                 150                 155                 160

Phe Leu Gln Gln Val Ala Tyr Gly His Val Gln Gly Ile Val Lys Ala
                165                 170                 175

Phe Gly Ser Ser Leu Asp Gly Ser Thr Gln Glu Ile Phe Ile Asn Gly
            180                 185                 190

Ala Ser Gln Lys Ala Thr Glu Asn Lys Ser Phe Phe Thr Asn Ala Arg
        195                 200                 205

Ala Lys Val Ala Leu Asp Pro Arg Ser Asn Pro Ser Asp Asn Tyr Lys
    210                 215                 220

Asp Leu Gly Glu Ile Tyr Ala Glu Glu Arg Ile Gln Val Leu Ala Glu
225                 230                 235                 240

Ile Cys Asp Arg Glu Asp Tyr Leu Pro Val Lys Tyr Trp Lys Asp Ala
                245                 250                 255

Ser Gly Cys Glu Ser Ser Lys Val Trp Val Asn Ala Asn Lys Asp Tyr
            260                 265                 270

Leu Glu Ile Asp Thr Asn Ala Arg Ser Phe Asn Ile Val Thr Glu Leu
        275                 280                 285

Asp Ala Arg Tyr Glu Pro Ser Val Asn Ser Lys Arg Met Gly Tyr Val
    290                 295                 300

Lys Asn Asn Glu Arg Leu Tyr Val His Arg Val Glu Gly Asp Tyr Val
305                 310                 315                 320

Leu Ala Thr Tyr Tyr Ala Gly Asn Gly Tyr Lys Thr Ala Trp Phe Thr
                325                 330                 335

Lys Glu Tyr Ile Ile Lys Asp Leu Glu His His His His His
            340                 345                 350
```

<210> SEQ ID NO 11
<211> LENGTH: 360
<212> TYPE: PRT
<213> ORGANISM: Artificial Sequence
<220> FEATURE:
<223> OTHER INFORMATION: Chemically Synthesized

<400> SEQUENCE: 11

```
Met Met Val Arg Ile Val Leu Asp Ala Gly His Gly Gly His Asp Pro
1               5                   10                  15
```

Gly Ala Val Ala Asn Gly Leu Arg Glu Lys Asp Leu Thr Leu Ala Ile
            20                  25                  30

Val Lys His Ile Gly Lys Met Leu Gly Glu Tyr Glu Gly Ala Glu Val
        35                  40                  45

His Tyr Thr Arg Thr Asp Asp Arg Phe Leu Glu Leu Ser Glu Arg Ala
    50                  55                  60

Ala Ile Ala Asn Lys Leu Lys Ala Asp Leu Leu Ile Ser Val His Ile
65                  70                  75                  80

Asn Ala Gly Gly Gly Thr Gly Phe Glu Ser Tyr Ile Tyr Asn Gly Asn
                85                  90                  95

Val Ser Pro Ala Thr Ile Ala Tyr Gln Asn Val Ile His Gln Glu Leu
            100                 105                 110

Met Lys Ala Ile Gly Asn Val Thr Asp Arg Gly Lys Lys Arg Ala Asn
        115                 120                 125

Tyr Ala Val Leu Arg Glu Thr Asn Met Pro Ala Ile Leu Thr Glu Asn
    130                 135                 140

Leu Phe Ile Asp Asn Ala Asn Asp Ala Ala Lys Leu Lys Ser Glu Gln
145                 150                 155                 160

Phe Leu Gln Gln Val Ala Tyr Gly His Val Gln Gly Ile Val Lys Ala
                165                 170                 175

Phe Gly Ser Ser Leu Glu Arg Met Leu Lys Ser Ile Asp Glu Asn Ile
            180                 185                 190

Val Asn Asp Thr Asp Thr Thr Asp Val Pro Ser Ser Asp Ser Asn
        195                 200                 205

Lys Lys Asp Phe Ser Thr Asn Ala Arg Ala Leu Val Ala Leu Asp Pro
    210                 215                 220

Arg Asp Asn Pro Ser Asp Asn Tyr Ser Asp Leu Gly Glu Ile Tyr Lys
225                 230                 235                 240

Asp Glu Arg Phe Arg Val Leu Ala Glu Val Cys Asp Lys Gly Asp Phe
                245                 250                 255

Leu Pro Ile Val Tyr Trp Lys Asp Ser Glu Gly Arg Glu Ser Gly Lys
            260                 265                 270

Val Trp Val Arg Ser Lys Gln Asp Tyr Met Met Ile Asp Thr Tyr His
        275                 280                 285

Lys Val Phe Asn Val Ile Thr Glu Leu Asp Ala Arg Tyr Glu Pro Ser
    290                 295                 300

Pro Asn Ser Ser Arg Met Gly Tyr Val Thr Asn Gly Glu Arg Leu Tyr
305                 310                 315                 320

Val His Arg Ile Glu Gly Asn Tyr Ala Leu Ala Thr Tyr Phe Ala Gly
                325                 330                 335

Asn Gly Tyr Lys Thr Ala Trp Phe Thr Lys Lys Tyr Ile Glu Lys Ile
            340                 345                 350

Val Glu His His His His His His
        355                 360

<210> SEQ ID NO 12
<211> LENGTH: 435
<212> TYPE: PRT
<213> ORGANISM: Artificial Sequence
<220> FEATURE:
<223> OTHER INFORMATION: Chemically Synthesized

<400> SEQUENCE: 12

Met Met Val Arg Ile Val Leu Asp Ala Gly His Gly Gly His Asp Pro
1               5                   10                  15

```
Gly Ala Val Ala Asn Gly Leu Arg Glu Lys Asp Leu Thr Leu Ala Ile
             20                  25                  30

Val Lys His Ile Gly Lys Met Leu Gly Glu Tyr Glu Gly Ala Glu Val
         35                  40                  45

His Tyr Thr Arg Thr Asp Asp Arg Phe Leu Glu Leu Ser Glu Arg Ala
     50                  55                  60

Ala Ile Ala Asn Lys Leu Lys Ala Asp Leu Leu Ile Ser Val His Ile
 65                  70                  75                  80

Asn Ala Gly Gly Gly Thr Gly Phe Glu Ser Tyr Ile Tyr Asn Gly Asn
                 85                  90                  95

Val Ser Pro Ala Thr Ile Ala Tyr Gln Asn Val Ile His Gln Glu Leu
            100                 105                 110

Met Lys Ala Ile Gly Asn Val Thr Asp Arg Gly Lys Lys Arg Ala Asn
        115                 120                 125

Tyr Ala Val Leu Arg Glu Thr Asn Met Pro Ala Ile Leu Thr Glu Asn
    130                 135                 140

Leu Phe Ile Asp Asn Ala Asn Asp Ala Ala Lys Leu Lys Ser Glu Gln
145                 150                 155                 160

Phe Leu Gln Gln Val Ala Tyr Gly His Val Gln Gly Ile Val Lys Ala
                165                 170                 175

Phe Gly Ser Ser Leu Asp Gly Ser Leu Ser Glu Phe Lys Asn Asn Ser
            180                 185                 190

Tyr Arg Pro Thr Gly Gly Ser Ser Glu Thr Val Val Ser Glu Asn Gly
        195                 200                 205

Phe Tyr Thr Ser Asn Glu Glu Arg Thr Asn Ala Thr Ile Val Gly Lys
    210                 215                 220

Gly Asp Ile Glu Val Leu Asp Glu Lys Gly Lys Val Ile Gln Gly Arg
225                 230                 235                 240

His Ile Ser Ser Leu Asp Arg Val Phe Val Leu Gly Ile Tyr Pro Ser
                245                 250                 255

Arg Asn His Ile Glu Leu Ile Tyr Pro Gly Lys Asp Glu Lys Tyr His
            260                 265                 270

Ala Tyr Ile Ser Ile Glu Asn Tyr Ser Arg Leu Ser Phe Asp Tyr His
        275                 280                 285

Met Gln Tyr Lys Asn Asp Asp Gly Val Thr Tyr Val Trp Asp Ser
    290                 295                 300

Lys Asn Val Asn Val Lys Asn His Asp Glu Glu Leu Gln Pro His Gln
305                 310                 315                 320

Lys Ala Ser Pro Met Tyr Arg Thr Asn Gly Trp Leu Arg Val Thr Phe
                325                 330                 335

Tyr Arg Ala Asp Gly Asn Pro Ser Asp Gly Tyr Val Arg Tyr Glu Gly
            340                 345                 350

Glu Gln Lys Glu Arg Phe Tyr Arg Lys Gly Lys Val Val Asn Val Arg
        355                 360                 365

Thr Ser Leu Thr Val Arg Ala Gly Ala Gly Thr Asn Tyr Ser Ala Ile
    370                 375                 380

Gly Ser Leu Asp Pro Asn Glu Asn Val Glu Ile Leu Glu Lys Thr Glu
385                 390                 395                 400

Gly Trp Tyr Tyr Ile Glu Tyr Asn Ala Arg Asn Glu Arg Lys Arg Gly
                405                 410                 415

Tyr Val Ser Lys Lys Tyr Ile Glu Ile Ile Gln Leu Glu His His His
            420                 425                 430

His His His
```

-continued

435

<210> SEQ ID NO 13
<211> LENGTH: 335
<212> TYPE: PRT
<213> ORGANISM: Artificial Sequence
<220> FEATURE:
<223> OTHER INFORMATION: Chemically Synthesized

<400> SEQUENCE: 13

Met Met Val Arg Ile Val Leu Asp Ala Gly His Gly Gly His Asp Pro
1               5                   10                  15

Gly Ala Val Ala Asn Gly Leu Arg Glu Lys Asp Leu Thr Leu Ala Ile
            20                  25                  30

Val Lys His Ile Gly Lys Met Leu Gly Glu Tyr Glu Gly Ala Glu Val
        35                  40                  45

His Tyr Thr Arg Thr Asp Asp Arg Phe Leu Glu Leu Ser Glu Arg Ala
    50                  55                  60

Ala Ile Ala Asn Lys Leu Lys Ala Asp Leu Leu Ile Ser Val His Ile
65                  70                  75                  80

Asn Ala Gly Gly Gly Thr Gly Phe Glu Ser Tyr Ile Tyr Asn Gly Asn
                85                  90                  95

Val Ser Pro Ala Thr Ile Ala Tyr Gln Asn Val Ile His Gln Glu Leu
            100                 105                 110

Met Lys Ala Ile Gly Asn Val Thr Asp Arg Gly Lys Lys Arg Ala Asn
        115                 120                 125

Tyr Ala Val Leu Arg Glu Thr Asn Met Pro Ala Ile Leu Thr Glu Asn
    130                 135                 140

Leu Phe Ile Asp Asn Ala Asn Asp Ala Ala Lys Leu Lys Ser Glu Gln
145                 150                 155                 160

Phe Leu Gln Gln Val Ala Tyr Gly His Val Gln Gly Ile Val Lys Ala
                165                 170                 175

Phe Gly Ser Ser Leu Asp Gly Ser Glu Asp Phe Leu Lys Lys Asp Phe
            180                 185                 190

Thr Leu Glu Asn Ala Thr Thr Cys Asn Val Asp Thr Glu Leu Asn Ile
        195                 200                 205

Arg Ala Lys Gly Thr Thr Gly Ala Thr Ile Val Gly Ser Ile Pro Ala
    210                 215                 220

Gly Asp Arg Phe Arg Ile Lys Trp Val Asp Ser Asp Tyr Leu Gly Trp
225                 230                 235                 240

Tyr Tyr Ile Glu Tyr Gln Gly Ile Thr Gly Tyr Val Ser Gln Asp Tyr
                245                 250                 255

Val Glu Lys Leu Gln Met Ala Thr Thr Cys Asn Val Asp Ser Val Leu
            260                 265                 270

Asn Val Arg Ala Glu Gly Asn Thr Ser Ser Asn Ile Val Ala Thr Ile
        275                 280                 285

Asn Pro Gly Glu Val Phe Arg Ile Asp Trp Val Asp Ser Asp Phe Ile
    290                 295                 300

Gly Trp Tyr Arg Ile Thr Thr Ala Asn Gly Ala Asn Gly Phe Val Lys
305                 310                 315                 320

Ser Asp Phe Val Lys Lys Leu Leu Glu His His His His His
                325                 330                 335

<210> SEQ ID NO 14
<211> LENGTH: 245
<212> TYPE: PRT

<213> ORGANISM: Artificial Sequence
<220> FEATURE:
<223> OTHER INFORMATION: Chemically Synthesized

<400> SEQUENCE: 14

```
Met Met Val Arg Ile Val Leu Asp Ala Gly His Gly His Asp Pro
1               5                   10                  15

Gly Ala Val Ala Asn Gly Leu Arg Glu Lys Asp Leu Thr Leu Ala Ile
                20                  25                  30

Val Lys His Ile Gly Lys Met Leu Gly Glu Tyr Glu Gly Ala Glu Val
            35                  40                  45

His Tyr Thr Arg Thr Asp Asp Arg Phe Leu Glu Leu Ser Glu Arg Ala
    50                  55                  60

Ala Ile Ala Asn Lys Leu Lys Ala Asp Leu Leu Ile Ser Val His Ile
65                  70                  75                  80

Asn Ala Gly Gly Gly Thr Gly Phe Glu Ser Tyr Ile Tyr Asn Gly Asn
                85                  90                  95

Val Ser Pro Ala Thr Ile Ala Tyr Gln Asn Val Ile His Gln Glu Leu
            100                 105                 110

Met Lys Ala Ile Gly Asn Val Thr Asp Arg Gly Lys Lys Arg Ala Asn
        115                 120                 125

Tyr Ala Val Leu Arg Glu Thr Asn Met Pro Ala Ile Leu Thr Glu Asn
130                 135                 140

Leu Phe Ile Asp Asn Ala Asn Asp Ala Ala Lys Leu Lys Ser Glu Gln
145                 150                 155                 160

Phe Leu Gln Gln Val Ala Tyr Gly His Val Gln Gly Ile Val Lys Ala
                165                 170                 175

Phe Gly Ser Ser Leu Asp Gly Ser Arg Tyr Leu Ala Asn Ala Ile Asp
            180                 185                 190

Pro Asn Ile Pro Leu Glu Lys Glu Gln Asp Tyr Tyr Arg Val Cys Val
        195                 200                 205

Gln Arg Phe Thr Asn Lys Glu Asp Ala Glu Lys Ala Gln Gln Arg Ile
    210                 215                 220

Ser Asn Glu Leu Gly Tyr Tyr Cys Phe Ala Glu Lys Ile Leu Glu His
225                 230                 235                 240

His His His His
                245
```

<210> SEQ ID NO 15
<211> LENGTH: 224
<212> TYPE: PRT
<213> ORGANISM: Artificial Sequence
<220> FEATURE:
<223> OTHER INFORMATION: Chemically Synthesized

<400> SEQUENCE: 15

```
Met Asn Asp Phe Ile Arg Glu Ile Ala Pro Phe Ala Gln Arg Ile Gln
1               5                   10                  15

Glu Lys Tyr Arg Ile Leu Ala Ser Leu Val Ile Ala Gln Ala Cys Leu
                20                  25                  30

Glu Ser Asn Phe Gly Gln Ser Gly Leu Ala Gln Lys Gly Lys Asn Leu
            35                  40                  45

Phe Gly Val Lys Gly Ser Tyr Asn Gly Gln Ser Val Thr Met Lys Thr
        50                  55                  60

Thr Glu Tyr Arg Gly Gly Lys Ala Tyr Gln Thr Asp Ala Ala Phe Arg
65                  70                  75                  80
```

```
Lys Tyr Pro Ser Trp Phe Glu Ser Leu Asp Asp Leu Ala Lys Leu Tyr
                85                  90                  95

Val Asn Gly Val Ser Trp Asp Arg Asn Lys Tyr Lys Pro Ile Ile Gly
            100                 105                 110

Glu Thr Asn Tyr Val Ile Ala Cys Lys Lys Val Gln Glu Cys Gly Tyr
        115                 120                 125

Ala Thr Asp Pro Asn Tyr Ala Ser Lys Leu Ile Ser Ile Ile Glu Lys
    130                 135                 140

Tyr Asp Leu Thr Lys Tyr Asp Lys Val Gly Asn Lys Lys Pro Val Lys
145                 150                 155                 160

Ser Ala Val Ala Ala Lys Lys Glu Lys Pro Gln Ile Tyr Ile Val Gln
                165                 170                 175

Lys Gly Asp Thr Leu Thr Ala Ile Ala Lys Arg Tyr Asn Thr Ser Val
            180                 185                 190

Gln Asn Leu Val Lys Leu Asn Asn Ile Lys Asn Pro Asp Leu Ile Leu
        195                 200                 205

Val Gly Gln Lys Leu Arg Val Lys Leu Glu His His His His His His
    210                 215                 220

<210> SEQ ID NO 16
<211> LENGTH: 164
<212> TYPE: PRT
<213> ORGANISM: Artificial Sequence
<220> FEATURE:
<223> OTHER INFORMATION: Chemically Synthesized

<400> SEQUENCE: 16

Met Asn Asp Phe Ile Arg Glu Ile Ala Pro Phe Ala Gln Arg Ile Gln
1               5                   10                  15

Glu Lys Tyr Arg Ile Leu Ala Ser Leu Val Ile Ala Gln Ala Cys Leu
            20                  25                  30

Glu Ser Asn Phe Gly Gln Ser Gly Leu Ala Gln Lys Gly Lys Asn Leu
        35                  40                  45

Phe Gly Val Lys Gly Ser Tyr Asn Gly Gln Ser Val Thr Met Lys Thr
    50                  55                  60

Thr Glu Tyr Arg Gly Gly Lys Ala Tyr Gln Thr Asp Ala Ala Phe Arg
65                  70                  75                  80

Lys Tyr Pro Ser Trp Phe Glu Ser Leu Asp Asp Leu Ala Lys Leu Tyr
                85                  90                  95

Val Asn Gly Val Ser Trp Asp Arg Asn Lys Tyr Lys Pro Ile Ile Gly
            100                 105                 110

Glu Thr Asn Tyr Val Ile Ala Cys Lys Lys Val Gln Glu Cys Gly Tyr
        115                 120                 125

Ala Thr Asp Pro Asn Tyr Ala Ser Lys Leu Ile Ser Ile Ile Glu Lys
    130                 135                 140

Tyr Asp Leu Thr Lys Tyr Asp Lys Val Gly Ser Ser Leu Glu His His
145                 150                 155                 160

His His His His

<210> SEQ ID NO 17
<211> LENGTH: 327
<212> TYPE: PRT
<213> ORGANISM: Artificial Sequence
<220> FEATURE:
<223> OTHER INFORMATION: Chemically Synthesized

<400> SEQUENCE: 17
```

Met Asn Asp Phe Ile Arg Glu Ile Ala Pro Phe Ala Gln Arg Ile Gln
1               5                   10                  15

Glu Lys Tyr Arg Ile Leu Ala Ser Leu Val Ile Ala Gln Ala Cys Leu
            20                  25                  30

Glu Ser Asn Phe Gly Gln Ser Gly Leu Ala Gln Lys Gly Lys Asn Leu
        35                  40                  45

Phe Gly Val Lys Gly Ser Tyr Asn Gly Gln Ser Val Thr Met Lys Thr
    50                  55                  60

Thr Glu Tyr Arg Gly Gly Lys Ala Tyr Gln Thr Asp Ala Ala Phe Arg
65                  70                  75                  80

Lys Tyr Pro Ser Trp Phe Glu Ser Leu Asp Asp Leu Ala Lys Leu Tyr
                85                  90                  95

Val Asn Gly Val Ser Trp Asp Arg Asn Lys Tyr Lys Pro Ile Ile Gly
            100                 105                 110

Glu Thr Asn Tyr Val Ile Ala Cys Lys Lys Val Gln Glu Cys Gly Tyr
        115                 120                 125

Ala Thr Asp Pro Asn Tyr Ala Ser Lys Leu Ile Ser Ile Glu Lys
    130                 135                 140

Tyr Asp Leu Thr Lys Tyr Asp Lys Val Gly Ser Ser Leu Asp Gly Ser
145                 150                 155                 160

Thr Gln Glu Ile Phe Ile Asn Gly Ala Ser Gln Lys Ala Thr Glu Asn
                165                 170                 175

Lys Ser Phe Phe Thr Asn Ala Arg Ala Lys Val Ala Leu Asp Pro Arg
            180                 185                 190

Ser Asn Pro Ser Asp Asn Tyr Lys Asp Leu Gly Glu Ile Tyr Ala Glu
        195                 200                 205

Glu Arg Ile Gln Val Leu Ala Glu Ile Cys Asp Arg Glu Asp Tyr Leu
    210                 215                 220

Pro Val Lys Tyr Trp Lys Asp Ala Ser Gly Cys Glu Ser Ser Lys Val
225                 230                 235                 240

Trp Val Asn Ala Asn Lys Asp Tyr Leu Glu Ile Asp Thr Asn Ala Arg
                245                 250                 255

Ser Phe Asn Ile Val Thr Glu Leu Asp Ala Arg Tyr Glu Pro Ser Val
            260                 265                 270

Asn Ser Lys Arg Met Gly Tyr Val Lys Asn Asn Glu Arg Leu Tyr Val
        275                 280                 285

His Arg Val Glu Gly Asp Tyr Val Leu Ala Thr Tyr Tyr Ala Gly Asn
    290                 295                 300

Gly Tyr Lys Thr Ala Trp Phe Thr Lys Glu Tyr Ile Ile Lys Asp Leu
305                 310                 315                 320

Glu His His His His His
                325

<210> SEQ ID NO 18
<211> LENGTH: 336
<212> TYPE: PRT
<213> ORGANISM: Artificial Sequence
<220> FEATURE:
<223> OTHER INFORMATION: Chemically Synthesized

<400> SEQUENCE: 18

Met Asn Asp Phe Ile Arg Glu Ile Ala Pro Phe Ala Gln Arg Ile Gln
1               5                   10                  15

Glu Lys Tyr Arg Ile Leu Ala Ser Leu Val Ile Ala Gln Ala Cys Leu
            20                  25                  30

Glu Ser Asn Phe Gly Gln Ser Gly Leu Ala Gln Lys Gly Lys Asn Leu
                35                  40                  45

Phe Gly Val Lys Gly Ser Tyr Asn Gly Gln Ser Val Thr Met Lys Thr
 50                  55                  60

Thr Glu Tyr Arg Gly Gly Lys Ala Tyr Gln Thr Asp Ala Ala Phe Arg
 65                  70                  75                  80

Lys Tyr Pro Ser Trp Phe Glu Ser Leu Asp Asp Leu Ala Lys Leu Tyr
                85                  90                  95

Val Asn Gly Val Ser Trp Asp Arg Asn Lys Tyr Lys Pro Ile Ile Gly
                100                 105                 110

Glu Thr Asn Tyr Val Ile Ala Cys Lys Lys Val Gln Glu Cys Gly Tyr
                115                 120                 125

Ala Thr Asp Pro Asn Tyr Ala Ser Lys Leu Ile Ser Ile Glu Lys
                130                 135                 140

Tyr Asp Leu Thr Lys Tyr Asp Lys Val Gly Ser Ser Leu Glu Arg Met
145                 150                 155                 160

Leu Lys Ser Ile Asp Glu Asn Ile Val Asn Asp Thr Asp Thr Thr Asp
                165                 170                 175

Val Pro Ser Ser Asp Asp Ser Asn Lys Lys Asp Phe Ser Thr Asn Ala
                180                 185                 190

Arg Ala Leu Val Ala Leu Asp Pro Arg Asp Asn Pro Ser Asp Asn Tyr
                195                 200                 205

Ser Asp Leu Gly Glu Ile Tyr Lys Asp Glu Arg Phe Arg Val Leu Ala
                210                 215                 220

Glu Val Cys Asp Lys Gly Asp Phe Leu Pro Ile Val Tyr Trp Lys Asp
225                 230                 235                 240

Ser Glu Gly Arg Glu Ser Gly Lys Val Trp Val Arg Ser Lys Gln Asp
                245                 250                 255

Tyr Met Met Ile Asp Thr Tyr His Lys Val Phe Asn Val Ile Thr Glu
                260                 265                 270

Leu Asp Ala Arg Tyr Glu Pro Ser Pro Asn Ser Ser Arg Met Gly Tyr
                275                 280                 285

Val Thr Asn Gly Glu Arg Leu Tyr Val His Arg Ile Glu Gly Asn Tyr
                290                 295                 300

Ala Leu Ala Thr Tyr Phe Ala Gly Asn Gly Tyr Lys Thr Ala Trp Phe
305                 310                 315                 320

Thr Lys Lys Tyr Ile Glu Lys Ile Val Glu His His His His His
                325                 330                 335

<210> SEQ ID NO 19
<211> LENGTH: 411
<212> TYPE: PRT
<213> ORGANISM: Artificial Sequence
<220> FEATURE:
<223> OTHER INFORMATION: Chemically Synthesized

<400> SEQUENCE: 19

Met Asn Asp Phe Ile Arg Glu Ile Ala Pro Phe Ala Gln Arg Ile Gln
1               5                   10                  15

Glu Lys Tyr Arg Ile Leu Ala Ser Leu Val Ile Ala Gln Ala Cys Leu
                20                  25                  30

Glu Ser Asn Phe Gly Gln Ser Gly Leu Ala Gln Lys Gly Lys Asn Leu
                35                  40                  45

Phe Gly Val Lys Gly Ser Tyr Asn Gly Gln Ser Val Thr Met Lys Thr
 50                  55                  60

Thr Glu Tyr Arg Gly Gly Lys Ala Tyr Gln Thr Asp Ala Ala Phe Arg
 65                  70                  75                  80

Lys Tyr Pro Ser Trp Phe Glu Ser Leu Asp Asp Leu Ala Lys Leu Tyr
                 85                  90                  95

Val Asn Gly Val Ser Trp Asp Arg Asn Lys Tyr Lys Pro Ile Ile Gly
            100                 105                 110

Glu Thr Asn Tyr Val Ile Ala Cys Lys Lys Val Gln Glu Cys Gly Tyr
        115                 120                 125

Ala Thr Asp Pro Asn Tyr Ala Ser Lys Leu Ile Ser Ile Ile Glu Lys
130                 135                 140

Tyr Asp Leu Thr Lys Tyr Asp Lys Val Gly Ser Ser Leu Asp Gly Ser
145                 150                 155                 160

Leu Ser Glu Phe Lys Asn Asn Ser Tyr Arg Pro Thr Gly Gly Ser Ser
                165                 170                 175

Glu Thr Val Val Ser Glu Asn Gly Phe Tyr Thr Ser Asn Glu Glu Arg
            180                 185                 190

Thr Asn Ala Thr Ile Val Gly Lys Gly Asp Ile Glu Val Leu Asp Glu
        195                 200                 205

Lys Gly Lys Val Ile Gln Gly Arg His Ile Ser Ser Leu Asp Arg Val
210                 215                 220

Phe Val Leu Gly Ile Tyr Pro Ser Arg Asn His Ile Glu Leu Ile Tyr
225                 230                 235                 240

Pro Gly Lys Asp Glu Lys Tyr His Ala Tyr Ile Ser Ile Glu Asn Tyr
                245                 250                 255

Ser Arg Leu Ser Phe Asp Tyr His Met Gln Tyr Lys Asn Asp Asp Gly
            260                 265                 270

Val Thr Tyr Val Trp Trp Asp Ser Lys Asn Val Asn Val Lys Asn His
        275                 280                 285

Asp Glu Glu Leu Gln Pro His Gln Lys Ala Ser Pro Met Tyr Arg Thr
290                 295                 300

Asn Gly Trp Leu Arg Val Thr Phe Tyr Arg Ala Asp Gly Asn Pro Ser
305                 310                 315                 320

Asp Gly Tyr Val Arg Tyr Glu Gly Glu Gln Lys Glu Arg Phe Tyr Arg
                325                 330                 335

Lys Gly Lys Val Val Asn Val Arg Thr Ser Leu Thr Val Arg Ala Gly
            340                 345                 350

Ala Gly Thr Asn Tyr Ser Ala Ile Gly Ser Leu Asp Pro Asn Glu Asn
        355                 360                 365

Val Glu Ile Leu Glu Lys Thr Glu Gly Trp Tyr Tyr Ile Glu Tyr Asn
370                 375                 380

Ala Arg Asn Glu Arg Lys Arg Gly Tyr Val Ser Lys Lys Tyr Ile Glu
385                 390                 395                 400

Ile Ile Gln Leu Glu His His His His His His
                405                 410

<210> SEQ ID NO 20
<211> LENGTH: 311
<212> TYPE: PRT
<213> ORGANISM: Artificial Sequence
<220> FEATURE:
<223> OTHER INFORMATION: Chemically Synthesized

<400> SEQUENCE: 20

Met Asn Asp Phe Ile Arg Glu Ile Ala Pro Phe Ala Gln Arg Ile Gln
1               5                   10                  15

```
Glu Lys Tyr Arg Ile Leu Ala Ser Leu Val Ile Ala Gln Ala Cys Leu
            20                  25                  30

Glu Ser Asn Phe Gly Gln Ser Gly Leu Ala Gln Lys Gly Lys Asn Leu
            35                  40                  45

Phe Gly Val Lys Gly Ser Tyr Asn Gly Gln Ser Val Thr Met Lys Thr
50                  55                  60

Thr Glu Tyr Arg Gly Gly Lys Ala Tyr Gln Thr Asp Ala Ala Phe Arg
65                  70                  75                  80

Lys Tyr Pro Ser Trp Phe Glu Ser Leu Asp Asp Leu Ala Lys Leu Tyr
                85                  90                  95

Val Asn Gly Val Ser Trp Asp Arg Asn Lys Tyr Lys Pro Ile Ile Gly
            100                 105                 110

Glu Thr Asn Tyr Val Ile Ala Cys Lys Lys Val Gln Glu Cys Gly Tyr
            115                 120                 125

Ala Thr Asp Pro Asn Tyr Ala Ser Lys Leu Ile Ser Ile Glu Lys
130                 135                 140

Tyr Asp Leu Thr Lys Tyr Asp Lys Val Gly Ser Ser Leu Asp Gly Ser
145                 150                 155                 160

Glu Asp Phe Leu Lys Lys Asp Phe Thr Leu Glu Asn Ala Thr Thr Cys
                165                 170                 175

Asn Val Asp Thr Glu Leu Asn Ile Arg Ala Lys Gly Thr Thr Gly Ala
            180                 185                 190

Thr Ile Val Gly Ser Ile Pro Ala Gly Asp Arg Phe Arg Ile Lys Trp
            195                 200                 205

Val Asp Ser Asp Tyr Leu Gly Trp Tyr Tyr Ile Glu Tyr Gln Gly Ile
210                 215                 220

Thr Gly Tyr Val Ser Gln Asp Tyr Val Glu Lys Leu Gln Met Ala Thr
225                 230                 235                 240

Thr Cys Asn Val Asp Ser Val Leu Asn Val Arg Ala Glu Gly Asn Thr
                245                 250                 255

Ser Ser Asn Ile Val Ala Thr Ile Asn Pro Gly Glu Val Phe Arg Ile
            260                 265                 270

Asp Trp Val Asp Ser Asp Phe Ile Gly Trp Tyr Arg Ile Thr Thr Ala
            275                 280                 285

Asn Gly Ala Asn Gly Phe Val Lys Ser Asp Phe Val Lys Lys Leu Leu
290                 295                 300

Glu His His His His His
305                 310
```

<210> SEQ ID NO 21
<211> LENGTH: 221
<212> TYPE: PRT
<213> ORGANISM: Artificial Sequence
<220> FEATURE:
<223> OTHER INFORMATION: Chemically Synthesized

<400> SEQUENCE: 21

```
Met Asn Asp Phe Ile Arg Glu Ile Ala Pro Phe Ala Gln Arg Ile Gln
1               5                   10                  15

Glu Lys Tyr Arg Ile Leu Ala Ser Leu Val Ile Ala Gln Ala Cys Leu
            20                  25                  30

Glu Ser Asn Phe Gly Gln Ser Gly Leu Ala Gln Lys Gly Lys Asn Leu
            35                  40                  45

Phe Gly Val Lys Gly Ser Tyr Asn Gly Gln Ser Val Thr Met Lys Thr
50                  55                  60
```

```
Thr Glu Tyr Arg Gly Gly Lys Ala Tyr Gln Thr Asp Ala Ala Phe Arg
 65                  70                  75                  80

Lys Tyr Pro Ser Trp Phe Glu Ser Leu Asp Asp Leu Ala Lys Leu Tyr
                 85                  90                  95

Val Asn Gly Val Ser Trp Asp Arg Asn Lys Tyr Lys Pro Ile Ile Gly
            100                 105                 110

Glu Thr Asn Tyr Val Ile Ala Cys Lys Lys Val Gln Glu Cys Gly Tyr
        115                 120                 125

Ala Thr Asp Pro Asn Tyr Ala Ser Lys Leu Ile Ser Ile Ile Glu Lys
    130                 135                 140

Tyr Asp Leu Thr Lys Tyr Asp Lys Val Gly Ser Ser Leu Asp Gly Ser
145                 150                 155                 160

Arg Tyr Leu Ala Asn Ala Ile Asp Pro Asn Ile Pro Leu Glu Lys Glu
                165                 170                 175

Gln Asp Tyr Tyr Arg Val Cys Val Gln Arg Phe Thr Asn Lys Glu Asp
            180                 185                 190

Ala Glu Lys Ala Gln Gln Arg Ile Ser Asn Glu Leu Gly Tyr Tyr Cys
        195                 200                 205

Phe Ala Glu Lys Ile Leu Glu His His His His His His
210                 215                 220
```

<210> SEQ ID NO 22
<211> LENGTH: 241
<212> TYPE: PRT
<213> ORGANISM: Artificial Sequence
<220> FEATURE:
<223> OTHER INFORMATION: Chemically Synthesized

<400> SEQUENCE: 22

```
Met Lys Lys Ile Phe Trp Asp Lys Gly His Gly Gly Ser Asp Pro Gly
  1               5                  10                  15

Ala Val Ala Asn Gly Leu Gln Glu Lys Asn Leu Thr His Lys Ile Val
             20                  25                  30

Glu Tyr Ala Thr Asp Tyr Leu Ala Ala His Tyr Glu Gly Phe Thr Gln
         35                  40                  45

Arg Val Ser Arg Glu Gly Asp Gln Ser Leu Thr Leu Asp Gln Arg Ala
 50                  55                  60

Asp Met Ala Asn Lys Trp Gly Ala Asp Val Phe Val Ser Val His Ile
 65                  70                  75                  80

Asn Ala Gly Lys Gly Thr Gly Phe Glu Ile Tyr Val His Pro Asn Ala
                 85                  90                  95

Ser Pro Gln Ser Ile Ala Leu Gln Asn Val Leu His Gly Glu Ile Leu
            100                 105                 110

Ser Ala Met Arg Gln Phe Gly Asn Ile Thr Asp Arg Gly Lys Lys Arg
        115                 120                 125

Ala Asn Tyr Ala Val Leu Arg Glu Thr Lys Met Pro Ala Val Leu Thr
    130                 135                 140

Glu Asn Leu Phe Ile Asp Ser Asn Asp Ala Lys His Leu Lys Asn Glu
145                 150                 155                 160

Ala Phe Leu Lys Ala Val Gly Glu Ala His Ala Arg Gly Val Ala Lys
                165                 170                 175

Phe Leu Gly Leu Lys Glu Lys Gln Lys Ala Gln Pro Glu Ala Lys Pro
            180                 185                 190

Gln Gln Lys Pro Ser Asp Lys Lys Leu Tyr Arg Val Gln Val Gly Ala
        195                 200                 205
```

```
Phe Ala Asp Arg Glu Asn Ala Glu Arg Leu Ala Glu Glu Leu Lys Arg
            210                 215                 220
Lys Gly Tyr Pro Val Tyr Ile Thr Asp Leu Glu His His His His His
225                 230                 235                 240
His
```

<210> SEQ ID NO 23
<211> LENGTH: 189
<212> TYPE: PRT
<213> ORGANISM: Artificial Sequence
<220> FEATURE:
<223> OTHER INFORMATION: Chemically Synthesized

<400> SEQUENCE: 23

```
Met Lys Lys Ile Phe Trp Asp Lys Gly His Gly Gly Ser Asp Pro Gly
1               5                   10                  15
Ala Val Ala Asn Gly Leu Gln Glu Lys Asn Leu Thr His Lys Ile Val
                20                  25                  30
Glu Tyr Ala Thr Asp Tyr Leu Ala Ala His Tyr Glu Gly Phe Thr Gln
            35                  40                  45
Arg Val Ser Arg Glu Gly Asp Gln Ser Leu Thr Leu Asp Gln Arg Ala
        50                  55                  60
Asp Met Ala Asn Lys Trp Gly Ala Asp Val Phe Val Ser Val His Ile
65                  70                  75                  80
Asn Ala Gly Lys Gly Thr Gly Phe Glu Ile Tyr Val His Pro Asn Ala
                85                  90                  95
Ser Pro Gln Ser Ile Ala Leu Gln Asn Val Leu His Gly Glu Ile Leu
            100                 105                 110
Ser Ala Met Arg Gln Phe Gly Asn Ile Thr Asp Arg Gly Lys Lys Arg
        115                 120                 125
Ala Asn Tyr Ala Val Leu Arg Glu Thr Lys Met Pro Ala Val Leu Thr
130                 135                 140
Glu Asn Leu Phe Ile Asp Ser Asn Asp Ala Lys His Leu Lys Asn Glu
145                 150                 155                 160
Ala Phe Leu Lys Ala Val Gly Glu Ala His Ala Arg Gly Val Ala Lys
                165                 170                 175
Phe Leu Gly Ser Ser Leu Glu His His His His His His
            180                 185
```

<210> SEQ ID NO 24
<211> LENGTH: 352
<212> TYPE: PRT
<213> ORGANISM: Artificial Sequence
<220> FEATURE:
<223> OTHER INFORMATION: Chemically Synthesized

<400> SEQUENCE: 24

```
Met Lys Lys Ile Phe Trp Asp Lys Gly His Gly Gly Ser Asp Pro Gly
1               5                   10                  15
Ala Val Ala Asn Gly Leu Gln Glu Lys Asn Leu Thr His Lys Ile Val
                20                  25                  30
Glu Tyr Ala Thr Asp Tyr Leu Ala Ala His Tyr Glu Gly Phe Thr Gln
            35                  40                  45
Arg Val Ser Arg Glu Gly Asp Gln Ser Leu Thr Leu Asp Gln Arg Ala
        50                  55                  60
Asp Met Ala Asn Lys Trp Gly Ala Asp Val Phe Val Ser Val His Ile
65                  70                  75                  80
```

Asn Ala Gly Lys Gly Thr Gly Phe Glu Ile Tyr Val His Pro Asn Ala
                85                  90                  95

Ser Pro Gln Ser Ile Ala Leu Gln Asn Val Leu His Gly Glu Ile Leu
            100                 105                 110

Ser Ala Met Arg Gln Phe Gly Asn Ile Thr Asp Arg Gly Lys Lys Arg
            115                 120                 125

Ala Asn Tyr Ala Val Leu Arg Glu Thr Lys Met Pro Ala Val Leu Thr
130                 135                 140

Glu Asn Leu Phe Ile Asp Ser Asn Asp Ala Lys His Leu Lys Asn Glu
145                 150                 155                 160

Ala Phe Leu Lys Ala Val Gly Glu Ala His Ala Arg Gly Val Ala Lys
                165                 170                 175

Phe Leu Gly Ser Ser Leu Asp Gly Ser Thr Gln Glu Ile Phe Ile Asn
            180                 185                 190

Gly Ala Ser Gln Lys Ala Thr Glu Asn Lys Ser Phe Phe Thr Asn Ala
            195                 200                 205

Arg Ala Lys Val Ala Leu Asp Pro Arg Ser Asn Pro Ser Asp Asn Tyr
210                 215                 220

Lys Asp Leu Gly Glu Ile Tyr Ala Glu Arg Ile Gln Val Leu Ala
225                 230                 235                 240

Glu Ile Cys Asp Arg Glu Asp Tyr Leu Pro Val Lys Tyr Trp Lys Asp
                245                 250                 255

Ala Ser Gly Cys Glu Ser Ser Lys Val Trp Val Asn Ala Asn Lys Asp
            260                 265                 270

Tyr Leu Glu Ile Asp Thr Asn Ala Arg Ser Phe Asn Ile Val Thr Glu
            275                 280                 285

Leu Asp Ala Arg Tyr Glu Pro Ser Val Asn Ser Lys Arg Met Gly Tyr
290                 295                 300

Val Lys Asn Asn Glu Arg Leu Tyr Val His Arg Val Glu Gly Asp Tyr
305                 310                 315                 320

Val Leu Ala Thr Tyr Tyr Ala Gly Asn Gly Tyr Lys Thr Ala Trp Phe
                325                 330                 335

Thr Lys Glu Tyr Ile Ile Lys Asp Leu Glu His His His His His His
            340                 345                 350

<210> SEQ ID NO 25
<211> LENGTH: 361
<212> TYPE: PRT
<213> ORGANISM: Artificial Sequence
<220> FEATURE:
<223> OTHER INFORMATION: Chemically Synthesized

<400> SEQUENCE: 25

Met Lys Lys Ile Phe Trp Asp Lys Gly His Gly Gly Ser Asp Pro Gly
1               5                   10                  15

Ala Val Ala Asn Gly Leu Gln Glu Lys Asn Leu Thr His Lys Ile Val
            20                  25                  30

Glu Tyr Ala Thr Asp Tyr Leu Ala His Tyr Glu Gly Phe Thr Gln
                35                  40                  45

Arg Val Ser Arg Glu Gly Asp Gln Ser Leu Thr Leu Asp Gln Arg Ala
50                  55                  60

Asp Met Ala Asn Lys Trp Gly Ala Asp Val Phe Val Ser Val His Ile
65                  70                  75                  80

Asn Ala Gly Lys Gly Thr Gly Phe Glu Ile Tyr Val His Pro Asn Ala
                85                  90                  95

Ser Pro Gln Ser Ile Ala Leu Gln Asn Val Leu His Gly Glu Ile Leu
            100                 105                 110

Ser Ala Met Arg Gln Phe Gly Asn Ile Thr Asp Arg Gly Lys Lys Arg
        115                 120                 125

Ala Asn Tyr Ala Val Leu Arg Glu Thr Lys Met Pro Ala Val Leu Thr
    130                 135                 140

Glu Asn Leu Phe Ile Asp Ser Asn Asp Ala Lys His Leu Lys Asn Glu
145                 150                 155                 160

Ala Phe Leu Lys Ala Val Gly Glu Ala His Ala Arg Gly Val Ala Lys
                165                 170                 175

Phe Leu Gly Ser Ser Leu Glu Arg Met Leu Lys Ser Ile Asp Glu Asn
            180                 185                 190

Ile Val Asn Asp Thr Asp Thr Thr Asp Val Pro Ser Ser Asp Asp Ser
        195                 200                 205

Asn Lys Lys Asp Phe Ser Thr Asn Ala Arg Ala Leu Val Ala Leu Asp
    210                 215                 220

Pro Arg Asp Asn Pro Ser Asp Asn Tyr Ser Asp Leu Gly Glu Ile Tyr
225                 230                 235                 240

Lys Asp Glu Arg Phe Arg Val Leu Ala Glu Val Cys Asp Lys Gly Asp
                245                 250                 255

Phe Leu Pro Ile Val Tyr Trp Lys Asp Ser Glu Gly Arg Glu Ser Gly
            260                 265                 270

Lys Val Trp Val Arg Ser Lys Gln Asp Tyr Met Met Ile Asp Thr Tyr
        275                 280                 285

His Lys Val Phe Asn Val Ile Thr Glu Leu Asp Ala Arg Tyr Glu Pro
    290                 295                 300

Ser Pro Asn Ser Ser Arg Met Gly Tyr Val Thr Asn Gly Glu Arg Leu
305                 310                 315                 320

Tyr Val His Arg Ile Glu Gly Asn Tyr Ala Leu Ala Thr Tyr Phe Ala
                325                 330                 335

Gly Asn Gly Tyr Lys Thr Ala Trp Phe Thr Lys Tyr Ile Glu Lys
            340                 345                 350

Ile Val Glu His His His His His His
        355                 360

<210> SEQ ID NO 26
<211> LENGTH: 436
<212> TYPE: PRT
<213> ORGANISM: Artificial Sequence
<220> FEATURE:
<223> OTHER INFORMATION: Chemically Synthesized

<400> SEQUENCE: 26

Met Lys Lys Ile Phe Trp Asp Lys Gly His Gly Gly Ser Asp Pro Gly
1               5                   10                  15

Ala Val Ala Asn Gly Leu Gln Glu Lys Asn Leu Thr His Lys Ile Val
            20                  25                  30

Glu Tyr Ala Thr Asp Tyr Leu Ala His Tyr Glu Gly Phe Thr Gln
        35                  40                  45

Arg Val Ser Arg Glu Gly Asp Gln Ser Leu Thr Leu Asp Gln Arg Ala
    50                  55                  60

Asp Met Ala Asn Lys Trp Gly Ala Asp Val Phe Val Ser Val His Ile
65                  70                  75                  80

Asn Ala Gly Lys Gly Thr Gly Phe Glu Ile Tyr Val His Pro Asn Ala
                85                  90                  95

```
Ser Pro Gln Ser Ile Ala Leu Gln Asn Val Leu His Gly Glu Ile Leu
            100                 105                 110

Ser Ala Met Arg Gln Phe Gly Asn Ile Thr Asp Arg Gly Lys Lys Arg
            115                 120                 125

Ala Asn Tyr Ala Val Leu Arg Glu Thr Lys Met Pro Ala Val Leu Thr
        130                 135                 140

Glu Asn Leu Phe Ile Asp Ser Asn Asp Ala Lys His Leu Lys Asn Glu
145                 150                 155                 160

Ala Phe Leu Lys Ala Val Gly Glu Ala His Ala Arg Gly Val Ala Lys
                165                 170                 175

Phe Leu Gly Ser Ser Leu Asp Gly Ser Leu Ser Glu Phe Lys Asn Asn
            180                 185                 190

Ser Tyr Arg Pro Thr Gly Gly Ser Glu Thr Val Val Ser Glu Asn
            195                 200                 205

Gly Phe Tyr Thr Ser Asn Glu Glu Arg Thr Asn Ala Thr Ile Val Gly
        210                 215                 220

Lys Gly Asp Ile Glu Val Leu Asp Glu Lys Gly Lys Val Ile Gln Gly
225                 230                 235                 240

Arg His Ile Ser Ser Leu Asp Arg Val Phe Val Leu Gly Ile Tyr Pro
                245                 250                 255

Ser Arg Asn His Ile Glu Leu Ile Tyr Pro Gly Lys Asp Glu Lys Tyr
            260                 265                 270

His Ala Tyr Ile Ser Ile Glu Asn Tyr Ser Arg Leu Ser Phe Asp Tyr
        275                 280                 285

His Met Gln Tyr Lys Asn Asp Asp Gly Val Thr Tyr Val Trp Trp Asp
290                 295                 300

Ser Lys Asn Val Asn Val Lys Asn His Asp Glu Leu Gln Pro His
                310                 315                 320

Gln Lys Ala Ser Pro Met Tyr Arg Thr Asn Gly Trp Leu Arg Val Thr
            325                 330                 335

Phe Tyr Arg Ala Asp Gly Asn Pro Ser Asp Gly Tyr Val Arg Tyr Glu
        340                 345                 350

Gly Glu Gln Lys Glu Arg Phe Tyr Arg Lys Gly Lys Val Val Asn Val
            355                 360                 365

Arg Thr Ser Leu Thr Val Arg Ala Gly Ala Gly Thr Asn Tyr Ser Ala
370                 375                 380

Ile Gly Ser Leu Asp Pro Asn Glu Asn Val Glu Ile Leu Glu Lys Thr
385                 390                 395                 400

Glu Gly Trp Tyr Tyr Ile Glu Tyr Asn Ala Arg Asn Glu Arg Lys Arg
            405                 410                 415

Gly Tyr Val Ser Lys Lys Tyr Ile Glu Ile Gln Leu Glu His His
        420                 425                 430

His His His His
        435

<210> SEQ ID NO 27
<211> LENGTH: 336
<212> TYPE: PRT
<213> ORGANISM: Artificial Sequence
<220> FEATURE:
<223> OTHER INFORMATION: Chemically Synthesized

<400> SEQUENCE: 27

Met Lys Lys Ile Phe Trp Asp Lys Gly His Gly Gly Ser Asp Pro Gly
1               5                   10                  15
```

Ala Val Ala Asn Gly Leu Gln Glu Lys Asn Leu Thr His Lys Ile Val
            20                  25                  30

Glu Tyr Ala Thr Asp Tyr Leu Ala Ala His Tyr Glu Gly Phe Thr Gln
        35                  40                  45

Arg Val Ser Arg Glu Gly Asp Gln Ser Leu Thr Leu Asp Gln Arg Ala
    50                  55                  60

Asp Met Ala Asn Lys Trp Gly Ala Asp Val Phe Val Ser Val His Ile
65                  70                  75                  80

Asn Ala Gly Lys Gly Thr Gly Phe Glu Ile Tyr Val His Pro Asn Ala
                85                  90                  95

Ser Pro Gln Ser Ile Ala Leu Gln Asn Val Leu His Gly Glu Ile Leu
            100                 105                 110

Ser Ala Met Arg Gln Phe Gly Asn Ile Thr Asp Arg Gly Lys Lys Arg
        115                 120                 125

Ala Asn Tyr Ala Val Leu Arg Glu Thr Lys Met Pro Ala Val Leu Thr
    130                 135                 140

Glu Asn Leu Phe Ile Asp Ser Asn Asp Ala Lys His Leu Lys Asn Glu
145                 150                 155                 160

Ala Phe Leu Lys Ala Val Gly Glu Ala His Ala Arg Gly Val Ala Lys
                165                 170                 175

Phe Leu Gly Ser Ser Leu Asp Gly Ser Glu Asp Phe Leu Lys Lys Asp
            180                 185                 190

Phe Thr Leu Glu Asn Ala Thr Thr Cys Asn Val Asp Thr Glu Leu Asn
        195                 200                 205

Ile Arg Ala Lys Gly Thr Thr Gly Ala Thr Ile Val Gly Ser Ile Pro
    210                 215                 220

Ala Gly Asp Arg Phe Arg Ile Lys Trp Val Asp Ser Asp Tyr Leu Gly
225                 230                 235                 240

Trp Tyr Tyr Ile Glu Tyr Gln Gly Ile Thr Gly Tyr Val Ser Gln Asp
                245                 250                 255

Tyr Val Glu Lys Leu Gln Met Ala Thr Thr Cys Asn Val Asp Ser Val
            260                 265                 270

Leu Asn Val Arg Ala Glu Gly Asn Thr Ser Ser Asn Ile Val Ala Thr
        275                 280                 285

Ile Asn Pro Gly Glu Val Phe Arg Ile Asp Trp Val Asp Ser Asp Phe
    290                 295                 300

Ile Gly Trp Tyr Arg Ile Thr Thr Ala Asn Gly Ala Asn Gly Phe Val
305                 310                 315                 320

Lys Ser Asp Phe Val Lys Lys Leu Leu Glu His His His His His His
                325                 330                 335

<210> SEQ ID NO 28
<211> LENGTH: 242
<212> TYPE: PRT
<213> ORGANISM: Artificial Sequence
<220> FEATURE:
<223> OTHER INFORMATION: Chemically Synthesized

<400> SEQUENCE: 28

Met Gly Met Lys Lys Ile Phe Trp Asp Lys Gly His Gly Gly Ser Asp
1               5                   10                  15

Pro Gly Ala Val Ala Asn Gly Leu Gln Glu Lys Asn Leu Thr His Lys
            20                  25                  30

Ile Val Glu Tyr Ala Thr Asp Tyr Leu Ala Ala His Tyr Glu Gly Phe
        35                  40                  45

-continued

```
Thr Gln Arg Val Ser Arg Glu Gly Asp Gln Ser Leu Thr Leu Asp Gln
    50                  55                  60

Arg Ala Asp Met Ala Asn Lys Trp Gly Ala Asp Val Phe Val Ser Val
65                  70                  75                  80

His Ile Asn Ala Gly Lys Gly Thr Gly Phe Glu Ile Tyr Val His Pro
                85                  90                  95

Asn Ala Ser Pro Gln Ser Ile Ala Leu Gln Asn Val Leu His Gly Glu
            100                 105                 110

Ile Leu Ser Ala Met Arg Gln Phe Gly Asn Ile Thr Asp Arg Gly Lys
            115                 120                 125

Lys Arg Ala Asn Tyr Ala Val Leu Arg Glu Thr Lys Met Pro Ala Val
    130                 135                 140

Leu Thr Glu Asn Leu Phe Ile Asp Ser Asn Asp Ala Lys His Leu Lys
145                 150                 155                 160

Asn Glu Ala Phe Leu Lys Ala Val Gly Glu Ala His Ala Arg Gly Val
                165                 170                 175

Ala Lys Phe Leu Gly Arg Tyr Leu Ala Asn Ala Ile Asp Pro Asn Ile
            180                 185                 190

Pro Leu Glu Lys Glu Gln Asp Tyr Tyr Arg Val Cys Val Gln Arg Phe
    195                 200                 205

Thr Asn Lys Glu Asp Ala Glu Lys Ala Gln Gln Arg Ile Ser Asn Glu
    210                 215                 220

Leu Gly Tyr Tyr Cys Phe Ala Glu Lys Ile Leu Glu His His His His
225                 230                 235                 240

His His
```

THERMOPHILE PEPTIDOGLYCAN HYDROLASE FUSION PROTEINS AND USES THEREOF

FIELD OF THE INVENTION

This invention relates to recombinant polynucleotides encoding chimeric lysins derived from fusing the DNA sequences from one of three thermophile endolysin catalytic domains with one of several cell wall binding domains. The chimeric lysins are capable of killing several strains of *Clostridium perfringens*, but not other Gram-positive bacteria.

SEQUENCE LISTING

The instant application contains a Sequence Listing which has been submitted in ASCII format and is hereby incorporated by reference in its entirety. The ASCII file was created on Apr. 4, 2019, is named SequenceListing, and has 75 kilobytes.

BACKGROUND OF THE INVENTION

*Clostridium perfringens* (*C. perfringens*) is a Gram-positive, spore forming, anaerobic bacterium commonly present in the intestines of humans and animals. Spores of the pathogen can persist in soil, feces, or the environment. The bacterium causes many severe infections of animals and humans, including food poisoning, gas gangrene, and necrotic enteritis. The bacterium causes non-foodborne gastrointestinal infections in humans.

In chickens, *C. perfringens* is believed a causative agent of necrotic enteritis, the most common and financially devastating bacterial disease in modern broiler flocks. Although the clinical illness is usually very short, mortality in an unprotected poultry flock can be devastating. Indeed, often the only sign of necrotic enteritis in a flock is a sudden increase in mortality. In addition to increased mortality, necrotic enteritis may present as birds with depression, ruffled feathers, and dark diarrhea. Typically, the disease persists in a flock for between about 5-10 days, with mortality between about 2-50%.

Necrotic enteritis is typically controlled by antimicrobial drugs administered at prophylactic doses either in water or in feed. However, there is increasing public opposition to the use of antibiotics in animal feeds. In the European Union (EU) antimicrobial growth promoters (AGP) were banned from animal feeds on 1 Jan. 2006 (Regulation 1831/2003/EC) because of concerns about the increasing prevalence of antibiotic resistances among bacteria. In 2015, the state of California passed Senate Bill No. 27, Chapter 758, banning the routine use of antibiotics in livestock. In 2015, McDonald's, the fast-food corporation, announced that it was going to use antibiotic-free chickens and in 2017 enacted the Global Vision for Antibiotic Stewardship in Food Animals (VAS). These events are likely precursors to further bans of the use of antibiotics in animal-feed. Without traditional antibiotics for the prevention of necrotic enteritis and other diseases caused by *C. perfringens*, such diseases could potentially become a far greater problem for the livestock industry.

Therefore, there is a need in the art for alternatives to traditional antibiotics which are effective in preventing and treating disease caused by *C. perfringens*, especially *C. perfringens* that affect poultry and are highly refractory to resistance development.

SUMMARY OF THE INVENTION

Provided herein are chimeric recombinant lysins comprising at least one thermophile endolysin catalytic domain selected from the group consisting of the N-terminal catalytic domain from PlyGspY412, PlyGspY4, and PlyGVE2; at least one cell wall binding domain selected from the group consisting of the cell wall binding domain from *C. perfringens* endolysins PlyCP10, PlyCP18, PlyCP33, PlyCP41, and PlyCP26; optionally comprising a linker between the catalytic domain and the cell wall binding domain; and optionally comprising a polyhistidine tag.

In an embodiment, the invention relates to a polynucleotide encoding a chimeric recombinant lysin, wherein the chimeric recombinant lysin comprises at least a first nucleic acid molecule encoding a thermophile endolysin catalytic domain selected from the group consisting of the N-terminal catalytic domain from PlyGspY412, PlyGspY4, and PlyGVE2; at least a second nucleic acid molecule encoding a cell wall binding domain selected from the group consisting of the cell wall binding domain from *C. perfringens* endolysins PlyCP10, PlyCP18, PlyCP33, PlyCP41, and PlyCP26; optionally comprising a third nucleic acid molecule encoding a linker between the catalytic domain and the cell wall binding domain; and optionally comprising a fourth nucleic acid molecule encoding a polyhistidine tag. In some embodiments of the invention the polynucleotide encoding the chimeric recombinant lysin comprises a fourth nucleic acid molecule encoding a polyhistidine tag. In some embodiments of the invention, the fourth nucleic acid molecule encodes a polyhistidine tag having an amino acid sequence selected from the group consisting of SEQ ID NO: 1 and SEQ ID NO: 2. In some embodiments of the invention, the polyhistidine tag encoded by the fourth nucleic acid molecule has the amino acid sequence of SEQ ID NO: 1. In some embodiments of the invention, the polyhistidine tag encoded by the fourth nucleic acid molecule has the amino acid sequence of SEQ ID NO: 2.

In an embodiment of the invention, the thermophile endolysin catalytic domain in the chimeric recombinant lysin is from PlyGspY412 and the cell wall binding domain in the chimeric recombinant lysin is selected from the group consisting of the cell wall binding domain from *C. perfringens* endolysins PlyCP10, PlyCP18, PlyCP33, PlyCP41, and PlyCP26F. In some embodiments of the invention, the catalytic domain is from PlyGspY412 and the cell wall binding domain is from PlyCP33. In some embodiments of the invention, the catalytic domain is from PlyGspY412 and the cell wall binding domain is from PlyCP41.

In some embodiments of the invention, the thermophile endolysin catalytic domain in the chimeric recombinant lysin is from PlyGspY4 and the cell wall binding domain in the chimeric recombinant lysin is selected from the group consisting of the cell wall binding domain from *C. perfringens* endolysins PlyCP10, PlyCP18, PlyCP33, PlyCP41, and PlyCP26F. In some embodiments of the invention, the catalytic domain is from PlyGspY4 and the cell wall binding domain is from PlyCP33. In some embodiments of the invention, the catalytic domain is from PlyGspY4 and the cell wall binding domain is from PlyCP41.

In some embodiments of the invention the thermophile endolysin catalytic domain in the chimeric recombinant lysin is from PlyGVE2 and the cell wall binding domain in the recombinant chimeric lysin is selected from the group consisting of the cell wall binding domain from *C. perfringens* endolysins PlyCP10, PlyCP18, PlyCP33, PlyCP41, and PlyCP26; and the chimeric recombinant lysin does not have the amino acid sequence of SEQ ID NO: 28. In some embodiments of the invention, the catalytic domain is from PlyGVE2 and the cell wall binding domain is from PlyCP33. In some embodiments of the invention, the catalytic domain is from PlyGVE2 and the cell wall binding domain is from PlyCP41.

In an embodiment of the invention, the amino acid sequence of the thermophile endolysin catalytic domain is selected from the group consisting of SEQ ID NO: 4; SEQ ID NO: 16; and SEQ ID N: 23; the amino acid sequence of the cell wall binding domain is selected from the group consisting of SEQ ID NO: 5; SEQ ID NO: 6; SEQ ID NO: 7; SEQ ID NO: 8; and SEQ ID NO: 9; and the chimeric recombinant lysin does not have the amino acid sequence set forth in SEQ ID NO: 28.

In an embodiment of the invention, the chimeric recombinant lysin has an amino acid sequence selected from the group consisting of SEQ ID NO: 10; SEQ ID NO: 11; SEQ ID NO: 12; SEQ ID NO: 13; SEQ ID NO: 14; SEQ ID NO: 17; SEQ ID NO: 18; SEQ ID NO: 19; SEQ ID NO: 20; SEQ ID NO: 21; SEQ ID NO: 24; SEQ ID NO: 25; SEQ ID NO: 26; and SEQ ID NO: 27.

In an embodiment, the invention relates to a nucleic acid construct comprising a promoter operably linked to a polynucleotide encoding a chimeric recombinant lysin, wherein the chimeric recombinant lysin comprises at least a first nucleic acid molecule encoding a thermophile endolysin catalytic domain selected from the group consisting of the N-terminal catalytic domain from PlyGspY412, PlyGspY4, and PlyGVE2; at least a second nucleic acid molecule encoding a cell wall binding domain selected from the group consisting of the cell wall binding domain from *C. perfringens* endolysins PlyCP10, PlyCP18, PlyCP33, PlyCP41, and PlyCP26; optionally comprising a third nucleic acid molecule encoding a linker between the catalytic domain and the cell wall binding domain; and optionally comprising a fourth nucleic acid molecule encoding a polyhistidine tag. In some embodiments of the invention the polynucleotide encoding the chimeric recombinant lysin comprises a fourth nucleic acid molecule encoding a polyhistidine tag.

In some embodiments, the invention relates to a vector comprising a polynucleotide encoding a chimeric recombinant lysin, wherein the chimeric recombinant lysin comprises at least a first nucleic acid molecule encoding a thermophile endolysin catalytic domain selected from the group consisting of the N-terminal catalytic domain from PlyGspY412, PlyGspY4, and PlyGVE2; at least a second nucleic acid molecule encoding a cell wall binding domain selected from the group consisting of the cell wall binding domain from *C. perfringens* endolysins PlyCP10, PlyCP18, PlyCP33, PlyCP41, and PlyCP26; optionally containing a third nucleic acid molecule encoding a linker between the catalytic domain and the cell wall binding domain; and optionally containing a fourth nucleic acid molecule encoding a polyhistidine tag. In some embodiments of the invention the polynucleotide encoding the chimeric recombinant lysin comprises a fourth nucleic acid molecule encoding a polyhistidine tag.

In an embodiment, the invention relates to a host cell comprising a polynucleotide encoding a chimeric recombinant lysin of the invention. In some embodiments of the invention the polynucleotide encoding the chimeric recombinant lysin comprises a fourth nucleic acid molecule encoding a polyhistidine tag. In some embodiments of the invention, the host cell comprising a polynucleotide encoding a chimeric recombinant lysin is selected from a bacterial cell, a fungal cell, a plant cell, and a mammalian cell.

In an embodiment, the invention relates to a chimeric recombinant lysin polypeptide comprising at least one thermophile endolysin catalytic domain selected from the group consisting of the N-terminal catalytic domain from PlyGspY412, PlyGspY4, and PlyGVE2; at least one cell wall binding domain selected from the group consisting of *C. perfringens* endolysins PlyCP10, PlyCP18, PlyCP33, PlyCP41, and PlyCP26; optionally comprising a linker between the catalytic domain and the cell wall binding domain; and optionally comprising a polyhistidine tag.

In an embodiment, the invention relates to a polypeptide comprising a thermophile endolysin catalytic domain having the amino acid sequence selected from the group consisting of SEQ ID NO: 4; SEQ ID NO: 16; and SEQ ID N: 23; a cell wall binding domain having the amino acid sequence selected from the group consisting of SEQ ID NO: 5; SEQ ID NO: 6; SEQ ID NO: 7; SEQ ID NO: 8; and SEQ ID NO: 9; and the chimeric recombinant lysin does not have the amino acid sequence set forth in SEQ ID NO: 28.

In an embodiment of the invention, the chimeric recombinant lysin polypeptide has an amino acid sequence selected from the group consisting of SEQ ID NO: 10; SEQ ID NO: 11; SEQ ID NO: 12; SEQ ID NO: 13; SEQ ID NO: 14; SEQ ID NO: 17; SEQ ID NO: 18; SEQ ID NO: 19; SEQ ID NO: 20; SEQ ID NO: 21; SEQ ID NO: 24; SEQ ID NO: 25; and SEQ ID NO: 26.

In an embodiment, the invention relates to a host cell comprising a polypeptide comprising a thermophile endolysin catalytic domain having the amino acid sequence selected from the group consisting of SEQ ID NO: 4; SEQ ID NO: 16; and SEQ ID N: 23; a cell wall binding domain having the amino acid sequence selected from the group consisting of SEQ ID NO: 5; SEQ ID NO: 6; SEQ ID NO: 7; SEQ ID NO: 8; and SEQ ID NO: 9; where the chimeric recombinant lysin does not have the amino acid sequence set forth in SEQ ID NO: 28. In some embodiments of the invention, the host cell is selected from a bacterial cell, a fungal cell, a plant cell, and a mammalian cell.

In an embodiment, the invention relates to a composition comprising a polypeptide comprising a thermophile endolysin catalytic domain having the amino acid sequence selected from the group consisting of SEQ ID NO: 4; SEQ ID NO: 16; and SEQ ID NO: 23; a cell wall binding domain having the amino acid sequence selected from the group consisting of SEQ ID NO: 5; SEQ ID NO: 6; SEQ ID NO: 7; SEQ ID NO: 8; and SEQ ID NO: 9; where the chimeric recombinant lysin does not have the amino acid sequence set forth in SEQ ID NO: 28. In some embodiments of the invention, the composition comprises a pharmaceutically acceptable carrier.

In an embodiment, the invention relates to the use of a composition comprising a polypeptide comprising a thermophile endolysin catalytic domain having the amino acid sequence selected from the group consisting of SEQ ID NO: 4; SEQ ID NO: 16; and SEQ ID NO: 23; a cell wall binding domain having the amino acid sequence selected from the group consisting of SEQ ID NO: 5; SEQ ID NO: 6; SEQ ID NO: 7; SEQ ID NO: 8; and SEQ ID NO: 9; where the chimeric recombinant lysin does not have the amino acid sequence set forth in SEQ ID NO: 28 for the treatment of infection and disease caused by *Clostridium perfringens*. In some embodiments of the invention, the composition is formulated for oral administration. In some embodiments of the invention the composition is in the form of animal feed.

In an embodiment, the invention relates to a method of treating infection and disease caused by *C. perfringens* in an individual in need thereof, comprising administering to said individual an effective dose of a composition comprising a polypeptide comprising a thermophile endolysin catalytic domain having the amino acid sequence selected from the group consisting of SEQ ID NO: 4; SEQ ID NO: 16; and SEQ ID NO: 23; a cell wall binding domain having the amino acid sequence selected from the group consisting of SEQ ID NO: 5; SEQ ID NO: 6; SEQ ID NO: 7; SEQ ID NO: 8; and SEQ ID NO: 9; where the chimeric recombinant lysin does not have the amino acid sequence set forth in SEQ ID NO: 28. In some embodiments of the invention, the infection and disease caused by *C. perfringens* is necrotic enteritis. In some embodiments of the invention, the individual in need of treatment for an infection or disease caused by *C. perfringens* is selected from the group consisting of chicken, pig, and newborn calf. In some embodiments of the invention, the infection and disease caused by *C. perfringens* is gas gangrene.

In some embodiments, the invention relates to a method of preparing a polypeptide comprising a thermophile endolysin catalytic domain having the amino acid sequence selected from the group consisting of SEQ ID NO: 4; SEQ ID NO: 16; and SEQ ID N: 23; a cell wall binding domain having the amino acid sequence selected from the group consisting of SEQ ID NO: 5; SEQ ID NO: 6; SEQ ID NO: 7; SEQ ID NO: 8; and SEQ ID NO: 9; where the chimeric recombinant lysin does not have the amino acid sequence set forth in SEQ ID NO: 28, the method comprising cultivating a host cell in a suitable medium, under conditions that allow expression of the polypeptide, and preparing the polypeptide. Optionally, the invention relates to further recovering the polypeptide.

BRIEF DESCRIPTION OF THE DRAWINGS

FIG. 1 depicts a schematic of the thermophile endolysin PlyGspY412; the thermophile endolysin catalytic domain Y412$_{CAT}$; and the thermophile-derived chimeric recombinant lysins Y412$_{CAT}$-CP10$_{CWB}$; Y412$_{CAT}$-CP18$_{CWB}$; Y412$_{CAT}$CP33$_{CWB}$; Y412$_{CAT}$-CP41$_{CWB}$; and Y412$_{CAT}$-CP26F$_{CWB}$. PlyGspY412 and its amidase catalytic domain (Y412$_{CAT}$) are indicated by vertical stripes (▥); the cell wall binding domains from PlyCP10 (CP10$_{CWB}$); PlyCP18 (CP18$_{CWB}$); PlyCP33 (CP33$_{CWB}$); PlyCP41 (CP41$_{CWB}$); and PlyCP26F (CP26F$_{CWB}$) are indicated by a white solid fill (□); the polyhistidine tags are indicated by a black solid fill (■). The names of the constructs are indicated to the left of the figure, and the number of amino acids in each construct are indicated to the right of the figure.

FIG. 2 depicts a schematic of the thermophile endolysin PlyGspY4; the thermophile endolysin glucosaminidase catalytic domain Y4$_{CAT}$; and the thermophile-derived chimeric recombinant lysins Y4$_{CAT}$-CP10$_{CWB}$; Y4$_{CAT}$-CP18$_{CWB}$; Y4$_{CAT}$-CP33$_{CWB}$; Y4$_{CAT}$-CP41$_{CWB}$ Y4$_{CAT}$-CP26F$_{CWB}$ PlyGspY4 and its glucosaminidase catalytic domain (Y4$_{CAT}$) are indicated by vertical stripes (▥); the cell wall binding domains CP10$_{CWB}$; CP18$_{CWB}$; CP33$_{CWB}$; CP41$_{CWB}$; and CP26F$_{CWB}$ are indicated by a white solid fill (□); the polyhistidine tags are indicated by a black solid fill (■). The names of the constructs are indicated to the left of the figure, and the number of amino acids in each construct are indicated to the right of the figure.

FIG. 3 depicts a schematic of the thermophile endolysin PlyGVE2; the thermophile endolysin amidase catalytic domain GVE2$_{CAT}$; and the thermophile-derived chimeric recombinant lysins GVE2$_{CAT}$-CP10$_{CWB}$; GVE2$_{CAT}$-CP18$_{CWB}$; GVE2$_{CAT}$-CP33$_{CWB}$; GVE2$_{CAT}$-CP41$_{CWB}$; and GVE2$_{CAT}$-CP26F$_{CWB}$. PlyGVE2 and its amidase catalytic domain (GVE2$_{CAT}$) are indicated by horizontal stripes (▤); the cell wall binding domains CP10$_{CWB}$; CP18$_{CWB}$; CP33$_{CWB}$; CP41$_{CWB}$; and CP26F$_{CWB}$ are indicated by a white solid fill (□); the polyhistidine tags are indicated by a black solid fill (■). The names of the constructs are indicated to the left of the figure, and the number of amino acids in each construct are indicated to the right of the figure.

FIG. 4 depicts a graph of the turbidity reduction obtained for Y412$_{CAT}$ and its fusions at room temperature. The Y axis shows the normalized reduction in the optical density (DO) and the X axis shows the time in seconds. Duplicate data runs are shown for each lysin and buffer control. The material in each run is indicated to the right of the figure.

FIG. 5 depicts a graph of the turbidity reduction obtained for Y4$_{CAT}$ and its fusions at room temperature. The Y axis shows the normalized reduction in the optical density (DO) and the X axis shows the time in seconds. Duplicate data runs are shown for each lysin and buffer control. The material in each run is indicated to the right of the figure.

FIG. 6 depicts a graph of the turbidity reduction obtained for GVE2$_{CAT}$ and its fusions at room temperature. The Y axis shows the normalized reduction in the optical density (DO) and the X axis shows the time in seconds. Duplicate data runs are shown for each lysin and buffer control. The material in each run is indicated to the right of the figure.

FIG. 7A and FIG. 7B depict graphs of the turbidity reduction obtained after incubating the proteins for 15 minutes at different temperatures (two samples per temperature) prior to the assay. FIG. 7A: PlyGve2CP$_{CWB}$; FIG. 7B: Gve2$_{CAT}$-CP18$_{CWB}$. The Y axis shows the normalized reduction in the optical density (OD) and the X axis shows the time in seconds. The incubation temperatures are indicated by each set of data.

FIG. 8 depicts a graph of the thermostability of PlyGspY412 (Y412$_{CAT}$-) derived fusion proteins compared to mesophile derived PlyCP18. Bars are as follows: Y412$_{CAT}$-CP10$_{CWB}$, downward diagonal stripes (▧); Y412$_{CAT}$-CP18$_{CWB}$, zig-zag lines (▩); Y412$_{CAT}$-CP33$_{CWB}$, upward diagonal stripes (▨); Y412$_{CAT}$-CP41$_{CWB}$, checker board (▦); Y412$_{CAT}$-CP26F$_{CWB}$, horizontal stripes (▤); and PlyCP18, solid black bar (■). The Y axis shows the rate of reduction in the optical density in milliOD600/min. The X axis shows the temperature of the heat treatment in degrees Celsius.

FIG. 9 depicts a graph of the thermostability of PlyGspY4 (Y4$_{CAT}$) derived fusion proteins compared to mesophile derived PlyCP18. Bars are as follows: Y4$_{CAT}$-CP10$_{CWB}$, downward diagonal stripes (▧); Y4$_{CAT}$-CP18$_{CWB}$, zig-zag lines (▩); Y4$_{CAT}$-CP33$_{CWB}$, upward diagonal stripes (▨); Y4$_{CAT}$-CP41$_{CWB}$, checker board (▦); Y4$_{CAT}$-CP26F$_{CWB}$, horizontal stripes (▤); and PlyCP18, solid black bar (■). The Y axis shows the rate of reduction in the optical density in milliOD600/min. The X axis shows the temperature of the heat treatment in degrees Celsius.

FIG. 10 depicts a graph of the thermostability of PlyGVE2 (GVE2$_{CAT}$-) derived fusion proteins compared to mesophile derived PlyCP18. Bars are as follows: GVE2$_{CAT}$-CP10$_{CWB}$, downward diagonal stripes (▧); GVE2$_{CAT}$-CP18CWB, zig-zag lines (▩); GVE2$_{CAT}$-CP33$_{CWB}$, upward diagonal stripes (▨); GVE2$_{CAT}$-CP41$_{CWB}$, checker board (▦); GVE2$_{CAT}$-CP26F$_{CWB}$, horizontal stripes (▤); and PlyCP18, solid black bar (■). The Y axis shows the rate of reduction in the optical density in milliOD600/min. The X axis shows the temperature of the heat treatment in degrees Celsius.

BRIEF DESCRIPTION OF THE SEQUENCE LISTING

Table 1 below lists the described polynucleotides and their Sequence Identifiers.

TABLE 1

| Identifier | type | Description |
| --- | --- | --- |
| SEQ ID NO: 1 | aa | Polyhistidine Tag 1 |
| SEQ ID NO: 2 | aa | Polyhistidine Tag 2 |
| SEQ ID NO: 3 | aa | PlyGspY412 |
| SEQ ID NO: 4 | aa | $Y412_{CAT}$ |
| SEQ ID NO: 5 | aa | $CP10_{CWB}$ |
| SEQ ID NO: 6 | aa | $CP18_{CWB}$ |
| SEQ ID NO: 7 | aa | $CP33_{CWB}$ |
| SEQ ID NO: 8 | aa | $CP41_{CWB}$ |
| SEQ ID NO: 9 | aa | $CP26F_{CWB}$ |
| SEQ ID NO: 10 | aa | $Y412_{CAT}\text{-}CP10_{CWB}$ |
| SEQ ID NO: 11 | aa | $Y412_{CAT}\text{-}CP18_{CWB}$ |
| SEQ ID NO: 12 | aa | $Y412_{CAT}\text{-}CP33_{CWB}$ |
| SEQ ID NO: 13 | aa | $Y412_{CAT}\text{-}CP41_{CWB}$ |
| SEQ ID NO: 14 | aa | $Y412_{CAT}\text{-}CP26F_{CWB}$ |
| SEQ ID NO: 15 | aa | PlyGspY4 |
| SEQ ID NO: 16 | aa | $Y4_{CAT}$ |
| SEQ ID NO: 17 | aa | $Y4_{CAT}\text{-}CP10_{CWB}$ |
| SEQ ID NO: 18 | aa | $Y4_{CAT}\text{-}CP18_{CWB}$ |
| SEQ ID NO: 19 | aa | $Y4_{CAT}\text{-}CP33_{CWB}$ |
| SEQ ID NO: 20 | aa | $Y4_{CAT}\text{-}CP41_{CWB}$ |
| SEQ ID NO: 21 | aa | $Y4_{CAT}\text{-}CP26F_{CWB}$ |
| SEQ ID NO: 22 | aa | PlyGVE2 |
| SEQ ID NO: 23 | aa | $GVE2_{CAT}$ |
| SEQ ID NO: 24 | aa | $GVE2_{CAT}\text{-}CP10_{CWB}$ |
| SEQ ID NO: 25 | aa | $GVE2_{CAT}\text{-}CP18_{CWB}$ |
| SEQ ID NO: 26 | aa | $GVE2_{CAT}\text{-}CP33_{CWB}$ |
| SEQ ID NO: 27 | aa | $GVE2_{CAT}\text{-}CP41_{CWB}$ |
| SEQ ID NO: 28 | aa | $GVE2_{CAT}\text{-}CP26F_{CWB}$ ($PlyGVE2Cp_{CWB}$) |

DETAILED DESCRIPTION

This invention relates to chimeric recombinant lysins derived from fusing thermophile endolysin catalytic domains with different endolysin cell wall binding domains.

The catalytic domains named here as $Y412_{CAT}$ and $Y4_{CAT}$ are derived from endolysins from *Geobacillus* species Y412MC61 and Y4.1MC1. The catalytic domain named here as $GVE2_{CAT}$ is derived from the deep-sea temperate thermophilic siphovirus GVE2. The Conserved Domains Search program of the National Center for Biotechnology Information (NCBI) predicted that the catalytic domains for $Y412_{CAT}$ and $GVE2_{CAT}$ are L-alanine-amidases, and the catalytic domain for $Y4_{CAT}$ is an endo-beta-N-acetylglucosaminidase (a glycosidase). These domains degrade the peptidoglycan which comprises the main structural component of the cell wall of *C. perfringens*.

By homology screening, the catalytic domain of PlyGspY4 is predicted to be a glucosaminidase domain, and the catalytic domains of PlyGVE2 and PlyGspY412, are predicted have L-alanine amidase domain homology. Thus, the PlyGspY4 catalytic domain is predicted to cleave a different peptidoglycan bond than the catalytic domains of PlyGVE2 and PlyGspY412. However, there is evidence in the literature that identification of PGH lytic domain by homology screening is not always reliable as demonstrated by the 2638a staphylococcal endolysin endopeptidase domain (Abaev I et al. 2013, "*Staphylococcal phage 2638A endolysin is lytic for Staphylococcus aureus and harbors an inter-lytic-domain secondary translational start site*," Appl. Microbiol. Biotechnol. 97(8): 3449-3456). Chimeric recombinant lysins comprising $Y4_{CAT}$ displayed overall reduced activity compared to the other chimeric recombinant lysins tested. The recombinant lysins $Y4_{CAT}\text{-}CP10_{CWB}$, $Y4_{CAT}\text{-}CP18_{CWB}$, $Y4_{CAT}\text{-}CP33$, and $Y4_{CAT}\text{-}CP41$ all had activity against the five *C. perfringens* strains tested. $Y4_{CAT}\text{-}CP26F_{CWB}$ had poor lytic activity against Cp509, and was not active against the other four *C. perfringens* strains (lysin at 0.005 mg/mL). Of the chimeric recombinant lysins comprising $Y4_{CAT}$, only $Y4_{CAT}\text{-}CP41_{CWB}$ displayed substantial activity after heat treatment at 60° C. However, the value of these chimeric recombinant lysins must also take into account their ability to cleave a different bond in the peptidoglycan than the other lysins presented here. No glucosaminidase-containing endolysins were found in a 2011 study which analyzed nine public *C. perfringens* genomes, and found 45 endolysin-like enzymes (Schmitz et al. 2011, "*Lytic enzyme discovery through multigenomic sequence analysis in Clostridium perfringens*," Appl. Microbiol. Biotechnol. 89(6):1783-1795). This suggests the $Y4_{CAT}$ fusions may represent a rare lytic activity against *C. perfringens* strains.

The ability of the thermophile-derived catalytic domains from PlyGspY412, PlyGspY4, and PlyGVE2 to lyse *C. perfringens* strains when fused to a variety of cell wall binding domains from *C. perfringens* endolysins suggests that they would also be active when fused to other binding domains that target of different species of Gram-positive bacteria.

The DNA sequences of the catalytic domains from PlyGspY412, PlyGspY4, and PlyGVE2 were fused to the coding sequences of cell wall binding ($_{CWB}$) domains from *C. perfringens* endolysins: PlyCP18, PlyCP10, PlyCP33, PlyCP41, and PlyCP26F. The resulting chimeric recombinant lysins have the capacity to kill several strains of *C. perfringens*.

Alternatives to traditional antibiotics effective in preventing and treating disease caused by *C. perfringens*, and highly refractory to resistance development are needed. Specifically, methods of preventing and treating disease caused by *C. perfringens* that affect poultry are needed.

The terms "effective amount" and "effective dose" refer to an amount of an active ingredient sufficient to achieve a desired effect without causing an undesirable side effect. In some cases, it may be necessary to achieve a balance between obtaining a desired effect and limiting the severity of an undesired effect. It will be appreciated that the amount of active ingredient used will vary depending upon the type of active ingredient and the intended use of the polynucleotides of the present invention. The desired effect may be objective (i.e., measurable by some test or marker) or subjective (i.e., subject gives an indication of or feels an effect). Effective doses will vary depending on route and method of administration, as well as the possibility of co-usage with other agents.

*C. perfringens* is normally found in the intestines of humans and animals. It is also a common cause of food poisoning when ingested in sufficient numbers. Illness results from toxin production in the intestines. Common food sources of *C. perfringens* poisoning include meat and poultry dishes, soups, and sauces, such as gravy. *C. perfringens* is also known to cause other diseases, such as infections of the skin and deeper tissues. This is known as "clostridial myonecrosis" or "gas gangrene," which can occur when deep wounds are contaminated with foreign objects containing the bacteria.

Clostridial enteritis affects intestinal health in broiler flocks and may cause considerable losses. It is caused by *Clostridium perfringens* and is found all over the world.

Fighting the disease is a continuing challenge for the poultry sector. Preventive actions using dedicated products are a valuable solution to maintain healthy gut flora.

Sheep enterotoxaemia caused by *C. perfringens* is well documented. Different strains of *C. perfringens* are responsible for several clinical syndromes, including lamb dysentery, pulpy kidney, and struck (enterotoxaemia in adult sheep that causes sudden death). Prevention is straightforward, through vaccination of the lambs, and of ewes during pregnancy. Cattle enterotoxaemia is an acute or peracute syndrome with a case fatality rate close to 100 percent, associated with an uncontrolled multiplication of *C. perfringens* in the small intestine with an overproduction of toxins. These toxins act both locally and systemically and may cause death within a few minutes to a few hours.

Bacterio-lytic proteins like endolysins have great potential for controlling bacteria. Bacteriophage are viruses that infect bacteria. Some bacteriophage integrate their genome into the genome of their bacteria host and become dormant prophages. Endolysins are encoded in bacteriophage (and prophage) genomes and are used by the bacteriophage to lyse their host cells, in order to cause the release of replicated bacteriophage particles. Endolysins cause this lysis by degrading the peptidoglycan of the cell wall of the bacteria, resulting in cells bursting open; cell lysis. The site of action is external to the pathogen, and thus avoids many of the intracellular drug resistance mechanisms e.g. efflux pumps. Also, the phage and host have co-evolved, allowing the phage endolysin to target sites in the cell wall that are difficult for the bacterium to mutate. Thus, it is believed that phage endolysins are highly refractory to resistance development. This characteristic makes endolysins a good source of anti-bacterial agents against Gram-positive bacteria, like *C. perfringens*.

Bacterial peptidoglycan has a complex structure composed of a sugar backbone of alternating units of N-acetyl glucosamine (GlcNac) and N-acetyl muramic acid (MurNac) residues, cross-linked by oligopeptide attachments at the MurNac. Endolysins have evolved a modular design to deal with this complexity. One protein can harbor multiple domains, each with a different peptidoglycan digestion activity. Three classes of endolysin domains have been identified thus far: endopeptidase, glycosidase, and amidase. Each has been localized to short protein domains of about 100 to 200 amino acids. Any one of these domains is sufficient to lyse the bacterial target cell. The glycosidases cleave between N-acetyl glucosame (GlcNac) and N-acetyl muramine acid (MurNac). Amidases cleave between MurNac and the first amino acid of the peptide. Endopeptidases cleave between peptide bonds. Gram-positive cell walls have at least 10 to 20 layers of peptidoglycan compared to 1 to 3 layers for Gram-negative cells (Scheffers D J and Pinho M G, 2005, "*Bacterial cell wall synthesis: new insights from localization studies*," Microbiol. Mol. Biol. Rev. 69(4):585-607).

For decades, commercial animal feed has incorporated different antibiotics, like avoparcin (similar to vancomycin), tetracycline, and bacitracin, as antibiotic growth promotants (AGP) (Dibner J J and Richards J D, 2005, "*Antibiotic growth promoters in agriculture: history and mode of action*," Poult. Sci. 84: 634-643). A U.S. Food & Drug Administration (FDA) report on antibiotic sales for food-animal use stated that 14 million kilograms of antibiotics were sold in 2016 in the United States, and this was a decrease of 10% from the previous year. Of these antibiotics, over 8 million kilograms fell into the category of important for human medical therapy (FDA, 2017, "2016 *SUMMARY REPORT on Antimicrobials Sold or Distributed for Use in Food-Producing Animals*," Center for Veterinary Medicine, U.S. Food & Drug Administration, 2017: 1-67). As a consequence of increasing concerns about antibiotic resistant bacteria and changing consumer preferences, this practice is losing favor and AGPs are banned in both Europe and California (Castanon J I R, 2007, "*History of the use of antibiotic as growth promoters in European poultry feeds*," Poult. Sci. 86: 2466-2471; Millet S and Maertens L, 2011, "*The European ban on antibiotic growth promoters in animal feed: from challenges to opportunities*," Vet. J. 187:143-144; California-Legislature, 2015, "*Livestock: Use of Antimicrobial Drugs*," Division 7, Chapter 4.5 California Legislature (ed.) California Legislative Information Website). A similar ban of AGP use for the entire United States is possible within the next few years. In a proactive effort, various commercial companies like McDonalds and Purdue Farms have voluntarily eliminated animals raised on antibiotics from their meat sources.

The world-wide scourge of antibiotic-resistant bacteria has prompted the search for alternatives to commonly used antibiotics, especially new agents that are refractory to resistance development. One alternative to antibiotics is bacteriophage (viruses that infect bacteria) and bacteriophage lytic enzymes (Nelson D C et al., 2012, "Endolysins as Antimicrobials," Adv. Virus Res. 83: 299-365; Schmelcher, Donovan and Loessner 2012). Bacteriophage, or phage, use enzymes called endolysins to degrade the peptidoglycan that is a major structural component of the bacterial cell wall, resulting in osmolysis and release of the mature viral particles. Endolysins, or phage lysins, when applied externally to the uninfected gram-positive phage host bacteria, cause osmolysis. Studies attempting to elicit resistance to different endolysins (Pal, PlyG and LysH5) failed to achieve resistance (Loeffler, Nelson and Fischetti 2001; Schuch, Nelson and Fischetti 2002; Rodriguez-Rubio et al. 2013). It is generally believed that because phage lysins are specific to the species (or genera) of bacteria that the bacteriophage can infect and have coevolved with the bacteria that it would be difficult for the bacteria to develop resistance to endolysins (Ajuebor et al. 2016).

Antibiotic resistance among pathogens is believed to develop, in part, through the use of broad range antibiotics, which affect not only the target pathogen, but can also select for resistance in other bacteria (e.g. commensals). The use of a highly specific antimicrobial would target fewer species, and thus is less likely to contribute to the broad range resistance development now apparent with commonly used broad range antibiotics. Bacteriophage endolysins are uniquely specific to their host (or closely related species); bacteriophage and bacterial hosts have co-evolved. It is difficult to prove that resistance cannot develop to endolysins, but to date, none has been reported and this fact alone makes this product a candidate for addition to the battery of antimicrobials available to both veterinary medicine and the clinician. If resistant strains are not produced, this would be an important antimicrobial for use and efficacy.

Without traditional antibiotics for the prevention of animal diseases caused by *C. perfringens*, such diseases could potentially become a far greater problem. Removal of antibiotics will dictate the need for alternative antimicrobials in order to achieve the same high level of food-animal production achieved with AGPs. Thus, to manage the upsurge of drug resistant pathogenic bacteria, there is a need for new specific antimicrobial treatments. Reagents developed specifically for the relevant genera, species, or substrains of concern would function as effective tools for controlling economically important diseases and therefore are ideal candidates for therapeutic treatments.

Host strain specificity that has routinely been observed relative to the bacteriophages isolated from various *C. perfringens* isolates is probably due to evolution of the receptor and anti-receptor molecules. Consequently, several new antimicrobial agents, putative endolysins encoded by the genomes of clostridial bacteriophages, have been identified for use as potential antimicrobials to control *C. perfringens* (Seal B S et al., 2013, "*Alternatives to antibiotics: a symposium on the challenges and solutions for animal production*," Anim. Health Res. Rev. 14: 78-87 and references therein). Additional endolysins have been identified from genomic sequence data and named after their respective source strains. PlyCP10; PlyCP18; PlyCP33; and PlyCP41 (Swift S M et al., 2018, "*Characterization of Two Glycosyl Hydrolases, Putative Prophage Endolysins, That Target Clostridium perfringens*," FEMS Microbiology Letters 365(16), 1 Aug. 2018, fny179; and U.S. Patent Application Publication No. 2018-0195055).

Phage endolysins are known to be modular in structure (Diaz et al. 1990, *Chimeric phage-bacterial enzymes: a clue to the modular evolution of genes*," Proc. Natl. Acad. Sci. U.S.A. 87(20):8125-8129; Donovan E. et al., 2006, "*Peptidoglycan hydrolase fusions maintain their parental specificities*," Appl. Environ. Microbiol. 72:2988-2996; Garcia et al. 1990, "*Modular organization of the lytic enzymes of Streptococcus pneumoniae and its bacteriophages*," Gene 86:81-88). There are numerous examples where single domains are functional without the need for the second lytic domain or the cell wall binding domain (Becker S. C. et al. 2009, "LysK CHAP endopeptidase domain is required for lysis of live staphylococcal cells," FEMS Microbiol. Lett. 294:52-60; Donovan D. M. et al. 2006, "*The cell lysis activity of the Streptococcus agalactiae bacteriophage B*30 *endolysin relies on the cysteine, histidine-dependent amidohydrolase/peptidase domain*," Appl. Environ. Microbiol. 72:5108-5112; Donovan D. M. et al. 2006, "*Lysis of staphylococcal mastitis pathogens by bacteriophage phi*11 *endolysin," FEMS Microbiol. Lett.* 265:133-139).

A thermophile-derived chimeric recombinant lysin may have a catalytic domain selected from the group consisting of $Y412_{CAT}$ (amino acids 1 to 177 of SEQ ID NO: 4); $Y4_{CAT}$ (amino acids 1 to 153 of SEQ ID NO: 16); and $GVE2_{CAT}$ (amino acids 1 to 178 of SEQ ID NO: 23). A thermophile-derived chimeric recombinant lysin may have a cell wall binding domain selected from the group consisting of $CP10_{CWB}$ (SEQ ID NO: 5); $CP18_{CWB}$ (SEQ ID NO: 6); $CP33_{CWB}$ (SEQ ID NO: 7); $CP41_{CWB}$ (SEQ ID NO: 8); and $CP26F_{CWB}$ (SEQ ID NO: 9). Furthermore, to assist in molecular cloning and protein folding, a thermophile-derived chimeric recombinant lysin may have a linker, between the catalytic domain and the cell wall domain, selected from a linker having amino acids 178 to 184 of SEQ ID NO: 4; and a linker having amino acids 178 to 182 of SEQ ID NO: 5. To assist in protein purification, the thermophile-derived chimeric recombinant lysin may have a polyhistidine tag having the amino acid sequence selected from the group consisting of amino acids 1 to 8 of SEQ ID NO 1 and amino acids 1 to 8 of SEQ ID NO: 2.

Examples of the protein structure of the chimeric recombinant lysins of the invention are depicted in FIG. 1, FIG. 2, and FIG. 3. The N-terminal catalytic domains $Y412_{CAT}$, $Y4_{CAT}$, and $GVE2_{CAT}$ are provided by the thermophile endolysins PlyGspY412; PlyGspY4; and PlyGVE2, respectively. The C-terminal cell wall binding (CWB) domain is provided by one of several *C. perfringens* endolysins selected from PlyCP10, PlyCP18, PlyCP33, PlyCP41, and PlyCP26F. To facilitate cloning and protein folding, nucleotides encoding an amino acid linker was added to each of the constructs. To facilitate purification of the chimeric recombinant lysins by nickel-affinity chromatography, a polyhistidine tag (HisTag) was added to the C-terminus of each chimeric recombinant lysin.

The amino acid sequence of chimeric recombinant lysin $Y412_{CAT}$-$CP10_{CWB}$ is set forth in SEQ ID NO: 10, where amino acids 1 to 177 correspond to the thermophile-derived $Y412_{CAT}$ catalytic domain; amino acids 178 to 184 correspond to a linker; amino acids 185 to 343 correspond to the *C. perfringens* derived C-terminal cell wall binding domain $CP10_{CWB}$; and amino acids 344 to 351 correspond to a HisTag. The amino acid sequence of chimeric recombinant lysin $Y412_{CAT}$-$CP18_{CWB}$ is set forth in SEQ ID NO: 11 where amino acids 1 to 177 correspond to the thermophile-derived $Y412_{CAT}$ catalytic domain; amino acids 178 to 182 correspond to linker; amino acids 183 to 352 correspond to the *C. perfringens* derived C-terminal cell wall binding domain $CP18_{CWB}$; and amino acids 353 to 360 correspond to a HisTag. The amino acid sequence of chimeric recombinant lysin $Y412_{CAT}$-$CP33_{CWB}$ is set forth in SEQ ID NO: 12 where amino acids 1 to 177 correspond to the thermophile-derived catalytic domain $Y412_{CAT}$; amino acids 178 to 184 correspond to a linker; amino acids 185 to 427 correspond to the *C. perfringens* derived C-terminal cell wall binding domain $CP33_{CWB}$; and amino acids 428 to 435 correspond to a HisTag.

The amino acid sequence of chimeric recombinant lysin $Y412_{CAT}$-$CP41_{CWB}$ is set forth in SEQ ID NO: 13 where amino acids 1 to 177 correspond to the thermophile-derived catalytic domain $Y412_{CAT}$; amino acids 178 to 184 correspond to a linker; amino acids 185 to 327 correspond to the *C. perfringens* derived C-terminal cell wall binding domain $CP41_{CWB}$; and amino acids 328 to 335 correspond to a HisTag. The amino acid sequence of chimeric recombinant lysin $Y412_{CAT}$-$CP26F_{CWB}$ is set forth in SEQ ID NO: 14 where amino acids 1 to 177 correspond to the thermophile-derived catalytic domain $Y412_{CAT}$; amino acids 178 to 184 correspond to a linker; amino acids 185 to 237 correspond to the *C. perfringens* derived C-terminal cell wall binding domain $CP26F_{CWB}$; and amino acids 238 to 245 correspond to a HisTag.

In the amino acid sequence set forth in SEQ ID NO: 15 amino acids 1 to 216 correspond to the *Geobacillus* sp. Y4.1MC1 mannosyl-glycoprotein endo-beta-N-acetylglucosaminidase having NCBI accession No. ADP73474.1, and amino acids 217 to 224 correspond to a HisTag. In the amino acid sequence set forth in SEQ ID NO: 16 amino acids 1 to 153 correspond to the thermophile-derived catalytic domain $Y4_{CAT}$; amino acids 154 to 156 are encoded by polynucleotides added to facilitate cloning; and amino acids 157 to 164 correspond to a HisTag.

The amino acid sequence of chimeric recombinant lysin $Y4_{CAT}$-$CP10_{CWB}$ is set forth in SEQ ID NO: 17 where amino acids 1 to 153 correspond to $Y4_{CAT}$, the thermophile-derived catalytic domain; amino acids 154 to 160 are encoded by polynucleotides added to facilitate cloning; amino acids 161 to 319 correspond to the *C. perfringens*-derived C-terminal cell wall binding domain $CP10_{CWB}$; and amino acids 320 to 327 correspond to a HisTag. The amino acid sequence of chimeric recombinant lysin $Y4_{CAT}$-$CP18_{CWB}$ is set forth in SEQ ID NO: 18 where amino acids 1 to 153 correspond to $Y4_{CAT}$, the thermophile-derived catalytic domain; amino acids 154 to 158 are encoded by polynucleotides added to facilitate cloning; amino acids 159 to 328 correspond to the C. perfringens derived C-terminal cell wall binding domain CP18$_{CWB}$; and amino acids 328 to 336 correspond to a HisTag.

The amino acid sequence of chimeric recombinant lysin Y4$_{CAT}$-CP33$_{CWB}$ is set forth in SEQ ID NO: 19 where amino acids 1 to 153 correspond to Y4$_{CAT}$, the thermophile-derived catalytic domain; amino acids 154 to 160 are encoded by polynucleotides added to facilitate cloning; amino acids 161 to 403 correspond to the C. perfringens derived C-terminal cell wall binding domain CP33$_{CWB}$; and amino acids 404 to 411 correspond to a HisTag.

The amino acid sequence of chimeric recombinant lysin Y4$_{CAT}$-CP41$_{CWB}$ is set forth in SEQ ID NO: 20 where amino acids 1 to 153 correspond to the thermophile-derived catalytic domain Y4$_{CAT}$; amino acids 154 to 160 are encoded by polynucleotides added to facilitate cloning; amino acids 161 to 303 correspond to the C. perfringens derived C-terminal cell wall binding domain CP41$_{CWB}$; and amino acids 304 to 311 correspond to a HisTag.

The amino acid sequence of chimeric recombinant lysin Y4$_{CAT}$-CP26F$_{CWB}$ is set forth in SEQ ID NO: 21 where amino acids 1 to 153 correspond to the thermophile-derived catalytic domain Y4$_{CAT}$; amino acids 154 to 160 are encoded by polynucleotides added to facilitate cloning; amino acids 161 to 213 correspond to the C. perfringens derived C-terminal cell wall binding domain CP26F$_{CWB}$; and amino acids 214 to 221 correspond to a HisTag.

In the amino acid sequence set forth in SEQ ID NO: 22 amino acids 1 to 233 correspond to Geobacillus virus E2 putative N-acetylmuramoyl-L-alanine amidase having NCBI accession No. YP_001285830.1; and amino acids 234 to 241 correspond to a HisTag.

In the amino acid sequence set forth in SEQ ID NO:23 amino acids 1 to 178 correspond to the thermophile-derived catalytic domain GVE2$_{CAT}$; amino acids 179 to 181 are encoded by polynucleotides added to facilitate cloning; and amino acids 182 to 189 correspond to a HisTag.

The amino acid sequence of chimeric recombinant lysin GVE2$_{CAT}$-CP10$_{CWB}$ is set forth in SEQ ID NO: 24 where amino acids 1 to 178 correspond to the thermophile-derived catalytic domain GVE2$_{CAT}$; amino acids 179 to 185 are encoded by polynucleotides added to facilitate cloning; amino acids 186 to 344 correspond to the C. perfringens derived C-terminal cell wall binding domain CP10$_{CWB}$; and amino acids 345 to 352 correspond to a HisTag.

The amino acid sequence of chimeric recombinant lysin GVE2$_{CAT}$-CP18$_{CWB}$ is set forth in SEQ ID NO: 25 where amino acids 1 to 178 correspond to the thermophile-derived catalytic domain GVE2$_{CAT}$; amino acids 179 to 183 are encoded by polynucleotides added to facilitate cloning; amino acids 184 to 354 correspond to the C. perfringens derived C-terminal cell wall binding domain CP18$_{CWB}$; and amino acids 355 to 361 correspond to a HisTag.

The amino acid sequence of chimeric recombinant lysin GVE2$_{CAT}$-CP33$_{CWB}$ is set forth in SEQ ID NO: 26 where amino acids 1 to 178 correspond to the thermophile-derived catalytic domain GVE2$_{CAT}$; amino acids 179 to 185 are encoded by polynucleotides added to facilitate cloning; amino acids 186 to 428 correspond to the C. perfringens derived C-terminal cell wall binding domain CP33$_{CWB}$; and amino acids 429 to 436 correspond to a HisTag.

The amino acid sequence of chimeric recombinant lysin GVE2$_{CAT}$-CP41$_{CWB}$ is set forth in SEQ ID NO: 27 where amino acids 1 to 178 correspond to the thermophile-derived catalytic domain GVE2$_{CAT}$; amino acids 179 to 185 are encoded by polynucleotides added to facilitate cloning; amino acids 186 to 328 correspond to the C. perfringens derived C-terminal cell wall binding domain CP41$_{CWB}$; and amino acids 329 to 336 correspond to a HisTag.

In the amino acid sequence set forth in SEQ ID NO: 28 amino acids 1 to 234 correspond to PlyGVE2CpCWB, the published version of GVE2$_{CAT}$-CP26F$_{CWB}$.

Expression and purification of the chimeric recombinant lysins of the invention may be performed by any method known in the art. For example, expression of recombinant proteins may be performed using a cell-free expression method, a bacterial expression system, an insect expression system, a yeast expression system, an algal expression system, or a mammalian expression system.

A rapid method for in-vitro recombinant protein expression and analysis is a cell-free expression method. Using a cell free-expression method recombinant proteins are produced in solution using biomolecular translation machinery extracted from cells. This method is called cell-free protein expression because protein synthesis occurs in cell lysates rather than within cultured cells. See, for example, Mikami S et al. 2008, "A human cell-derived in vitro coupled transcription/translation system optimized for production of recombinant proteins," Protein Expr. Purif. 62(2):190-198; Mikami S et al. 2006, "An efficient mammalian cell-free translation system supplemented with translation factors," Protein Expr. Purif. 46(2):348-357; Beebe E. T. et al. 2014, "Automated cell-free protein production methods for structural studies," Pharmacol Toxicol 1140:117-135.

Antimicrobial activity of the chimeric recombinant lysins of the invention may be characterized by any method known in the art. For example, the antimicrobial activity of the chimeric recombinant lysins may be characterized by quantitative peptidoglycan hydrolase assays, for example, a turbidity reduction assay and a plate lysis assay (Donovan D M and Foster-Frey J 2008, "LambdaSa2 prophage endolysin requires Cpl-7-binding domains and amidase-5 domain for antimicrobial lysis of streptococci," FEBS Microbiol. Lett. 287:22-33).

The present invention also relates to an expression cassette comprising a polynucleotide encoding a chimeric recombinant lysin of the invention together with heterologous regulatory elements at positions 5' and/or 3' of the polynucleotide encoding the chimeric recombinant lysin of the invention. The heterologous regulatory elements can function in a host organism. The encoded chimeric recombinant lysin may comprise a thermophile endolysin catalytic domain fused to a C. perfringens endolysin cell wall binding domain.

By host organism there is to be understood any single-celled or lower or higher non-human multi-celled organism into which a polynucleotide encoding a chimeric recombinant lysin according to the invention can be introduced. The regulatory elements required for expressing the polynucleotide encoding a chimeric recombinant lysin are well known to those skilled in the art and depend on the host organism. The means and methods for identifying and choosing the regulatory elements are well known to those skilled in the art and widely described in the literature.

The present invention also relates to an expression vector for transforming a host organism containing at least one polynucleotide encoding a chimeric recombinant lysin as defined above (comprising an N-terminal catalytic domain selected from Y412$_{CAT}$, Y4$_{CAT}$, and Gve2$_{CAT}$; and a C terminal cell wall binding domain selected from the C. perfringens endolysin cell wall binding domains from PlyCP10, PlyCP18, PlyCP33, PlyCP41, or PlyCP26F. An expression vector may comprise, in addition to the polynucleotide encoding a chimeric recombinant lysin, at least one replication origin. This vector can be constituted by a plasmid, a cosmid, a bacteriophage, or a virus which is transformed by introducing the chimeric gene according to the invention. Such expression vectors are specific for the host organism to be transformed, are well known to those skilled in the art, and are widely described in the literature.

A further subject of the invention is a process for the transformation of host organisms, by integrating a least one polynucleotide encoding a chimeric recombinant lysin as defined above. Such transformation may be carried out by any suitable known means which have been widely described in the specialist literature. Transformation of a host organism may be carried out with an expression vector comprising a polynucleotide encoding a chimeric recombinant lysin of the invention.

The term 'codon-optimized' is usually applicable to heterologously expressed genes. Which is when the gene from one organism is expressed in another organism. Multiple codons can often code for the same amino acid. There will exist tRNAs with the corresponding anti-codons having the same amino acid. In different organisms the populations of these degenerate t-RNAs are different with some being more abundant than others. To efficiently express a protein in higher quantities, it is important to use the more abundant of the degenerate tRNA. Thus, a gene can be mutated (or synthesized de novo) to change the codons used for coding particular amino acids, without changing the amino acid sequence of the protein itself. Rare codons are replaced by codons that are more abundant in the genes of the host organism.

A polynucleotide encoding a chimeric recombinant lysin of the invention may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof. This will also include a polynucleotide for which the codons encoding the chimeric recombinant lysins of the invention will have been optimized according to the host organism in which it will be expressed. Codon optimization methods are well known to those skilled in the art.

As used herein, the terms "isolated," and "purified" refer to material that is substantially or essentially free from components that normally accompany the referenced material in its native state.

Conventional nucleic acid purification methods known to skilled artisans may be used to obtain isolated polynucleotides encoding the chimeric recombinant lysins of the invention.

The term "transgene" is understood to describe genetic material which has been or is about to be artificially inserted into the genome of a non-human animal or microbe, and particularly into a cell of a living non-human mammal. It is to be understood that as used herein the term "transgenic" includes any microbe, cell, cell line, or tissue, the genotype of which has been altered by the presence of a heterologous nucleic acid including those transgenics initially so altered as well as those created by sexual crosses or asexual propagation from the initial transgenic.

The term "transformation" refers to a permanent or transient genetic change induced in a cell following the incorporation of a polynucleotide not normally found in the cell (i.e. DNA exogenous to the cell). Where the cell is a microbe or mammalian cell, a permanent genetic change is generally achieved by introduction of the DNA into the genome of the cell. When the cell is a bacterial or microbial cell, the term can refer to an extrachromosomal, self-replicating vector which harbors a selectable antibiotic resistance or genome integrated form. Thus, polynucleotides encoding chimeric recombinant lysins of the invention can be incorporated into constructs, typically DNA constructs, capable of introduction into and replication in a host cell, whether that cell be a eukaryote, archaea, or bacteria. Such a construct can be a vector that includes a replication system and sequences that are capable of transcription and translation of a polypeptide-encoding sequence in a given host cell.

In an embodiment, the invention relates to a host cell expressing a chimeric recombinant lysin comprising at least one thermophile-derived catalytic domain selected from the group consisting of the N-terminal catalytic domain from PlyGspY412, PlyGspY4, and PlyGve2; and at least one cell wall binding domain selected from the group consisting of the cell wall binding domain from C. perfringens endolysins PlyCP10, PlyCP18, PlyCP33, PlyCP41, and PlyCP26, where the chimeric recombinant lysin does not have the amino acid sequence set forth in SEQ ID NO: 28. In some embodiments, the host cell expressing a chimeric recombinant lysin of the invention is selected from a bacterial cell, a fungal cell, a plant cell, and a mammalian cell.

The term "construct" refers to a recombinant nucleic acid, generally a recombinant DNA, that has been generated for the purpose of the expression of a specific polypeptide, or is to be used in the construction of other recombinant polynucleotides. A "construct" or "chimeric gene construct" refers to a nucleic acid encoding a protein, operably linked to a nucleic acid comprising a promoter and/or other regulatory sequences.

The expression control sequences may be eukaryotic promoter systems when using vectors capable of transforming or transfecting eukaryotic host cells. The expression control sequences may be prokaryotic when prokaryotic hosts are used. Once the vector has been incorporated into the appropriate host, the host is maintained under conditions suitable for high level expression of the poly nucleotides, and as desired, the collection and purification of the chimeric recombinant lysin polypeptides of the invention may follow; see, e.g., the examples below.

As described above, the recited nucleic acid molecules can be used alone or as part of a vector to express the chimeric recombinant lysin polypeptides of the invention in cells, for, e.g., purification but also for gene therapy purposes. The nucleic acid molecules or vectors containing the nucleic acid sequences encoding any one of the above described chimeric recombinant lysin polypeptides of the invention is introduced into the cells which in turn produces the chimeric recombinant lysin polypeptide of interest.

The term "operably linked" refers to the association of two or more nucleic acid fragments on a single polynucleotide so that the function of one is affected by the function of the other. For example, a promoter is operably linked with a coding sequence when it is capable of affecting the expression of that coding sequence (i.e., that the coding sequence is under the transcriptional control of the promoter). A specific polynucleotide is operably linked to at least one regulatory sequence when it is connected in such a way as to permit gene expression when the appropriate molecules (e.g., transcriptional activator proteins) are bound to the regulatory sequence(s).

"Regulatory sequences" refer to nucleotide sequences located upstream (5' non-coding sequences), within, or downstream (3' non-coding sequences) of a coding sequence, and which influence the transcription, RNA processing, RNA stability, or translation of the associated coding sequence.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter.

As used herein, "recombinant" refers to a nucleic acid molecule which has been obtained by manipulation of genetic material using restriction enzymes, ligases, and similar genetic engineering techniques as described by, for example, Sambrook et al. 1989, Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to genetic material with naturally occurring mutations.

"Chimeric protein" refers to a hybrid protein encoded by a nucleotide sequence comprising polynucleotides encoding at least two different proteins. The different proteins may be derived from different sources, strains, or species, and do not recombine under natural conditions. The different proteins may be encoded by two or more polynucleotide molecules from the same species, but are linked in a manner that does not occur in the native genome.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

A "protein" or "polypeptide" is a chain of amino acids arranged in a specific order determined by the coding sequence in a polynucleotide encoding the polypeptide. Each protein or polypeptide has a unique function.

Provided herein are recombinant polynucleotides encoding chimeric recombinant lysins derived from fusing the DNA sequences from one of three thermophile endolysin catalytic domains with a cell wall binding domain from a *C. perfringens* endolysin selected from PlyCP10, PlyCP18, PlyCP33, PlyCP41, and PlyCP26F.

Modifications of the primary amino acid sequences of the chimeric recombinant lysins of the invention may result in further mutant or variant proteins having substantially equivalent activity to the chimeric recombinant lysin polypeptides described herein. Such modifications may be deliberate, as by site-directed mutagenesis, or may occur by spontaneous changes in the nucleic acid sequences where these changes produce modified polypeptides having substantially equivalent activity to the chimeric recombinant lysin polypeptides of the invention.

In an embodiment, the invention relates to a polynucleotide encoding a chimeric recombinant lysin comprising at least one thermophile-derived catalytic domain selected from the group consisting of the N-terminal catalytic domain from PlyGspY412, PlyGspY4, and PlyGve2; at least one cell wall binding domain selected from the group consisting of the cell wall binding domain from *C. perfringens* endolysins PlyCP10, PlyCP18, PlyCP33, PlyCP41, and PlyCP26F; optionally a linker between the catalytic domain and the cell wall binding domain; and optionally a polyhistidine tag (HisTag), where the chimeric recombinant lysin does not have the amino acid sequence set forth in SEQ ID NO: 28.

The invention also provides for a host comprising a nucleic acid encoding for a chimeric recombinant lysin of the present invention. Said host may be produced by introducing the above described vector of the invention or the above described nucleic acid molecule of the invention into the host. The presence of at least one vector or at least one nucleic acid molecule in the host may mediate the expression of a chimeric recombinant lysin of the present invention.

The described polynucleotide or vector of the invention, which is introduced in the host may either integrate into the genome of the host or it may be maintained extrachromosomally. The host can be any prokaryote or eukaryotic cell. The term "prokaryote" is meant to include all bacteria, which can be transformed or transfected with DNA or RNA molecules for the expression of a chimeric recombinant lysin of the invention. Prokaryotic hosts may include gram negative as well as gram positive bacteria such as, for example, *E. coli* (particularly XI-blue, DH5.alpha., BI21, M15 [pREP4], SG13005 [pREP4], BL21 (DE3) pLysS), *Holomonos elongate, Coulobocter* sp., *Holobocterium holobium, S. typhimurium, Serratia marcescens* and *Bacillus subtilis*. The term "eukaryotic" is meant to include yeast, higher plant, insect, and mammalian cells. Depending upon the host employed in a recombinant production procedure, the protein encoded by the polynucleotide of the present invention may be glycosylated or may be non-glycosylated. The plasmid or virus containing the coding sequence of a chimeric recombinant lysin polypeptide of the invention may be genetically fused to a tag to facilitate purification of the polypeptide. The polypeptide may be genetically fused to an N-terminal and/or C-terminal peptide tag that can be used for affinity purification and or detection. For example, the peptide tag may be a polyhistidine peptide (HisTag) or a FLAG tag. An above described polynucleotide can be used to transform or transfect the host using any of the techniques commonly known to those of ordinary skill in the art. Furthermore, methods for preparing fused, operably linked genes and expressing them in, e.g., mammalian cells and bacteria are well-known in the art.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments of the instant invention with modifications such as deletion or insertion of nucleotides that do not substantially affect the functional properties of the resulting transcript. It is therefore understood that the invention encompasses more than the specific exemplary chimeric recombinant lysins with the specific amino acid sequences disclosed herein, and the nucleotide sequences encoding them, but includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic amino acid, such as glycine, or a more hydrophobic amino acid, such as valine, leucine, or isoleucine. Similarly, changes which result in substitution of one negatively charged amino acid for another, such as aspartic acid for glutamic acid, or one positively charged amino acid for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

In an embodiment, the invention relates to a nucleic acid construct comprising a promoter operably linked to a polynucleotide encoding a chimeric recombinant lysin comprising at least one thermophile-derived catalytic domain selected from the group consisting of the N-terminal catalytic domain from PlyGspY412, PlyGspY4, and PlyGve2; at least one cell wall binding domain selected from the group consisting of the cell wall binding domain from C. perfringens endolysins PlyCP10, PlyCP18, PlyCP33, PlyCP41, and PlyCP26F. In some embodiments of the invention the nucleic acid construct comprises nucleotides encoding a polyhistidine tag (HisTag), where the recombinant lysin does not have the amino acid sequence set forth in SEQ ID NO: 28. In some embodiments of the invention the HisTag has the amino acid sequence set forth in SEQ ID NO: 1 or SEQ ID NO: 2.

In some embodiments, the invention relates to a vector comprising a nucleic acid construct comprising a promoter operably linked to a polynucleotide encoding a chimeric recombinant lysin comprising at least one thermophile-derived catalytic domain selected from the group consisting of the N-terminal catalytic domain from PlyGspY412, PlyGspY4, and PlyGve2; and at least one cell wall binding domain selected from the group consisting of the cell wall binding domain from C. perfringens endolysins PlyCP10, PlyCP18, PlyCP33, PlyCP41, and PlyCP26F, where the recombinant lysin does not have the amino acid sequence set forth in SEQ ID NO: 28.

An embodiment the invention relates to host cells, in particular prokaryotic or eukaryotic cells, genetically engineered with polynucleotides encoding the chimeric recombinant lysin polypeptides of the invention, or with the vectors of the present invention, or which are obtainable by a method for producing genetically engineered host cells, as well as to cells derived from such transformed host cells. A host cell comprising polynucleotides encoding the chimeric recombinant lysins of the present invention may be a bacterial cell, a yeast cell, a fungus, a plant cell, or an animal cell. In some embodiments, the animal cell may be a mammalian cell.

In a further embodiment, the present invention relates to a process for the production of a chimeric recombinant lysin of the invention, said process comprising culturing a host cell of the invention under conditions allowing the expression of a chimeric recombinant lysin of the invention. In some embodiments, the invention further relates to recovering the produced chimeric recombinant lysin from the culture.

Transformed host cells can be grown in fermentors and cultured according to techniques known in the art to achieve optimal cell growth. The chimeric recombinant lysin polypeptide of the invention can then be isolated from the growth medium, cellular lysates, or cellular membrane fractions. The isolation and purification of the, e.g., microbially expressed polypeptides of the invention may be by any conventional means such as, for example, preparative chromatographic separations and immunological separations such as those involving the use of monoclonal or polyclonal antibodies directed, e.g., against a tag of the polypeptide of the invention or as described in the appended examples.

The conditions for the culturing of a host, which allow the expression of the chimeric recombinant lysins of the invention, are known in the art to depend on the host system and the expression system/vector used in such process. The parameters to be modified in order to achieve conditions allowing the expression of a recombinant polypeptide are known in the art. Thus, suitable conditions can be determined by the person skilled in the art in the absence of further inventive input.

In an embodiment of the invention a chimeric recombinant lysin polypeptide may be expressed in a host cell, such as a bacterial cell, an animal cell, or a yeast cell. In an embodiment of the invention, cells expressing the polypeptide may be provided to chickens or other animals. Host cells expressing chimeric recombinant lysins of the invention may be provided to chickens or other animals with water or food. For example, the chimeric recombinant lysin polypeptide may be expressed in yeast, and then the yeast fed to chickens. Chickens digest the yeast and release the chimeric recombinant lysin polypeptide to attack the C. perfringens in the intestine.

Once expressed, the polypeptide of the invention may be purified according to standard procedures of the art, including ammonium sulfate precipitation, affinity columns, column chromatography, gel electrophoresis and the like; see, Scopes, "Protein Purification", Springer-publisher (Verlag), N.Y. (1982). Substantially pure polypeptides of at least about 90 to 95% homogeneity are preferred, and 98 to 99% or more homogeneity are most preferred for pharmaceutical uses. Once purified, partially or to homogeneity as desired, the polypeptide of the invention may then be used therapeutically (including extra corporally) or in developing and performing assay procedures. Furthermore, examples for methods for the recovery of the polypeptide of the invention from a culture are described in detail in the appended examples. In one embodiment, chimeric recombinant lysins of the present invention are purified. In another embodiment the chimeric recombinant lysins of the present invention are purified, while retaining the ability to lyse C. perfringens.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have phage PlyCP10, PlyCP18, PlyCP33, and PlyCP41 endolysin-like activity. Alternatively, fragments of a nucleotide sequence that are useful as hybridization probes may not encode fragment proteins retaining biological activity.

By "variants" polypeptides and polynucleotides with substantially similar sequences are intended. For polynucleotides, conservative variants include those sequences that, because of the degeneracy of the genetic code, encode a polypeptides with amino acid sequence of one of the chimeric recombinant lysin polypeptides of the invention. Allelic variants such as these can be identified with the use of well-known molecular biology techniques, as, for example, with polymerase chain reaction (PCR), a technique used for the amplification of specific DNA segments, and DNA sequencing. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequence of the chimeric recombinant lysins set forth herein.

In an embodiment, the invention relates to a composition comprising a chimeric recombinant lysin polypeptide comprising at least one thermophile endolysin catalytic domain selected from the group consisting of the N-terminal catalytic domain from PlyGspY412, PlyGspY4, and PlyGve2; and at least one cell wall binding domain selected from the group consisting of the cell wall binding domain from C. perfringens endolysins PlyCP10, PlyCP18, PlyCP33, PlyCP41, and PlyCP26F, where the recombinant lysin does not have the amino acid sequence set forth in SEQ ID NO: 28. In some embodiments of the invention the chimeric recombinant lysin polypeptide in the composition comprises a HisTag. In some embodiments, the invention relates to a composition further comprising a pharmaceutically acceptable carrier.

Compositions comprising the chimeric recombinant lysins of the invention may comprise the chimeric recombinant lysin dissolved or suspended in an aqueous carrier or medium. The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The compositions of this invention comprise ingredients which are generally regarded as safe, and are not of themselves or in admixture, incompatible with human and veterinary applications.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules. In an embodiment of the invention, a composition comprising a chimeric recombinant lysin of the invention is suitable for oral administration. In an embodiment, the composition comprising a chimeric recombinant lysin of the invention is in the form of animal feed.

An oral composition can generally include an inert diluent or an edible carrier. The nutraceutical composition can comprise a functional food component or a nutrient component. The term "functional food" refers to a food which contains one or a combination of components which affects functions in the body so as to have positive cellular or physiological effects. The term "nutrient" refers to any substance that furnishes nourishment to an animal.

Compositions of this invention may comprise ingredients which are nutritional supplements or feed supplements used for feeding livestock, in particular, poultry. The terms "feed supplement," "nutritional supplement," and "feed additive" are used herein interchangeably unless otherwise indicated. The terms are to be understood as an ingredient or a mixture or combination of ingredients which can be mixed to a feed to fulfill one or more specific need(s), for example, as part of a diet. The feed additive may be a component of a feed product. The feed product containing the feed additive according to the present invention may contain further suitable other components like cereal products, protein raw material, fiber raw material and lignocelluloses-containing raw material. Moreover, the feed product may contain at least one of the components selected from trace elements, vitamins, tallow, enzymes, minerals and common additives added to feed products especially for poultry. Further, the term "feed" here is not restricted exclusively to substances which would normally be described as feed, but also refers to nutritional additives, e.g. yeast, starch, various types of sugar, etc.

Likewise, ingredients may be selected for any given composition which are cooperative in their combined effects whether incorporated for antimicrobial efficacy, physical integrity of the formulation, or to facilitate healing and health in medical and veterinary applications. Generally, the composition comprises a carrier which functions to dilute the active ingredients and facilitates stability and application to the intended surface. The carrier is generally an aqueous medium such as water, or an organic liquid such as an oil, a surfactant, an alcohol, an ester, an ether, or an organic or aqueous mixture of any of these. Water is preferred as a carrier or diluent in compositions of this invention because of its universal availability and unquestionable economic advantages over other liquid diluents.

Avoiding the generalized use of broad range antimicrobials and using highly specific antimicrobials for just the target organisms involved, should help reduce the ever-increasing incidence of antibiotic resistance. Thus, the chimeric recombinant lysins of the invention are useful in the treatment of infection and disease caused by *C. perfringens*.

As used herein, "HisTag" and "polyhistidine tag" are used interchangeably and refer to the 6×His tag, His6 tag and/or hexa histidine tag. It is an amino acid motif consisting of at least 6 histidine residues fused to the carboxyl (C-) or amino (N-) terminus of a target protein in transfected cells. This tag is most commonly used in the production of recombinant proteins since the string of histidine residues binds to several types of immobilized ions (such as nickel, cobalt and copper) under specific buffer conditions to allow for the simple detection and purification of His-tagged proteins. Due to its relatively small size, low immunogenicity, hydrophilic nature, and versatility in the presence of detergents and many other additives, and under native and denaturing conditions, the polyhistidine tag is now considered as the most widely used affinity tag for a variety of protein purification purposes. In addition, its ability to detect and purify recombinant proteins without using a protein-specific antibody or probe, and the availability of anti-His tag antibodies for use in assays involving His-tagged proteins make 6×His tags all the more popular.

As used herein, the singular forms "a," "an," and "the" designate both the singular and the plural, unless the context clearly indicates otherwise.

The term "about" is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the recited value.

The terms "individual," "subject," and "animal", are used interchangeably herein, and refer to vertebrates that support *C. perfringens* infection. Particular subjects are birds such as water fowl, chickens, or turkeys. In some embodiments of the invention the vertebrates are mammals such as pigs, horses, cows, or humans. In some embodiments the vertebrates are humans. In some embodiments the vertebrates are chickens.

As used herein, the terms "isolated," and "purified" refer to material that is substantially or essentially free from components that normally accompany the referenced material in its native state.

EXAMPLES

Having now generally described this invention, the same will be better understood by reference to certain specific examples, which are included herein only to further illustrate the invention and are not intended to limit the scope of the invention as defined by the claims.

Example 1

Preparation, Expression, and Analysis of Chimeric Lysins

Recombinant chimeric lysins derived from fusing the DNA sequences from thermophile endolysin catalytic domains with one of several cell wall binding domains from *C. perfringens* endolysins were prepared.

Thermophile bacteria genomes were examined at the Integrated Microbial Genomes (IMG) website for potential prophage and endolysin sequences. Genes encoding amidase-containing proteins were identified adjacent to predicted bacteriophage genes. The endolysin referred to herein as PlyGspY412 has IMG geneID: 646372128; and GenBank accession ACX77322. This endolysin is an amidase belonging to a subgroup or family defined in the Protein Families Database (PFAM) as amidase_3. This protein contains a Sporulation-related repeat (SPOR) domain in the C-terminal half, which is usually associated with cell wall binding ($_{CWB}$) domains. The endolysin referred to herein as PlyGspY4 has IMG geneID: 649721886; and GenBank accession ADP73474. This endolysin has a glucosaminidase catalytic domain and a C-terminal LysM binding domain. A chimeric recombinant lysin comprising the catalytic domain of the GVE2 endolysin (GenBank accession YP 001285830) and the PlyCP26 cell wall binding domain to create GVE2$_{CAT}$-CP26F$_{CWB}$ was published as PlyGVE2CpCWB by Swift, S. M., et al. (2015, "*A Thermophilic Phage Endolysin Fusion to a Clostridium perfringens-Specific Cell Wall Binding Domain Creates an Anti-Clostridium Antimicrobial with Improved Thermostability*," Viruses 7(6): 3019-3034). The GenBank accession No. for the PlyCP26F (N-acetylmuramoul-L-alanine amidase [*Clostridium* phage phiCP26]) protein is AEA86246. The *C. perfringens* lysin proteins PlyCP10, PlyCP18, PlyCP33, and PlyCP41 are disclosed in U.S. Patent Publication No. 2018-0195055. The GenBank Accession Number for the *C. perfringens* lysin protein PlyCP10 is AQS60701, for PlyCP18 is AQS60703, for PlyCP33 is AQS60704, and for PlyCP41 is AQS60702.

Polynucleotides of the above-mentioned endolysins were synthesized as *E. coli*-codon optimized genes. The synthesized gene polynucleotides served as templates for amplification of the catalytic domain sequences using Polymerase Chain Reaction (PCR). To assist in cloning and protein purification polynucleotides encoding linkers and polyhistidine tags were added to the catalytic domains during PCR amplification. The codon optimized endolysin catalytic domains were cloned into the pET21a plasmid for expression in BL21(DE3) *E. coli* cells. The *E. coli*-codon optimized sequences for the cell wall binding ($_{CWB}$) domains from several *C. perfringens* targeting endolysins, PlyCP10, PlyCP18, PlyCP33, PlyCP41, and PlyCP26F, were also amplified by PCR. To assist in cloning and protein purification polynucleotides encoding linkers and polyhistidine tags were added to the cell wall binding domains during PCR amplification. Using standard molecular techniques, the amplified *C. perfringens* $_{CWB}$ domains were cloned into the plasmids containing the Y412$_{CAT}$, Y4$_{CAT}$, and GVE2$_{CAT}$ catalytic domains to create the lysin chimeric fusions. Nucleotides were added to the constructs to facilitate cloning and purification by nickel-affinity chromatography. Polynucleotides encoding the amino acids LEHHHHHH (set forth in SEQ ID NO: 1) were added to the C-terminus of the chimeric recombinant lysins comprising CP10$_{CWB}$; CP33$_{CWB}$; CP41$_{CWB}$; and CP26F$_{CWB}$. Polynucleotides encoding the amino acids VEHHHHHH (set forth in SEQ ID NO: 2) were added to the chimeric recombinant lysins comprising CP18$_{CWB}$. All plasmids were sequenced to confirm identity and cloning integrity.

Schematics of the protein structures of the thermophile endolysins, their N-terminal catalytic domains, and the chimeric recombinant lysins of the invention are depicted in FIG. 1; FIG. 2; and FIG. 3. The schematics of the PlyGspY412 endolysin, its N-terminal amidase catalytic domain Y412$_{CAT}$, and the chimeric recombinant lysins Y412$_{CAT}$-CP10$_{CWB}$; Y412$_{CAT}$-CP18$_{CWB}$; Y412$_{CAT}$-CP33$_{CWB}$; Y412$_{CAT}$-CP41$_{CWB}$; and Y412$_{CAT}$-CP26F$_{CWB}$ are shown in FIG. 1. The schematics of the PlyGspY4 endolysin, its N-terminal glucosaminidase catalytic domain Y4$_{CAT}$, and the chimeric recombinant lysins Y4$_{CAT}$-CP10$_{CWB}$; Y4$_{CAT}$-CP18$_{CWB}$; Y4$_{CAT}$-CP33$_{CWB}$; Y4$_{CAT}$-CP41$_{CWB}$; and Y4$_{CAT}$-CP26F$_{CWB}$ are shown in FIG. 2. The schematics of the PlyGVE2 endolysin, its N-terminal amidase catalytic domain GVE2$_{CAT}$, and the chimeric recombinant lysins GVE2$_{CAT}$-CP10$_{CWB}$; GVE2$_{CAT}$-CP18$_{CWB}$; GVE2$_{CAT}$-CP33$_{CWB}$; GVE2$_{CAT}$-CP41$_{CWB}$; and GVE2$_{CAT}$-CP26F$_{CWB}$ are shown in FIG. 3.

The chimeric recombinant lysin proteins were expressed and purified essentially as described by Abaev et al. (2013, "*Staphylococcal phage* 2638*A endolysin is lytic for Staphylococcus aureus and harbors an inter-lytic-domain secondary translational start site*," Appl. Microbiol. Biotechnol. 97(8):3449-3456). Briefly, BL21 (DE3) *E. coli* cells (Invitrogen, now Thermo Fisher Scientific, Waltham, Mass. USA) carrying endolysin expression plasmids, pET variants, were propagated in 1 Luria Bertani (LB) broth supplemented with 150 μg/mL ampicillin at 37° C. (shaking at 225 rpm) until the $OD_{600}$ reading was 0.4-0.6 (log phase growth). The broth culture was held on ice for 15 minutes and then treated with 1 mM isopropyl-β-D-1-thiogalactopyranoside (IPTG) for induction of the peptidoglycan hydrolase gene. The induced cells were then incubated with shaking 18 hours at 10° C. The culture was centrifuged for 30 minutes at 6000×g. The supernatant was removed, the pellet was suspended in protein purification buffer (50 mM $NaH_2PO_4$, 300 mM NaCl, 10 mM imidazole, 30% glycerol, pH 8.0) and the suspended cells were lysed by sonication. The lysate was centrifuged for 30 minutes at 7500×g to pellet the cell debris. The resultant supernatant was purified via Nickel-NTA column chromatography following manufacturer's instructions (QIAGEN, Germantown, Md. USA). The purified chimeric recombinant lysin in elution buffer (50 mM NaH$_2$PO$_4$, 250 mM imidazole, 300 mM NaCl, 30% glycerol, pH 8.0) and the cellular lysate were analyzed by 15% Sodium Dodecyl Sulfate Poly-Acrylamide Gel Electrophoresis (SDS-PAGE) and stained with Coomassie Blue to confirm the purity of the expressed protein (1990. *Gel Electrophoresis of Proteins: A Practical Approach*, Hames, B. D. and Rickwood, D., Eds., Oxford University press, New York, N.Y., pages 1147).

The amino acid sequence set forth in SEQ ID NO 3 is MMVRIVLDAGHGGHDPGA VANGLREKDLT-LAIVKHIGKMLGEYEGAEVHYTRTDDRFLELSERAA-IANKLKADLL ISVHINAGGGTGFESYIYNGNVSPA-TIAYQNVIHQELMKAIGNVTDRGKKRANYAVL RETNMPAILTENLFIDNANDAAKLKSE-QFLQQVAYGHVQGIVKAFGLKKKAKPQTK QKVSDGKLYRVQVGAFADPENAKRL-ADELKKKGYPATIVLEHHHHHH. The amino acid sequence of the *Geobacillus* sp Y412MC61 cell wall/hydrolase PlyGspY412 native protein having NCBI accession No. ACX77311.1 is set forth in amino acids 1 to 227 of SEQ ID NO: 3; and the amino acids 228 to 235 correspond to an introduced polyhistidine tag (HisTag).

The amino acid sequence set forth in SEQ ID NO: 4 is MMVRIVLDAGHGGHDPGA VANGLREKDLT-LAIVKHIGKMLGEYEGAEVHYTRTDDRFLELSERAA-IANKLKADLL ISVHINAGGGTGFESYIYNGNVSPA-TIAYQNVIHQELMKAIGNVTDRGKKRANYAVL RETNMPAILTENLFIDNANDAAKLKSE-QFLQQVAYGHVQGIVKAFGSSLEHHHHHH. In SEQ ID NO: 4 amino acids 1 to 177 correspond to the Y412$_{CAT}$ catalytic domain; amino acids 178 to 180 are encoded by polynucleotides added to facilitate cloning; amino acids 180 to 188 correspond to a HisTag.

The amino acid sequence set forth in SEQ ID NO: 5 is TQEIFINGASQKATENKSFF TNARAK-VALDPRSNPSDNYKDLGEIYAEERIQVLAEIC-DREDYLPVKYWKDASGCES SKVWVNAN-KDYLEIDTNARSFNIVTELDARYEPSVNSKRMGYVKN-NERLYVHRVEG DYVLATYYAGNGYKTAWFTKEYIIKD. This amino acid sequence is the amino acid sequence of the CP10$_{CWB}$.

The amino acid sequence set forth in SEQ ID NO: 6 is RMLKSIDENIVNDTDTTDVPSSD DSNKKDFSTNARALVALDPRDNPSD-NYSDLGEIYKDERFRVLAEVCDKGDFLPIVYWKDSEGRESGKV WVRSKQDYM-MIDTYHKVFNVITELDARYEPSPNSSRMGYVTNGERLYVHRIEGNYALATYFAG-NGYK TAWFTKKYIEKI. This is the amino acid sequence of the CP18$_{CWB}$.

The amino acid sequence set forth in SEQ ID NO: 7 is LSEFKNNSYRPTGGSSETV VSENGFYTSNEERTNA-TIVGKGDIEVLDEKGKVIQGRHISSL-DRVFVLGIYPSRNHIELI YPGKDEKYHAYISIE-NYSRLSFDYHMQYKNDDGVTYVWWDSKNVNVK-NHDEELQP HQKASPMYRTNGWLRV-TFYRADGNPSDGYVRYEGEQKERFYRKGKVVNVRT-SLTV RAGAGTNYSAIGSLDPNENVEILEK-TEGWYYIEYNARNERKRGYVSKKYIEIIQ. This is the amino acid sequence of the CP33$_{CWB}$.

The amino acid sequence set forth in SEQ ID NO: 8 is EDFLKKDFTLENATTCNVD TELNIRAKGTTGATIVG-SIPAGDR-FRIKWVDSDYLGWYYIEYQGITGYVSQDYVEKLQ MATTCNVDSVLNVRAEGNTSSNIVATINP-GEVFRIDWVDSDFIGWYRITTANGANGF VKSDFVKKL. This is the amino acid sequence of the CP41$_{CWB}$.

The amino acid sequence set forth in SEQ ID NO: 9 is EDFLKKDFTLENATTCNVD TELNIRAKGTTGATIVG-SIPAGDR-FRIKWVDSDYLGWYYIEYQGITGYVSQDYVEKLQ MATTCNVDSVLNVRAEGNTSSNIVATINP-GEVFRIDWVDSDFIGWYRITTANGANGF VKSDFVKKL. This is the amino acid sequence of the CP26F$_{CWB}$.

The amino acid sequence set forth in SEQ ID NO: 10 is MMVRIVLDAGHGGHDPG AVANGLREKDLT-LAIVKHIGKMLGEYEGAEVHYTRTDDRFLELSERAA-IANKLKADL LISVHINAGGGTGFESYIYNGNVSPA-TIAYQNVIHQELMKAIGNVTDRGKKRANYAV LRETNMPAILTENLFIDNANDAAKLKSE-QFLQQVAYGHVQGIVKAFGSSLDGSTQEIF INGASQKATENKSFFTNARAK-VALDPRSNPSDNYKDLGEIYAEERIQVLAEICDREDY LPVKYWKDASGCESSKVWVNANKDYLEIDT-NARSFNIVTELDARYEPSVNSKRMGY VKNNERLY-VHRVEGDYVLATYYAGNGYK-TAWFTKEYIIKDLEHHHHHH. In SEQ ID NO: 10 amino acids 1 to 177 correspond to the thermophile-derived catalytic domain Y412$_{CAT}$; amino acids 178 to 184 are encoded by polynucleotides added to facilitate cloning; amino acids 185 to 343 correspond to the *C. perfringens*-derived C-terminal cell wall binding domain CP10$_{CWB}$; and amino acids 344 to 351 correspond to a HisTag.

The amino acid sequence set forth in SEQ ID NO: 11 is MMVRIVLDAGHGGHDPG AVANGLREKDLT-LAIVKHIGKMLGEYEGAEVHYTRTDDRFLELSERAA-IANKLKADL LISVHINAGGGTGFESYIYNGNVSPA-TIAYQNVIHQELMKAIGNVTDRGKKRANYAV LRETNMPAILTENLFIDNANDAAKLKSE-QFLQQVAYGHVQGIVKAFGSSLERMLKSID ENIVNDTDTTDVPSSDDSNKKDFSTNARAL-VALDPRDNPSDNYSDLGEIYKDERFRV LAEVCDKGDFLPIVYWKDSEGRESGKVWVR-SKQDYMMIDTYHKVFNVITELDARYE PSPNSSRMGYVTNGERLYVHRIEGNYALATYFAG-NGYKTAWFTKKYIEKIVEHHHH HH. In SEQ ID NO: 11 amino acids 1 to 177 correspond to the thermophile-derived catalytic domain Y412$_{CAT}$; amino acids 178 to 182 are encoded by polynucleotides added to facilitate cloning; amino acids 183 to 352 correspond to the *C. perfringens* derived C-terminal cell wall binding domain CP18$_{CWB}$; and amino acids 353 to 360 correspond to a HisTag.

The amino acid sequence set forth in SEQ ID NO: 12 is MMVRIVLDAGHGGHDPG AVANGLREKDLT-LAIVKHIGKMLGEYEGAEVHYTRTDDRFLELSERAA-IANKLKADL LISVHINAGGGTGFESYIYNGNVSPA-TIAYQNVIHQELMKAIGNVTDRGKKRANYAV LRETNMPAILTENLFIDNANDAAKLKSE-QFLQQVAYGHVQGIVKAFGSSLDGSLSEFK NNSYRPTGGSSETVVSENGFYTSNEERTNA-TIVGKGDIEVLDEKGKVIQGRHISSLDR VFVLGIYPSRNHIELIYPGKDEKYHAYISIE-NYSRLSFDYHMQYKNDDGVTYVWWDS KNVNVKNHDEELQPHQKASPMYRTNGWLRVTF-YRADGNPSDGYVRYEGEQKERFY RKGKVVNVRT-SLTVRAGAGTNYSAIGSLDPNENVEILEK-TEGWYYIEYNARNERKRG YVSKKYIE-IIQLEHHHHHH. In SEQ ID NO: 12 amino acids 1 to 177 correspond to the thermophile-derived catalytic domain Y412$_{CAT}$; amino acids 178 to 184 are encoded by polynucleotides added to facilitate cloning; amino acids 185 to 427 correspond to the *C. perfringens* derived C-terminal cell wall binding domain CP33$_{CWB}$; and amino acids 428 to 435 correspond to a HisTag.

The amino acid sequence set forth in SEQ ID NO: 13 is MMVRIVLDAGHGGHDPG AVANGLREKDLT-LAIVKHIGKMLGEYEGAEVHYTRTDDRFLELSERAA-IANKLKADL LISVHINAGGGTGFESYIYNGNVSPA-TIAYQNVIHQELMKAIGNVTDRGKKRANYAV LRETNMPAILTENLFIDNANDAAKLKSE-QFLQQVAYGHVQGIVKAFGSSLDGSEDFL KKDFTLENATTCNVDTELNIRAKGTTGATIVGSI-PAGDRFRIKWVDSDYLGWYYIEY QGITGYVSQDYVEKLQMATTCNVDSVLNVRAE-GNTSSNIVATINPGEVFRIDWVDSD FIGWYRITTAN-GANGFVKSDFVKKLLEHHHHHH. In SEQ ID NO: 13 amino acids 1 to 177 correspond to the thermophile-derived catalytic domain Y412$_{CAT}$; amino acids 178 to 184 are encoded by polynucleotides added to facilitate cloning; amino acids 185 to 327 correspond to the *C. perfringens* derived C-terminal cell wall binding domain CP41$_{CWB}$; and amino acids 328 to 335 correspond to a HisTag.

The amino acid sequence set forth in SEQ ID NO: 14 is MMVRIVLDAGHGGHDPG AVANGLREKDLT-LAIVKHIGKMLGEYEGAEVHYTRTDDRFLELSERAA-IANKLKADL LISVHINAGGGTGFESYIYNGNVSPA-TIAYQNVIHQELMKAIGNVTDRGKKRANYAV LRETNMPAILTENLFIDNANDAAKLKSE-QFLQQVAYGHVQGIVKAFGSSLDGSRYLA NAIDPNI-PLEKEQDYYRVCVQRFTNKEDAEKAQQRISNEL-GYYCFAEKILEHHHHHH. In SEQ ID NO: 14 amino acids 1 to 177 correspond to the thermophile-derived catalytic domain Y412$_{CAT}$; amino acids 178 to 184 are encoded by polynucleotides added to facilitate cloning; amino acids 185 to 237 correspond to the *C. perfringens*-derived C-terminal cell wall binding domain CP26F$_{CWB}$; and amino acids 238 to 245 correspond to a HisTag.

The amino acid sequence set forth in SEQ ID NO: 15 is MNDFIREIAPFAQRIQEKY RILASLVIAQACLE-SNFGQSGLAQKGKNLFGVKGSYNGQSVTMKTTEY-RGGKAYQT DAAFRKYPSWFESLDDLAKLY-VNGVSWDRNKYKPIIGETNYVIACKKVQECGYATD PNYASKLISIIEKYDLT-KYDKVGNKKPVKSAVAAKKEKPQIYIVQKGDTLTA-IAKRYN TSVQNLVKLNNIKNPDLIL-VGQKLRVKLEHHHHHH. In SEQ ID NO: 15 amino acids 1 to 216 correspond to the *Geobacillus* sp. Y4.1MC1 mannosyl-glycoprotein endo-beta-N-acetylglucosaminidase having NCBI accession No. ADP73474.1, and amino acids 217 to 224 correspond to a HisTag.

The amino acid sequence set forth in SEQ ID NO: 16 is MNDFIREIAPFAQRIQEKY RILASLVIAQACLE-SNFGQSGLAQKGKNLFGVKGSYNGQSVTMKTTEY-RGGKAYQT DAAFRKYPSWFESLDDLAKLY-VNGVSWDRNKYKPIIGETNYVIACKKVQECGYATD PNYASKLISIIEKYDLTKYDKVGSSLEHHHHHH. In SEQ ID NO: 16 amino acids 1 to 153 correspond to the thermophile-derived catalytic domain Y4$_{CAT}$; amino acids 154 to 156 are encoded by polynucleotides added to facilitate cloning; and amino acids 157 to 164 correspond to a HisTag.

The amino acid sequence set forth in SEQ ID NO: 17 is MNDFIREIAPFAQRIQEKY RILASLVIAQACLE-SNFGQSGLAQKGKNLFGVKGSYNGQSVTMKTTEY-RGGKAYQT DAAFRKYPSWFESLDDLAKLY-VNGVSWDRNKYKPIIGETNYVIACKKVQECGYATD PNYASKLISIIEKYDLTKYDKVGSSLDGSTQEIFIN-GASQKATENKSFFTNARAKVALD PRSNPSDNYKDLGEIYAEERIQVLAEIC-DREDYLPVKYWKDASGCESSKVWVNANK DYLEIDTNARSFNIVTELDARYEPSVNSKRMGYVKN-NERLYVHRVEGDYVLATYYA GNGYK-TAWFTKEYIIKDLEHHHHHH. In SEQ ID NO: 17 amino acids 1 to 153 correspond to Y4$_{CAT}$, the thermophile-derived catalytic domain; amino acids 154 to 160 are encoded by polynucleotides added to facilitate cloning; amino acids 161 to 319 correspond to the *C. perfringens*-derived C-terminal cell wall binding domain CP10$_{CWB}$; and amino acids 320 to 327 correspond to a HisTag.

The amino acid sequence set forth in SEQ ID NO: 18 is MNDFIREIAPFAQRIQEKR ILASLVIAQACLE-SNFGQSGLAQKGKNLFGVKGSYNGQSVTMKTTEY-RGGKAYQTD AAFRKYPSWFESLDDLAKLY-VNGVSWDRNKYKPIIGETNYVIACKKVQECGYATDP NYASKLISIIEKYDLTKYDKVGSSLER-MLKSIDENIVNDTDTTDVPSSDDSNKKDFSTN ARAL-VALDPRDNPSDNYSDLGEIYKDERFRV-LAEVCDKGDFLPIVYWKDSEGRESGK VWVRSKQDYMMIDTYHKVFN-VITELDARYEPSPNSSRMGYVTNGERLYVHRIEGNY ALATYFAGNGYKTAWFTKKYIEKIVEHHHHHH. In SEQ ID NO: 18 amino acids 1 to 153 correspond to Y4$_{CAT}$, the thermophile-derived catalytic domain; amino acids 154 to 158 are encoded by polynucleotides added to facilitate cloning; amino acids 159 to 328 correspond to the *C. perfringens* derived C-terminal cell wall binding domain CP18$_{CWB}$; and amino acids 328 to 336 correspond to a HisTag.

The amino acid sequence set forth in SEQ ID NO: 19 is MNDFIREIAPFAQRIQEKY RILASLVIAQACLE-SNFGQSGLAQKGKNLFGVKGSYNGQSVTMKTTEY-RGGKAYQT DAAFRKYPSWFESLDDLAKLY-VNGVSWDRNKYKPIIGETNYVIACKKVQECGYATD PNYASKLISIIEKYDLTKYDKVGSSLDGSLSEFKNN-SYRPTGGSSETVVSENGFYTSNE ERTNATIVGKGDI-EVLDEKGKVIQGRHISSLDRVFVLGIYPSRN-HIELIYPGKDEKYHA YISIENYSRLSFDYHMQYKNDDGVTYVWWD-SKNVNVKNHDEELQPHQKASPMYRT NGWLRVTFYRADGNPSDGYVRYEGEQKER-FYRKGKVVNVRTSLTVRAGAGTNYSA IGSLDPNEN-VEILEKTEGWYYIEYNARNERKRGYVSKKYIE-IIQLEHHHHHH. In SEQ ID NO: 19, amino acids 1 to 153 correspond to Y4$_{CAT}$, the thermophile-derived catalytic domain; amino acids 154 to 160 are encoded by polynucleotides added to facilitate cloning; amino acids 161 to 403 correspond to the *C. perfringens* derived C-terminal cell wall binding domain CP33$_{CWB}$; and amino acids 404 to 411 correspond to a HisTag.

The amino acid sequence set forth in SEQ ID NO: 20 is MNDFIREIAPFAQRIQEKY RILASLVIAQACLE-SNFGQSGLAQKGKNLFGVKGSYNGQSVTMKTTEY-RGGKAYQT DAAFRKYPSWFESLDDLAKLY-VNGVSWDRNKYKPIIGETNYVIACKKVQECGYATD PNYASKLISIIEKYDLTKYDKVGSSLDGSED-FLKKDFTLENATTCNVDTELNIRAKGTT GATIVGSI-PAGDRFRIKWVDSDY-LGWYYIEYQGITGYVSQDYVEKLQMATTCNVDSV LNVRAEGNTSSNIVATINPGEVFRIDWVDSD-FIGWYRITTANGANGFVKSDFVKKLLE HHHHHH. In SEQ ID NO: 20, amino acids 1 to 153 correspond to the thermophile-derived catalytic domain Y4$_{CAT}$; amino acids 154 to 160 are encoded by polynucleotides added to facilitate cloning; amino acids 161 to 303 correspond to the *C. perfringens* derived C-terminal cell wall binding domain CP41$_{CWB}$; and amino acids 304 to 311 correspond to a HisTag.

The amino acid sequence set forth in SEQ ID NO: 21 is MNDFIREIAPFAQRIQEKY RILASLVIAQACLE- SNFGQSGLAQKGKNLFGVKGSYNGQSVTMKTTEY- RGGKAYQT DAAFRKYPSWFESLDDLAKLY- VNGVSWDRNKYKPIIGETNYVIACKKVQECGYATD PNYASKLISIIEKYDLTKYDKVGSSLDGSRYLANAID- PNIPLEKEQDYYRVCVQRFTN KEDAEKAQQRISNEL- GYYCFAEKILEHHHHHH. In SEQ ID NO: 21, amino acids 1 to 153 correspond to the thermophile-derived catalytic domain Y4$_{CAT}$; amino acids 154 to 160 are encoded by polynucleotides added to facilitate cloning; amino acids 161 to 213 correspond to the *C. perfringens* derived C-terminal cell wall binding domain CP26F$_{CWB}$; and amino acids 214 to 221 correspond to a HisTag.

The amino acid sequence set forth in SEQ ID NO: 22 is MKKIFWDKGHGGSDPGA VANGLQEKNLTH- KIVEYATDYLAAHYEGFTQRVSREGDQSLTLDQRAD- MANKWGA DVFVSVHINAGKGTGFEIYVHPNASPQ- SIALQNVLHGEILSAMRQFGNITDRGKKRAN YAVLRETKMPAVLTENLFIDSNDAKHLKNEAF- LKAVGEAHARGVAKFLGLKEKQKA QPEAK- PQQKPSDKKLYRVQVGAFADRENAER- LAEELKRKGYPVYITDLEHHHHHH. In SEQ ID NO: 22 amino acids 1 to 233 correspond to *Geobacillus* virus E2 putative N-acetylmuramoyl-L-alanine amidase having NCBI accession No. YP_001285830.1; and amino acids 234 to 241 correspond to a HisTag.

The amino acid sequence set forth in SEQ ID NO:23 is MKKIFWDKGHGGSDPGA VANGLQEKNLTH- KIVEYATDYLAAHYEGFTQRVSREGDQSLTLDQRAD- MANKWGA DVFVSVHINAGKGTGFEIYVHPNASPQ- SIALQNVLHGEILSAMRQFGNITDRGKKRAN YAVLRETKMPAVLTENLFIDSNDAKHLKNEAF- LKAVGEAHARGVAKFLGSSLEHHH HHH. In SEQ ID NO: 23 amino acids 1 to 178 correspond to GVE2$_{CAT}$, the thermophile-derived catalytic domain; amino acids 179 to 181 are encoded by polynucleotides added to facilitate cloning; and amino acids 182 to 189 correspond to a HisTag.

The amino acid sequence set forth in SEQ ID NO: 24 is MKKIFWDKGHGGSDPGA VANGLQEKNLTH- KIVEYATDYLAAHYEGFTQRVSREGDQSLTLDQRAD- MANKWGA DVFVSVHINAGKGTGFEIYVHPNASPQ- SIALQNVLHGEILSAMRQFGNITDRGKKRAN YAVLRETKMPAVLTENLFIDSNDAKHLKNEAF- LKAVGEAHARGVAKFLGSSLDGST QEIFIN- GASQKATENKSFFTNARAK- VALDPRSNPSDNYKDLGEIYAEERIQVLAEICDR EDYLPVKYWKDASGCESSKVWVNANKDYLEIDT- NARSFNIVTELDARYEPSVNSKR MGYVKNNERLY- VHRVEGDYVLATYYAGNGYK- TAWFTKEYIIKDLEHHHHHH. In SEQ ID NO: 24, amino acids 1 to 178 correspond to the thermophile-derived catalytic domain GVE2$_{CAT}$; amino acids 179 to 185 are encoded by polynucleotides added to facilitate cloning; amino acids 186 to 344 correspond to the *C. perfringens* derived C-terminal cell wall binding domain CP10$_{CWB}$; and amino acids 345 to 352 correspond to a HisTag.

The amino acid sequence set forth in SEQ ID NO: 25 is MKKIFWDKGHGGSDPGA VANGLQEKNLTH- KIVEYATDYLAAHYEGFTQRVSREGDQSLTLDQRAD- MANKWGA DVFVSVHINAGKGTGFEIYVHPNASPQ- SIALQNVLHGEILSAMRQFGNITDRGKKRAN YAVLRETKMPAVLTENLFIDSNDAKHLKNEAF- LKAVGEAHARGVAKFLGSSLERML KSIDENIVNDTDTTDVPSSDDSNKKDFSTNARAL- VALDPRDNPSDNYSDLGEIYKDER FRV- LAEVCDKGDFLPIVYWKDSEGRESGKVWVR- SKQDYMMIDTYHKVFNVITELDA RYEPSPNSSRMGYVTNGERLYVHRIEGNYALATYF- AGNGYKTAWFTKKYIEKIVEHH HHH. In SEQ ID NO: 25, amino acids 1 to 178 correspond to the thermophile-derived catalytic domain GVE2$_{CAT}$; amino acids 179 to 183 are encoded by polynucleotides added to facilitate cloning; amino acids 184 to 354 correspond to the *C. perfringens* derived C-terminal cell wall binding domain CP18$_{CWB}$; and amino acids 355 to 361 correspond to a HisTag.

The amino acid sequence set forth in SEQ ID NO: 26 is MKKIFWDKGHGGSDPGA VANGLQEKNLTH- KIVEYATDYLAAHYEGFTQRVSREGDQSLTLDQRAD- MANKWGA DVFVSVHINAGKGTGFEIYVHPNASPQ- SIALQNVLHGEILSAMRQFGNITDRGKKRAN YAVLRETKMPAVLTENLFIDSNDAKHLKNEAF- LKAVGEAHARGVAKFLGSSLDGSLS EFKNN- SYRPTGGSSETVVSENGFYTSNEERTNATIVGKGDI- EVLDEKGKVIQGRHISSL DRVFVLGIYPSRNHIELIYPGKDEKYHAYISIE- NYSRLSFDYHMQYKNDDGVTYYVWW DSKNVNVKNHDEELQPHQKASPMYRTNGWLRVT- FYRADGNPSDGYVRYEGEQKER FYRKGKVVNVRT- SLTVRAGAGTNYSAIGSLDPNENVEILEK- TEGWYYIEYNARNERK RGYVSKKYIE- IIQLEHHHHHH. In SEQ ID NO: 26, amino acids 1 to 178 correspond to the thermophile-derived catalytic domain GVE2$_{CAT}$; amino acids 179 to 185 are encoded by polynucleotides added to facilitate cloning; amino acids 186 to 428 correspond to the *C. perfringens* derived C-terminal cell wall binding domain CP33$_{CWB}$; and amino acids 429 to 436 correspond to a HisTag.

The amino acid sequence set forth in SEQ ID NO: 27 is MKKIFWDKGHGGSDPGA VANGLQEKNLTH- KIVEYATDYLAAHYEGFTQRVSREGDQSLTLDQRAD- MANKWGA DVFVSVHINAGKGTGFEIYVHPNASPQ- SIALQNVLHGEILSAMRQFGNITDRGKKRAN YAVLRETKMPAVLTENLFIDSNDAKHLKNEAF- LKAVGEAHARGVAKFLGSSLDGSE DFLKKDFTLENATTCNVDTELNIRAKGTTGATIVGSI- PAGDRFRIKWVDSDYLGWYYI EYQGITGYVSQDYVEKLQMATTCNVDSVLNVRAE- GNTSSNIVATINPGEVFRIDWVD SDFIGWYRITTAN- GANGFVKSDFVKKLLEHHHHHH. In SEQ ID NO: 27, amino acids 1 to 178 correspond to the thermophile-derived catalytic domain GVE2$_{CAT}$; amino acids 179 to 185 are encoded by polynucleotides added to facilitate cloning; amino acids 186 to 328 correspond to the *C. perfringens* derived C-terminal cell wall binding domain CP41$_{CWB}$; and amino acids 329 to 336 correspond to a HisTag.

The amino acid sequence set forth in SEQ ID NO: 28 is MGMKKIFWDKGHGGSDP GAVANGLQEKNLTH- KIVEYATDYLAAHYEGFTQRVSREGDQSLTLDQRAD- MANKW GADVFVSVHINAGKGTGFEIYVHPNASPQ- SIALQNVLHGEILSAMRQFGNITDRGKKR ANYAVLRETKMPAVLTENLFIDSNDAKHLKNEAF- LKAVGEAHARGVAKFLGRYLAN AIDPNI- PLEKEQDYYRVCVQRFTNKEDAEKAQQRISNEL- GYYCFAEKILEHHHHHH. In SEQ ID NO:28 amino acids 1 to 234 correspond to PlyGVE2CpCWB, the published version of GVE2$_{CAT}$-CP26F$_{CWB}$.

Proteins were expressed in BL21 (DE3) *E. coli* and purified by their 6× HisTag using nickel affinity chromatography. Purity of over 95% was apparent in the SDS-PAGE from each of the recombinant proteins. All proteins migrated in the SDS-PAGE gel as expected from their predicted molecular weight (MW). Y412$_{CAT}$ ran at 20.6 kDa; Y412$_{CAT}$-CP10$_{CWB}$ ran at 39.4 kDa; Y412$_{CAT}$-CP18$_{CWB}$ ran at 40.5 kDa; Y412$_{CAT}$-CP33$_{CWB}$ ran at 49.2 kDa; Y412$_{CAT}$-CP41$_{CWB}$ ran at 37 kDa; Y412$_{CAT}$-CP26F$_{CWB}$ ran at 27.3 kDa; and PlyGspY412 ran at 25.9 kDa; Y4$_{CAT}$ ran at 18.7 kDa; Y4$_{CAT}$-CP10$_{CWB}$ ran at 37.4 kDa; Y4$_{CAT}$-CP18$_{CWB}$ ran at 38.6 kDa; Y4$_{CAT}$-CP33$_{CWB}$ ran at 47.3 kDa; Y4$_{CAT}$-CP41$_{CWB}$ ran at 35 kDa; Y4$_{CAT}$-CP26F$_{CWB}$ ran at 27.4 kDa; PlyGspY4 ran at 25.4 kDa; Gve2$_{CAT}$ ran at 20.9 kDa; Gve2$_{CAT}$-CP10$_{CWB}$ ran at 39.7 kDa; Gve2$_{CAT}$-CP18$_{CWB}$ ran at 40.8 kDa; Gve2$_{CAT}$-CP33$_{CWB}$ ran at 49.5 kDa; Gve2$_{CAT}$-CP41$_{CWB}$ ran at 37.3 kDa; Gve2$_{CAT}$-CP26F$_{CWB}$ ran at 27.3 kDa; and PlyGVE2 ran at 27 kDa.

Example 2

Lytic Activity of Chimeric Recombinant Lysins

The lytic activity of the chimeric recombinant lysins was determined by turbidity reduction assay. Of the chimeric recombinant lysins Y412$_{CAT}$-CP33$_{CWB}$, Y412$_{CAT}$-CP18$_{CWB}$, Y4$_{CAT}$-CP41$_{CWB}$, and GVE2$_{CAT}$-CP18$_{CWB}$, GVE2$_{CAT}$-CP33$_{CWB}$ and GVE2$_{CAT}$-CP33$_{CWB}$ presented with the highest rate of lytic activity.

Briefly, recombinant chimeric lysins were diluted into 50 mM NaH$_2$PO$_4$ pH 7.0 and mixed 1:1 with mid-log phase *C. perfringens* cells (strain CP39) in water. The assay was conducted in a 96-well plate, using a Molecular Devices (San Jose, Calif., U.S.A.) plate reader. Turbidity was read as optical density (OD) at 600 nm over 20 minutes. The decrease in OD represents lysis of cells in suspension. Final enzyme concentration was 0.005 mg/ml.

A graph of a lysis activity time course for PlyGSPY412; $Y412_{CAT}$; and chimeric recombinant lysins comprising $Y412_{CAT}$ is shown in FIG. 4. As shown in this figure, $Y412_{CAT}$-$CP33_{CWB}$ had the steepest curve, indicating the highest rate of turbidity reduction. When arranged in order from highest lytic activity to lowest lytic activity, the lytic activity was as follows: $Y412_{CAT}$-$CP33_{CWB}$>$Y412_{CAT}$-$CP18_{CWB}$>$Y412_{CAT}$-$CP41_{CWB}$>$Y412_{CAT}$-$CP10_{CWB}$>$Y412_{CAT}$-$CP26F_{CWB}$ (Y412-26F). PlyGspY412 and $Y412_{CAT}$ were inactive against CP39 cells, as seen by their lines adjacent to the buffer control line at the top of the plot in FIG. 4.

Testing of the PlyGspY4 derived catalytic domain, $Y4_{CAT}$, and its fusion proteins was done by standard turbidity reduction assay. As seen in FIG. 5, lytic activity was as follows (highest to lowest): $Y4_{CAT}$-$CP41_{CWB}$>$Y4_{CAT}$-$CP33_{CWB}$>$Y4_{CAT}$-$CP18_{CWB}$>$Y4_{CAT}$-$CP10_{CWB}$. PlyGspY4; $Y4_{CAT}$; and $Y4_{CAT}$-$CP26F_{CWB}$ were inactive against CP39 cells, as seen by their lines adjacent to the buffer control line at the top of the plot in FIG. 5.

The degree of lytic activity of the recombinant lysins derived from PlyGVE2; harboring the $GVE2_{CAT}$ (the amidase catalytic domain) are shown in FIG. 6. $GVE2_{CAT}$-$CP41_{CWB}$ and $GVE2_{CAT}$-$CP33_{CWB}$ had the steepest curves, indicating highest rate of turbidity reduction. Lytic activity was as follows (highest to lowest): $GVE2_{CAT}$-$CP41_{CWB}$>$GVE2_{CAT}$-$CP33_{CWB}$>$GVE2_{CAT}$-$CP18_{CWB}$>$GVE2_{CAT}$-$CP10_{CWB}$>PlyGVE2CpCWB. The parental lysin PlyGVE2 and its catalytic domain $GVE2_{CAT}$ had trace to very low activity against CP39 cells, as seen by their lines being close to the buffer control line at the top of the plot in FIG. 6.

Example 3

Spot Lysis Assay

All chimeric recombinant lysins comprising $Y412_{CAT}$; $Y4_{CAT}$; or $GVE2_{CAT}$ catalytic domains and a cell wall binding domain from PlyCP10, PlyCP18, PlyCP33, PlyCP41, or PlyCP26F showed lysing activity when in a plate lysis assay.

The plate lysis (spot on lawn) assay was essentially as described by Becker et al. (2009. "*LysK CHAP endopeptidase domain is required for lysis of live staphylococcal cells*," FEMS Microbiol. Lett. 294:52-60). *C. perfringens* cultures were propagated to mid-log phase ($OD_{600}$=0.4-0.6) in 100 mL Brain Heart Infusion+yeast extract+cysteine (BYC) media. Cells were harvested via centrifugation at 5,000 g for 30 minutes, resuspended in 2 mL PBS 25% glycerol, and stored at −80° C. until needed. The frozen cell pellet was thawed on ice and washed with 10 mL sterile $H_2O$. The cells were then washed once with 0.5×lysin buffer A (50 mM $NH_4OAc$, 10 mM $CaCl_2$, 1 mM DTT, pH 6.2) and then a final time with 10 mL 1× lysin buffer A and pelleted again. The cells were suspended in 1.0 mL lysin buffer A. Twelve milliliters of melted 50° C. semisolid BYC agar (BYC media with 7 g agar per liter, autoclaved 20 minutes) were added to the cells and then the mixture was poured into a sterile square petri dish. This mixture was allowed to sit 20 minutes at room temperature to solidify and then 10 μg of the Nickel chromatography-purified chimeric recombinant lysin was spotted in 5 μL onto the plate. The plate was incubated in an anaerobic chamber for 2 hours at 37° C. before scoring for clear zones. After incubation at 37° Celsius, active lysins create a clear zone in the turbidity of the embedded cells.

All chimeric lysins fused to a cell wall binding domain had activity. Chimeric recombinant lysins comprising the binding domains from PlyCP18, PlyCP33, and PlyCP41 appeared most active. Whereas, the chimeric recombinant lysin comprising the binding domain from PlyCP26F had low to miniscule activity in this assay. However, the catalytic domains without a binding domain were not active and did not create clear zones. The $GVE2_{CAT}$-$CP10_{CWB}$ fusion displayed a white discoloration on the plate, which may represent protein precipitation.

Example 4

Activity and Thermostability of $GVE2_{CAT}$-$CP18_{CWB}$

The chimeric recombinant lysin $GVE2_{CAT}$-$CP18_{CWB}$ displayed improved activity and thermostability compared to native lysin PlyCP18 when tested in parallel and under identical conditions.

The enzymes were incubated at 4° C.; 50° C.; 60° C.; or 70° C. for 15 minutes, placed on ice for 10 minutes, mixed 1:1 with Cp39 cells in turbidity reduction assay buffer, and assayed for residual activity by turbidity reduction at 22° C. The change in optical density was measured over time. FIG. 7A shows the results obtained for PlyCP18; and FIG. 7B shows the results obtained for $GVE2_{CAT}$-$CP18_{CWB}$. The chimeric recombinant lysin $GVE2_{CAT}$-$CP18_{CWB}$ displayed substantially greater lytic activity and thermostability compared to PlyCP18 when tested under identical conditions, in parallel.

Example 5

Thermostability of Thermophile-Derived Lysins

The thermophile-derived chimeric recombinant lysins are more tolerant of heating than the mesophile-derived PlyCP18 lysin.

Figure 8:
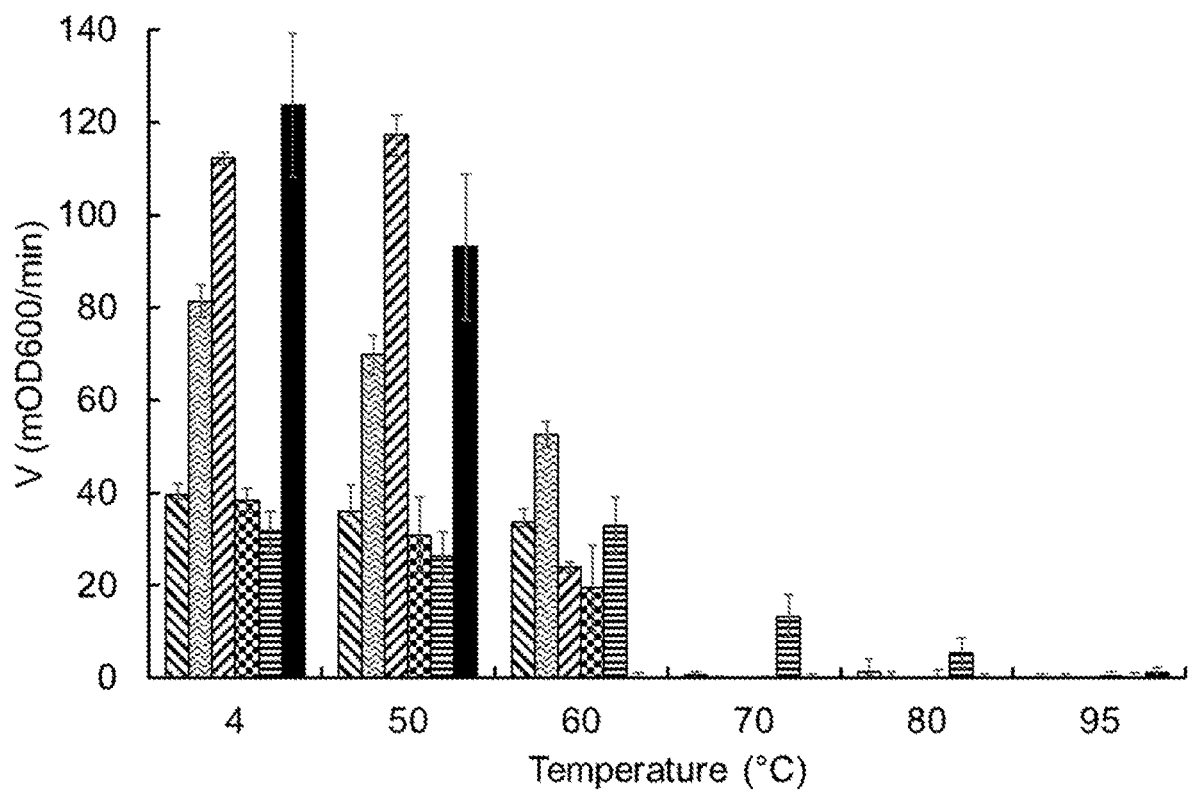
Figure 9:
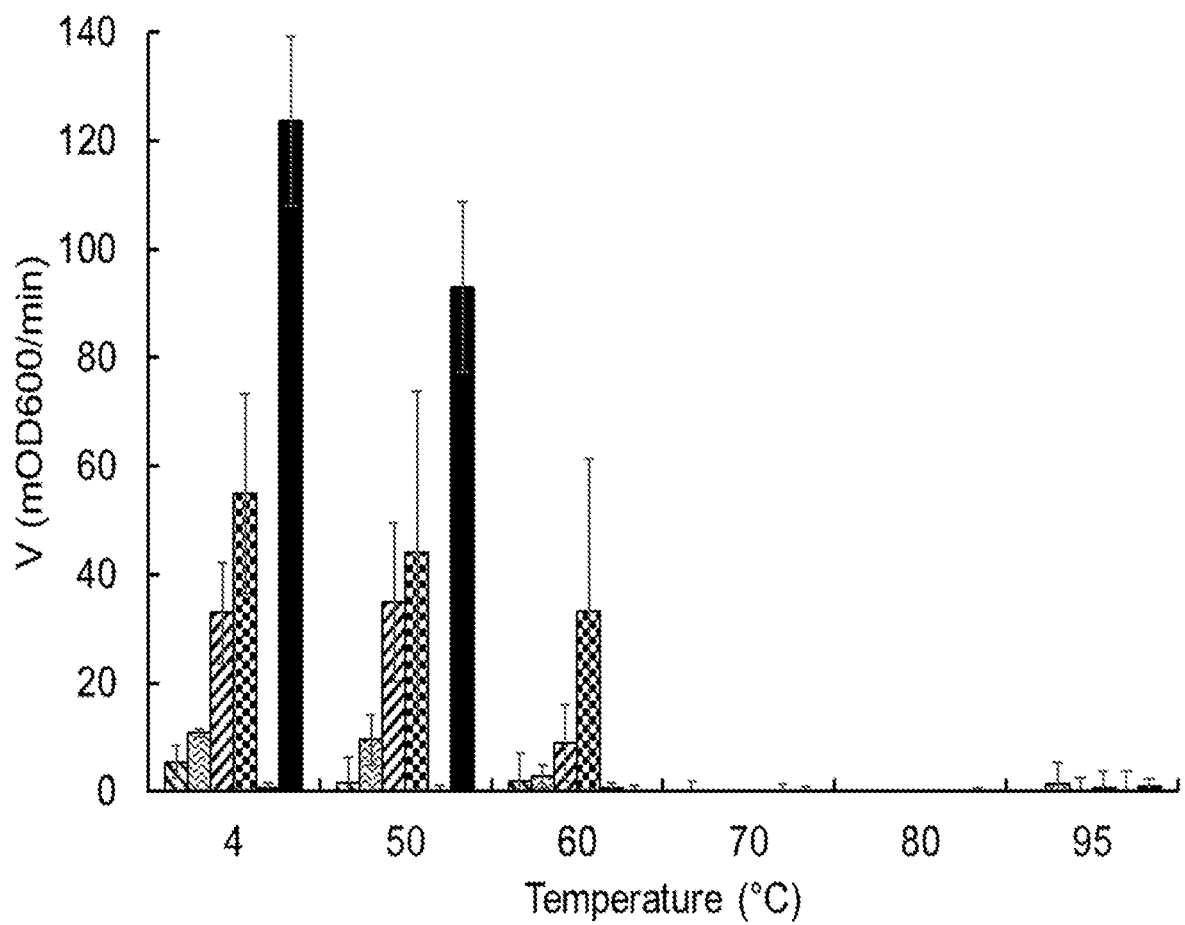

Enzymes were incubated at 4° C.; 50° C.; 60° C.; 70° C.; 80 C; or 95 C for 15 minutes. After this time the enzymes were placed on ice for 10 minutes, followed by mixing the enzymes 1:1 with Cp39 cells. Residual enzyme activity was assayed by turbidity reduction at 22° C. The results are shown in FIG. 8; FIG. 9; and FIG. 10. As seen on FIG. 8, PlyCP18 lost activity after incubation at 60° C., but all the chimeric recombinant lysins comprising Y412$_{CAT}$ retained substantial activity after the same heat challenge. One of the chimeric recombinant lysins, Y412$_{CAT}$-CP26F$_{CWB}$, retained activity after heat treatment at 70° C. As seen on FIG. 9, of the chimeric recombinant lysins comprising Y4$_{CAT}$ only Y4$_{CAT}$-CP41$_{CWB}$ retained substantial activity after incubation at 60° C.

Figure 10:
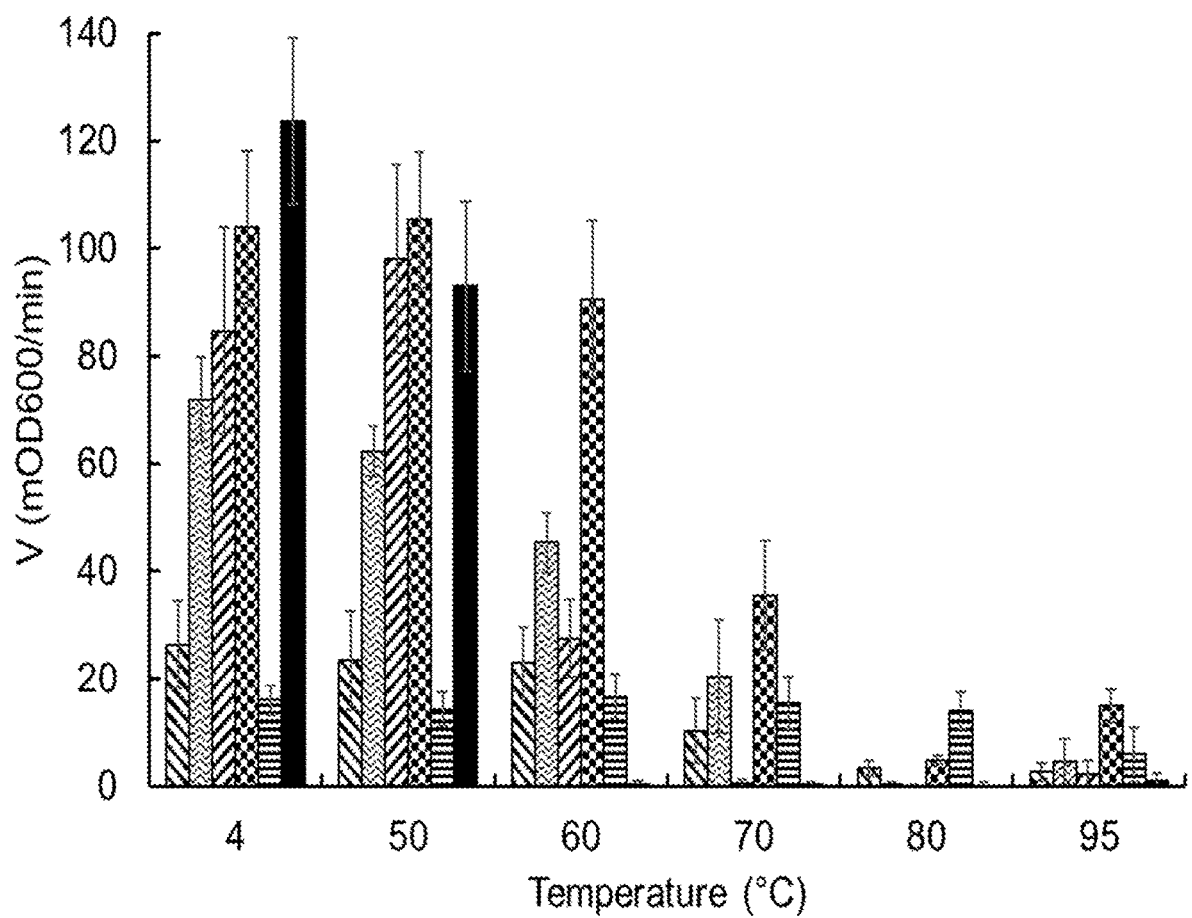

As seen on FIG. 10 the chimeric recombinant lysins comprising GVE2$_{CAT}$ showed activity with substantial thermostability. After being kept at 4° C., all of the new chimeric recombinant lysins had greater activity than the published chimeric recombinant lysin, PlyGVE2CpCWB; which under current nomenclature is GVE2$_{CAT}$-CP26F$_{CWB}$. All of the chimeric recombinant lysins comprising GVE2$_{CAT}$ showed activity after incubation at 60° C.

Most of the chimeric recombinant lysins comprising GVE2$_{CAT}$ showed activity even after heating at 95° C. GVE2$_{CAT}$-CP10$_{CWB}$, GVE2$_{CAT}$-CP18$_{CWB}$, GVE2$_{CAT}$-CP41$_{CWB}$, and the published fusion PlyGVE2CpCWB (GVE2$_{CAT}$-CP26F$_{CWB}$) showed activity after 70° C. heat treatment. The improved thermostability of the chimeric recombinant lysins should make them more tolerant of heat treatments used in production of animal feed pellets. It is apparent from these experiments that all $_{CWB}$'s are not equivalent in their ability to redirect the thermophile lysins regardless of heat treatment.

Example 6

Lysin Activity Against Different Bacteria

The recombinant chimeric lysins of the invention are active on five C. perfringens strains but are not active on multiple Gram-positive bacteria from other genera.

Examination of the activity of PlyGVE2, PlyGspY412, PlyGspY4, their catalytic domains $GVE2_{CAT}$, $Y4_{CAT}$, and $Y412_{CAT}$, and the chimeric recombinant lysins $GVE2_{CAT}$-$CP10_{CWB}$, $GVE2_{CAT}$-$CP18_{CWB}$, $GVE2_{CAT}$-$CP33_{CWB}$, $GVE2_{CAT}$-$CP41_{CWB}$, $GVE2_{CAT}$-$CP26F_{CWB}$, $Y4_{CAT}$-$CP41_{CWB}$ $Y4_{CAT}$-$CP10_{CWB}$, $Y4_{CAT}$-$CP18_{CWB}$, $Y4_{CAT}$-$CP33_{CWB}$, $Y4_{CAT}$-$CP41_{CWB}$, $Y412_{CAT}$-$CP10_{CWB}$, $Y412_{CAT}$-$CP18_{CWB}$, $Y412_{CAT}$-$CP33_{CWB}$, $Y412_{CAT}$-$CP41_{CWB}$; and $Y412_{CAT}$-$CP26F_{CWB}$ lysins against different strains of *C. perfringens* and different species of bacteria was done by turbidity reduction assay with the lysins at 0.005 mg/mL concentration. Three of the five *C. perfringens* strains tested are poultry-derived strains (Cp39, Cp509, Cp734) and the remaining two are swine isolates (JGS1504 and JGS1659). Except for Cp39, these strains were isolated from animals suffering from necrotic enteritis.

For this example, lytic activity was determined by turbidity reduction assay using 0.005 mg/ml lysin with suspensions of the indicated bacteria in reaction buffer. Vnet is the velocity of the lysis reaction minus the background decrease in turbidity. Stdev is the standard deviation of the replicates. Convert to +− values as follows: "−" when Vnet−Stdev<=5, "+/−" when Vnet−Stdev>5 and <=15, "+" when Vnet−Stdev>15 and <=45, "++" when Vnet−Stdev>45, <=135, "+++" when Vnet−Stdev>135, where "Vnet" is the maximal velocity (V in milliOD600/minute) of the reaction minus the velocity from the buffer control reaction, and where "Stdev" is the standard deviation from the replicate reactions.

None of the parental thermophile lysin PlyGspY4, its catalytic domain $Y4_{CAT}$, and the catalytic domain $Y412_{CAT}$ had activity against the five tested *C. perfringens* strains. The parental thermophile lysins PlyGspY412, PlyGVE2, and the catalytic domain $GVE2_{CAT}$ had no to very low activity against the five tested *C. perfringens* strains.

The killing capability against *C. perfringens* improved drastically when $GVE2_{CAT}$ was fused to the cell wall binding domain from *C. perfringens* endolysins PlyCP10, PlyCP18, PlyCP33, PlyCP41, and PlyCP26F. The results of testing these lysins against various bacteria can be seen in Table 2, below. Interestingly, while PlyGVE2 and $GVE2_{CAT}$ had some activity against non-*C. perfringens* bacteria, the fusion proteins with the *C. perfringens* (*CP*) cell wall binding domains did not kill any of the other species tested. This shows that addition of a CP cell wall binding domain increased the activity against *C. perfringens*, and reduced the non-specificity against other species of bacteria. The chimeric recombinant lysins $GVE2_{CAT}$-$CP18_{CWB}$, $GVE2_{CAT}$-$CP33_{CWB}$, and $GVE2_{CAT}$-$CP41_{CWB}$, all had greater killing activity against all five of the *C. perfringens* strains tested than $GVE2_{CAT}$-$CP26F_{CWB}$ (published as PlyGVE2CpCWB by Swift, S. M., et al., 2015, "*A Thermophilic Phage Endolysin Fusion to a Clostridium perfringens-Specific Cell Wall Binding Domain Creates an Anti-Clostridium Antimicrobial with Improved Thermostability*," Viruses 7(6): 3019-3034). The chimeric recombinant lysin $GVE2_{CAT}$-$CP10_{CWB}$ did not kill Cp39 cells, whereas PlyGVE2CpCWB could weakly kill this strain under these conditions (lysin at 0.005 mg/mL).

The parental thermophile lysin PlyGspY412 had little to no activity against the five *C. perfringens* tested, its catalytic domain $Y412_{CAT}$ showed no detectable activity against any of the five *C. perfringens* tested. The chimeric recombinant lysins $Y412_{CAT}$-$CP10_{CWB}$, $Y412_{CAT}$-$CP18_{CWB}$, $Y412_{CAT}$-$CP33_{CWB}$, $Y412_{CAT}$-$CP41_{CWB}$; and $Y412_{CAT}$-$CP26F_{CWB}$ presented with higher activity against the *C. perfringens* bacteria strains tested, and presented no activity against non-*C. perfringens* bacteria.

Chimeric recombinant lysins comprising $Y4_{CAT}$ displayed overall reduced activity compared to the other chimeric recombinant lysins tested. The recombinant lysins $Y4_{CAT}$-$CP10_{CWB}$, $Y4_{CAT}$-$CP18_{CWB}$, $Y4_{CAT}$-$CP33_{CWB}$, and $Y4_{CAT}$-$CP41_{CWB}$ all had activity against the five *C. perfringens* strains tested. $Y4_{CAT}$-$CP26F_{CWB}$ had poor lytic activity against Cp509, and was not active against the other four *C. perfringens* strains tested.

TABLE 2

Lysin activity by turbidity reduction assay against different bacteria

| | Clostridium perfringens | | | | | Other bacteria species | | | | |
|---|---|---|---|---|---|---|---|---|---|---|
| | | | | | | Bacillus | E. | C. | | S. |
| Lysin | Cp39 | Cp509 | Cp734 | Cp JGS1504 | Cp JGS1659 | cereus 17 | faecalis 17 | difficile 700057* | S. agalactiae | aureus 305 |
| GVE2$_{CAT}$ - CP10$_{CWB}$ | − | + | ++ | ++ | ++ | − | − | − | − | − |
| GVE2$_{CAT}$ - CP18$_{CWB}$ | ++ | ++ | ++ | ++ | ++ | − | − | − | − | − |
| GVE2$_{CAT}$ - CP33$_{CWB}$ | ++ | ++ | ++ | +++ | ++ | − | − | − | − | − |
| GVE2$_{CAT}$ - CP41$_{CWB}$ | ++ | ++ | ++ | +++ | ++ | − | − | − | − | − |
| GVE2$_{CAT}$ - CP26F$_{CWB}$ | +/− | + | + | + | + | − | − | − | − | − |
| GVE2$_{CAT}$ | +/− | +/− | +/− | +/− | +/− | +/− | − | +/− | − | − |
| PlyGVE2 | +/− | − | − | +/− | +/− | + | − | − | − | +/− |
| Y4$_{CAT}$ - CP10$_{CWB}$ | +/− | + | + | + | + | − | − | − | − | − |
| Y4$_{CAT}$ - CP18$_{CWB}$ | + | + | +/− | + | + | − | − | − | − | − |
| Y4$_{CAT}$ - CP33$_{CWB}$ | + | + | +/− | + | + | − | − | − | − | − |
| Y4$_{CAT}$ - CP41$_{CWB}$ | ++ | + | +/− | ++ | ++ | − | − | +/− | − | − |
| Y4$_{CAT}$ - CP26F$_{CWB}$ | − | +/− | − | − | − | − | − | − | − | − |
| Y4$_{CAT}$ | − | − | − | − | − | +/− | − | − | − | − |
| PlyGspY4 | − | − | − | − | − | + | − | − | − | − |
| Y412$_{CAT}$ - CP10$_{CWB}$ | + | + | ++ | + | + | − | − | − | − | − |
| Y412$_{CAT}$ - CP18$_{CWB}$ | ++ | + | ++ | ++ | ++ | − | − | − | − | − |
| Y412$_{CAT}$ - CP33$_{CWB}$ | ++ | + | ++ | ++ | ++ | − | − | − | − | − |
| Y412$_{CAT}$ - CP41$_{CWB}$ | + | + | +/− | ++ | + | − | − | − | − | − |
| Y412$_{CAT}$ - CP26F$_{CWB}$ | + | + | + | + | + | − | − | − | − | − |
| Y412$_{CAT}$ | − | − | − | − | − | +/− | − | − | − | − |
| PlyGspY412 | − | − | +/− | − | +/− | ++ | − | − | − | +/− |

Cp, C. perfringens; Bc, Bacillus cereus; Sa, Staphylococcus aureus; Ef, Enterococcus faecalis; S. agal, Streptococcus agalactiae.

Other chimeric recombinant lysins were prepared using the cell wall binding domains from PlyCP18, PlyCP33, and PlyCP26F with the catalytic domains from PlyGvu (NCBI accession WP_084177458), PlyCth (NCBI accession YP_001038028), T7L (T7 lysozyme from pLysS, Novagen), Ph2119 (NCBI accession AHF20915), and Ts2631 (NCBI accession AIM47292). T7 lysozyme (T7L) has been well studied, and has displayed resistance to heat challenges (Sharma M. et al. 2016, "*Elucidating the pH-Dependent Structural Transition of T7 Bacteriophage Endolysin*, Biochemistry 55(33): 4614-4625). Ph2119 and Ts2631 have both been published as thermostable lysins (Plotka et al. 2014, Plotka et al. 2015). The catalytic domain of PlyGvu has homology to endopeptidases and the catalytic domains of PlyCth, T7L, Ph2119, and Ts2631 have homology to amidases.

Listed below, in Table 3, are examples of chimeric recombinant lysins prepared using the catalytic domain from PlyGvu endolysin, PlyCth endolysin, T7L lysin/lysozyme, Ph2119 lysin, or Ts2631 lysin with a cell binding domain from CP18, CP33, or CP26F. These chimeric recombinant lysins failed due to issues with expression, or simply lacked activity against *C. perfringens.*

The recombinant polypeptides expressed by $Cth_{CAT}$-$CP18_{CWB}$-pET21a and $Cth_{CAT}$-$CP33_{CWB}$-pET21a were not soluble, and were not used in *C. perfringens* activity assays. The recombinant products $Gvu_{CAT}$-$CP18_{CWB}$-pET21a, T7L-$CP18_{CWB}$-pET21a, T7L-$26F_{CWB}$-pET21a, Ph2119-$CP18_{CWB}$-pET21a, Ph2119-$26F_{CWB}$-pET21a, Ts2631-$CP18_{CWB}$-pET21a, and Ts2631-$26F_{CWB}$-pET21a were soluble, but did not have activity against *C. perfringens.*

TABLE 3

Other Chimeric Recombinant Lysins

| Fusion Plasmid DNAs made | Protein abbreviation | Protein expressed | Protein soluble | Protein active vs. *C. perfringens* |
|---|---|---|---|---|
| $Gvu_{CAT}$-$CP18_{CWB}$-pET21a | Gvu-18 | Yes | Yes | No |
| $Cth_{CAT}$-$CP18_{CWB}$-pET21a | Cth-18 | Yes | No | n.a. |
| $Cth_{CAT}$-$CP33_{CWB}$-pET21a | Cth-33 | Yes | No | n.a. |
| T7L-$CP18_{CWB}$-pET21a | T7L-18 | Yes | Yes | No |
| T7L-$26F_{CWB}$-pET21a | T7L-26F | Yes | Yes | No |
| Ph2119-$CP18_{CWB}$-pET21a | Ph2119-18 | Yes | Yes | No |
| Ph2119-$26F_{CWB}$-pET21a | Ph2119-26F | Yes | Yes | No |
| Ts2631-$CP18_{CWB}$-pET21a | Ts2631-18 | Yes | Yes | No |
| Ts2631-$26F_{CWB}$-pET21a | Ts2631-26F | Yes | Yes | No |

Additionally, other chimeric recombinant lysins were prepared using mesophile lysin catalytic domains from VD13, Ply118, LysK, and 2638A endolysins and *C. perfringens* cell wall binding domains. These chimeric recombinant lysins were expressed and purified, but had no activity against *C. perfringens* under our standard assay conditions. It is possible that trace activity of these non-functional chimeras may be present when using amounts of protein orders of magnitude higher in the assays than used for the active lysins presented above.

Example 7

Minimal Inhibitory Concentration Assays

Using micro-broth Minimal Inhibitory Concentration (MIC) assays, recombinant chimeric lysins Y4$_{CAT}$-CP33$_{CWB}$ and Y4$_{CAT}$-CP41$_{CWB}$ displayed better activity than the comparable Y412$_{CAT}$-CP33$_{CWB}$; Y412$_{CAT}$-CP41$_{CWB}$; GVE2$_{CAT}$-CP33$_{CWB}$; and GVE2$_{CAT}$-CP41$_{CWB}$.

*Clostridium perfringens* strain Cp39 was grown to mid-log phase in BYCT broth (37 g/L Brain heart infusion+5 g/L Yeast extract+0.5 g/L Cystiene+0.5 g/L sodium Thioglycolate+1 dH2O). The chimeric recombinant lysins in PBS 25% glycerol (filter sterile) were two-fold serial diluted with BYCT broth (0.1 ml+0.1 ml) across the row of a 96-well plate. Cp39 cells were diluted to ~$8\times10^5$ cells/ml in BYCT broth and 0.1 ml cells were added to the chimeric recombinant lysins. The highest concentration for all lysins tested was 100 micrograms per milliliter with 0.4 mg/ml lysin diluted four-fold after the addition of cells in the first well of each row. Serial diluted PBS 25% glycerol served as the buffer control. The 96-well plate was incubated in an anaerobic chamber at 37° C. for 20 to 24 hours before being read for absorbance at 600 nm (A600) in a plate reader. The MIC value is the lowest concentration of lysin that creates a visually clear well in the dilution series. Estimated cell counts were determined by five-fold serial dilutions (n=4) of the Cp39 cells across the row of a 96-well plate (0.05 ml cells+0.2 ml broth). After incubation at 37° C. for 20-24 hours, the initial cell concentration was calculated from the last turbid well in the row (>=1 cell).

Table 4, below, shows the MIC obtained at three different times for $GVE2_{CAT}$-$CP33_{CWB}$ (G-33); $GVE2_{CAT}$-$CP41_{CWB}$ (G-41); $Y412_{CAT}$-$CP33_{CWB}$(412-33); $Y412_{CAT}$-$CP41_{CWB}$ (412-41); $Y4_{CAT}$-$CP33_{CWB}$ (4-33); and $Y4_{CAT}$-$CP41_{CWB}$ (4-41). Measurements were obtained on Feb. 8, 2019; Mar. 21, 2019; and Mar. 26, 2019.

TABLE 4

Minimal Inhibitory Concentrations

| Assay Date | G-33 | G-41 | 412-33 | 412-41 | 4-33 | 4-41 | Cell Count (cells/ml) |
|---|---|---|---|---|---|---|---|
| Feb. 8, 2019 | >100 | >100 | >100 | >100 | 100 | 6.3 | 1.0E+06 |
| Mar. 21, 2019 | >100 | >100 | >100 | >100 | 25 | 1.6 | 1.3E+06 |
| Mar. 26, 2019 | >100 | >100 | >100 | >100 | 50 | 1.6 | 1.2E+05 |
| Average MIC (μg/ml) | >100 | >100 | >100 | >100 | 58 | 3 | 8.1E+05 |
| StDev | | | | | 38 | 3 | 6.2E+05 |
| Range | >100 | >100 | >100 | >100 | 25-100 | 1.6-6.3 | |

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention. All references cited herein are incorporated by reference in their entirety.

We claim:

1. A polynucleotide encoding a chimeric recombinant lysin, comprising:
   [I] a first nucleic acid molecule encoding at least one thermophile endolysin catalytic domain from:
      [i] PlyGspY412 as set forth in SEQ ID NO: 4, or a variant thereof having at least 90% sequence identity to SEQ ID NO: 4;
      [ii] PlyGspY4 as set forth in SEQ ID NO: 16, or a variant thereof having at least 90% sequence identity to SEQ ID NO: 16; or
      [iii] PlyGve2 as set forth in SEQ ID NO: 23, or a variant thereof having at least 90% sequence identity to SEQ ID NO: 23;
   [II] a second nucleic acid molecule encoding at least one cell wall binding domain from C. perfringens endolysins:
      [a] PlyCP10 as set forth in SEQ ID NO: 5, or a variant thereof having at least 90% sequence identity to SEQ ID NO: 5;
      [b] PlyCP18 as set forth in SEQ ID NO: 6, or a variant thereof having at least 90% sequence identity to SEQ ID NO: 6;

[c] PlyCP33 as set forth in SEQ ID NO: 7, or a variant thereof having at least 90% sequence identity to SEQ ID NO: 7;

[d] PlyCP41 as set forth in SEQ ID NO: 8, or a variant thereof having at least 90% sequence identity to SEQ ID NO: 8; or

[e] PlyCP26 as set forth in SEQ ID NO: 9, or a variant thereof having at least 90% sequence identity to SEQ ID NO: 9;

[III] optionally a third nucleic acid molecule encoding a linker between the thermophile endolysin catalytic domain and the cell wall binding domain; and

[IV] optionally a fourth nucleic acid molecule encoding a polyhistidine tag, wherein the chimeric recombinant lysin is not a fusion of PlyGve2 and PlyCP26.

2. The polynucleotide of claim 1, wherein the thermophile endolysin catalytic domain is from PlyGspY412 and the cell wall binding domain is from *C. perfringens* endolysins PlyCP10, PlyCP18, PlyCP33, PlyCP41, or PlyCP26.

3. The polynucleotide of claim 1, wherein the thermophile endolysin catalytic domain is from PlyGspY4 and the cell wall binding domain is from *C. perfringens* endolysins PlyCP10, PlyCP18, PlyCP33, PlyCP41, or PlyCP26.

4. The polynucleotide of claim 1, wherein the thermophile endolysin catalytic domain is from PlyGVE2 and the cell wall binding domain is selected from *C. perfringens* endolysins PlyCP10, PlyCP18, PlyCP33, PlyCP41, and PlyCP26; and wherein the chimeric recombinant lysin does not have an amino acid sequence of SEQ ID NO: 28.

5. The polynucleotide of claim 1, wherein the chimeric recombinant lysin comprises a polynucleotide encoding a polyhistidine tag with an amino acid sequence of SEQ ID NO: 1 or SEQ ID NO: 2.

6. The polynucleotide of claim 1, wherein:

the thermophile endolysin catalytic domain has the amino acid sequence of SEQ ID NO: 4; SEQ ID NO: 16; or SEQ ID N: 23;

the cell wall binding domain has the amino acid sequence of SEQ ID NO: 5; SEQ ID NO: 6; SEQ ID NO: 7; SEQ ID NO: 8; or SEQ ID NO: 9; and wherein the chimeric recombinant lysin does not have an amino acid sequence as set forth in SEQ ID NO: 28.

7. The polynucleotide of claim 1, wherein the chimeric recombinant lysin has an amino acid sequence selected from the group consisting of SEQ ID NO: 10; SEQ ID NO: 11; SEQ ID NO: 12; SEQ ID NO: 13; SEQ ID NO: 14; SEQ ID NO: 17; SEQ ID NO: 18; SEQ ID NO: 19; SEQ ID NO: 20; SEQ ID NO: 21; SEQ ID NO: 24; SEQ ID NO: 25; SEQ ID NO: 26; and SEQ ID NO: 27.

8. A nucleic acid construct comprising the polynucleotide of claim 1 operably linked to a promoter.

9. A vector comprising the polynucleotide of claim 1.

10. A host cell comprising the polynucleotide of claim 1.

11. The host cell of claim 10, wherein the host cell is selected from the group consisting of a bacterial cell, a fungal cell, a plant cell, and a mammalian cell.

12. A chimeric recombinant lysin polypeptide comprising:
[I] at least one thermophile endolysin catalytic domain from:

[i] PlyGspY412 as set forth in SEQ ID NO: 4, or a variant thereof having at least 90% sequence identity to SEQ ID NO: 4;

[ii] PlyGspY4 as set forth in SEQ ID NO: 16, or a variant thereof having at least 90% sequence identity to SEQ ID NO: 16; or

[iii] PlyGve2 as set forth in SEQ ID NO: 23, or a variant thereof having at least 90% sequence identity to SEQ ID NO: 23;

[II] at least one cell wall binding domain from *C. perfringens* endolysins:

[a] PlyCP10 as set forth in SEQ ID NO: 5, or a variant thereof having at least 90% sequence identity to SEQ ID NO: 5;

[b] PlyCP18 as set forth in SEQ ID NO: 6, or a variant thereof having at least 90% sequence identity to SEQ ID NO: 6;

[c] PlyCP33 as set forth in SEQ ID NO: 7, or a variant thereof having at least 90% sequence identity to SEQ ID NO: 7;

[d] PlyCP41 as set forth in SEQ ID NO: 8, or a variant thereof having at least 90% sequence identity to SEQ ID NO: 8; or

[e] PlyCP26 as set forth in SEQ ID NO: 9, or a variant thereof having at least 90% sequence identity to SEQ ID NO: 9;

[III] optionally a third nucleic acid molecule encoding a linker between the thermophile endolysin catalytic domain and the cell wall binding domain; and

[IV] optionally a fourth nucleic acid molecule encoding a polyhistidine tag, wherein the chimeric recombinant lysin polypeptide is not a fusion of PlyGve2 and PlyCP26.

13. The chimeric recombinant lysin polypeptide of claim 12, wherein the thermophile endolysin catalytic domain is from PlyGspY412 and the cell wall binding domain is from *C. perfringens* endolysins PlyCP10, PlyCP18, PlyCP33, PlyCP41, or PlyCP26.

14. The chimeric recombinant lysin polypeptide of claim 12, wherein the thermophile endolysin catalytic domain is from PlyGspY4, and the cell wall binding domain is from *C. perfringens* endolysins PlyCP10, PlyCP18, PlyCP33, PlyCP41, or PlyCP26.

15. The chimeric recombinant lysin polypeptide of claim 12, wherein the thermophile endolysin catalytic domain is from PlyGVE2 and the cell wall binding domain is selected from from *C. perfringens* endolysins PlyCP10, PlyCP18, PlyCP33, PlyCP41, or PlyCP26; and wherein the chimeric recombinant lysin does not have an amino acid sequence of SEQ ID NO: 28.

16. The chimeric recombinant lysin polypeptide of claim 12, wherein the polypeptide comprises a polyhistidine tag.

17. The chimeric recombinant lysin polypeptide of claim 12, wherein:

the amino acid sequence of the thermophile endolysin catalytic domain is SEQ ID NO: 4; SEQ ID NO: 16; or SEQ ID N: 23;

the amino acid sequence of the cell wall binding domain is SEQ ID NO: 5; SEQ ID NO: 6; SEQ ID NO: 7; SEQ ID NO: 8; or SEQ ID NO: 9; and wherein the chimeric recombinant lysin does not have an amino acid sequence of SEQ ID NO: 28.

18. The chimeric recombinant lysin polypeptide of claim 17, wherein the polypeptide has an amino acid sequence of SEQ ID NO: 10; SEQ ID NO: 11; SEQ ID NO: 12; SEQ ID NO: 13; SEQ ID NO: 14; SEQ ID NO: 17; SEQ ID NO: 18; SEQ ID NO: 19; SEQ ID NO: 20; SEQ ID NO: 21; SEQ ID NO: 24; SEQ ID NO: 25; SEQ ID NO: 26; or SEQ ID NO: 27.

19. A host cell comprising the polypeptide of claim 12.

20. The host cell of claim 19, wherein the host cell is selected from a bacterial cell, a fungal cell, a plant cell, and a mammalian cell.

21. A composition comprising the chimeric recombinant lysin polypeptide of claim 12, and optionally a pharmaceutically acceptable carrier.

22. The composition of claim 21, comprising a pharmaceutically acceptable carrier.

23. The composition of claim 21, wherein the composition is formulated for oral administration.

24. The composition of claim 23, where the composition is animal feed.

25. A method of treating infection and disease caused by *C. perfringens* in an individual in need thereof, comprising administering to said individual an effective dose of the composition of claim 23.

26. The method of claim 25, wherein the infection is necrotic enteritis.

27. The method of claim 25, wherein the individual is a chicken, a pig, or newborn calf.

28. The method of claim 25, wherein the infection is gas gangrene.

29. A method of preparing a chimeric recombinant lysin polypeptide, comprising cultivating the host cell of claim 10 in a suitable medium, under conditions that allow expression of the polypeptide, preparing the polypeptide, and optionally further comprising recovering the polypeptide.

30. A method of treating infection and disease caused by *C. perfringens* in an individual in need thereof, comprising administering to said individual the host cell of claim 11.

* * * * *